(12) United States Patent
Wakamiya et al.

(10) Patent No.: US 10,211,401 B2
(45) Date of Patent: Feb. 19, 2019

(54) ORGANIC SEMICONDUCTOR MATERIAL

(71) Applicant: TOYOBO CO., LTD., Osaka-shi, Osaka (JP)

(72) Inventors: Atsushi Wakamiya, Uji (JP); Kazutake Hagiya, Otsu (JP); Shiro Hamamoto, Otsu (JP); Hikaru Tanaka, Otsu (JP)

(73) Assignee: TOYOBO CO., LTD., Osaka-shi (JP)

( * ) Notice: Subject to any disclaimer, the term of this patent is extended or adjusted under 35 U.S.C. 154(b) by 30 days.

(21) Appl. No.: 15/118,658

(22) PCT Filed: Feb. 3, 2015

(86) PCT No.: PCT/JP2015/053004
§ 371 (c)(1),
(2) Date: Aug. 12, 2016

(87) PCT Pub. No.: WO2015/122321
PCT Pub. Date: Aug. 20, 2015

(65) Prior Publication Data
US 2017/0069845 A1    Mar. 9, 2017

(30) Foreign Application Priority Data
Feb. 14, 2014    (JP) ................. 2014-026951

(51) Int. Cl.
*C08G 75/00*    (2006.01)
*H01L 51/00*    (2006.01)
(Continued)

(52) U.S. Cl.
CPC ........ *H01L 51/0036* (2013.01); *C07D 513/04* (2013.01); *C07F 7/0814* (2013.01);
(Continued)

(58) Field of Classification Search
CPC ..... H01L 51/0069; H01L 51/43; H01L 51/36; H01L 51/558; C08G 2261/3243;
(Continued)

(56) References Cited

U.S. PATENT DOCUMENTS

2009/0230386 A1    9/2009    Yamamoto et al.
2015/0059853 A1    3/2015    Tokito et al.

FOREIGN PATENT DOCUMENTS

JP    2007-238530 A    9/2007
JP    2009-197218 A    9/2009
(Continued)

OTHER PUBLICATIONS

Extended (supplementary) European Search Report dated Sep. 6, 2017, issued in counterpart European Application No. 15749645.6. (7 pages).
(Continued)

*Primary Examiner* — Shane Fang
(74) *Attorney, Agent, or Firm* — Westerman, Hattori, Daniels & Adrian, LLP

(57) ABSTRACT

Provided are: a macromolecular compound for providing an organic semiconductor material exhibiting excellent conversion efficiency; a starting-material compound having high material design freedom; and methods for producing the same.

The macromolecular compound according to the present invention comprising a benzobisthiazole structural unit represented by the formula (1):
(Continued)

[Chemical Formula 1]

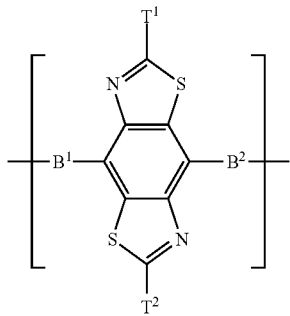

(1)

[in the formula (1), $T^1$ and $T^2$ each independently represent an alkoxy group, a thioalkoxy group, a thiophene ring optionally substituted by a hydrocarbon group or an organosilyl group, a thiazole ring optionally substituted by a hydrocarbon group or an organosilyl group, or a phenyl group optionally substituted by a hydrocarbon group, an alkoxy group, a thioalkoxy group, an organosilyl group, a halogen atom or a trifluoromethyl group; and $B^1$ and $B^2$ each represent a thiophene ring optionally substituted by a hydrocarbon group, a thiazole ring optionally substituted by a hydrocarbon group, or an ethynylene group].

9 Claims, 10 Drawing Sheets

(51) Int. Cl.
  C07F 7/22        (2006.01)
  C07D 513/04      (2006.01)
  C08G 61/12       (2006.01)
  C07F 7/08        (2006.01)
  H01L 51/05       (2006.01)
  H01L 51/42       (2006.01)

(52) U.S. Cl.
  CPC .......... *C07F 7/2208* (2013.01); *C08G 61/123* (2013.01); *C08G 61/126* (2013.01); *H01L 51/0035* (2013.01); *H01L 51/0043* (2013.01); *H01L 51/0094* (2013.01); *C08G 2261/124* (2013.01); *C08G 2261/149* (2013.01); *C08G 2261/1412* (2013.01); *C08G 2261/3223* (2013.01); *C08G 2261/3229* (2013.01); *C08G 2261/3241* (2013.01); *C08G 2261/3243* (2013.01); *C08G 2261/3246* (2013.01); *C08G 2261/334* (2013.01); *C08G 2261/3328* (2013.01); *C08G 2261/344* (2013.01); *C08G 2261/413* (2013.01); *C08G 2261/91* (2013.01); *H01L 51/0558* (2013.01); *H01L 51/424* (2013.01)

(58) Field of Classification Search
  CPC ........ C08G 2261/124; C08G 2261/414; C08G 2261/92; C08G 2261/95; C08G 2261/91; Y02E 10/549
  USPC .......... 528/377, 378, 380; 136/263; 257/40, 257/E51.005, E51.024; 313/504; 977/734, 948
  See application file for complete search history.

(56) References Cited

FOREIGN PATENT DOCUMENTS

| | | |
|---|---|---|
| JP | 2010-53093 A | 3/2010 |
| WO | 2013/141182 A1 | 9/2013 |
| WO | 2015/033597 A1 | 3/2015 |

OTHER PUBLICATIONS

Office Action dated Aug. 2, 2017, issued in counterpart Chinese Application No. 201580008203.8, with English translation. (21 pages).
Kim et al., Synthesis, characterization, and properties of a new thiophene-benzobisthiazole copolymer, Synthetic Metals, 2006, vol. 156, pp. 38-41, cited in ISR (4 pages).
Mike et al., "Facile Synthesis of 2,6-Disubstituted Benzobisthiazoles: Functional Monomers for the Design of Organic Semiconductors", The Journal of Organic Chemistry, 2010, vol. 75, pp. 495-497, cited in ISR (3 pages).
Tashiro et al., "Calculation of Limiting Young's Moduli of Rigid-Rod Polymers Including Poly-p-Phenylene Benzobisthiazole (PBT)", Sen-I Gakkaishi, 1987, vol. 43, No. 2, pp. 78-91, cited in ISR (14 pages).
International Search Report dated Apr. 21, 2015, issued in counterpart International Application No. PCT/ JP2015/053004 (2 pages).
Office Action dated Apr. 28, 2018, issued in counterpart Chinese Application No. 201580008203.8 with English translation. (13 pages).
Office Action dated Aug. 7, 2018, issued in counterpart Japanese application No. 2015-562789, with English translation. (9 pages).
Office Action dated Dec. 4, 2018, issued in counterpart Japanese Application No. 2015-562789, with English translation. (9 pages).

[Fig.1]
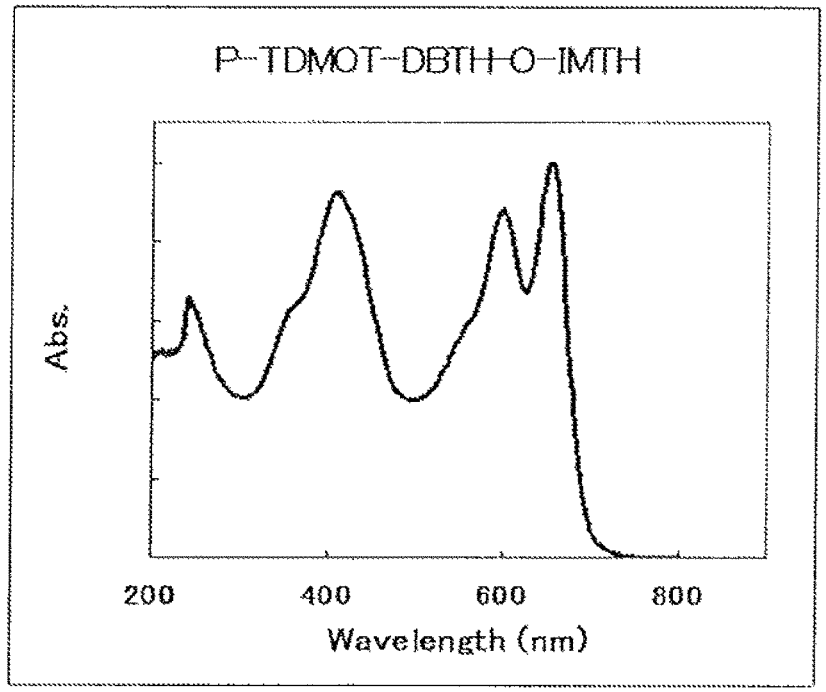
[Fig.2]
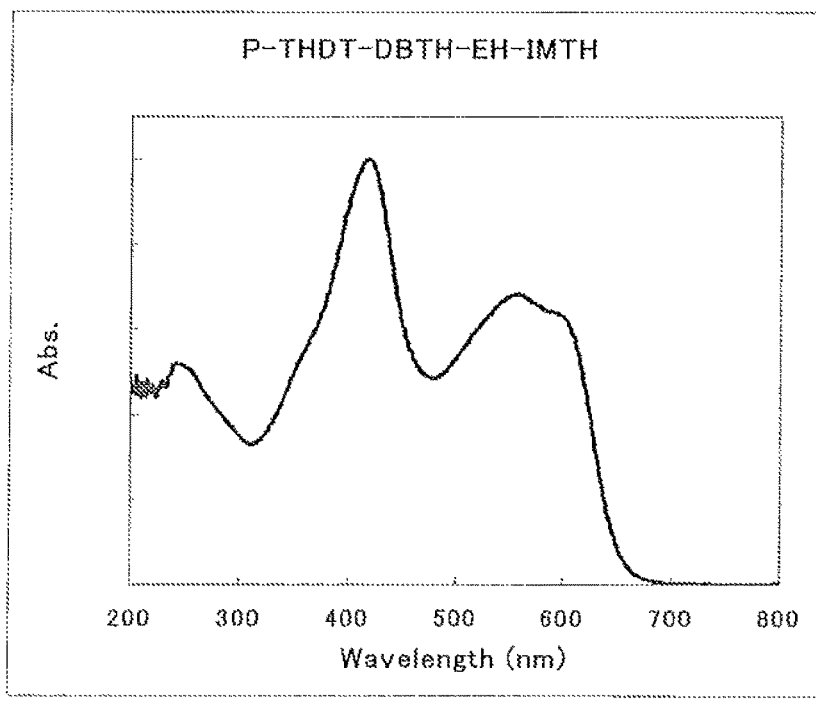

[Fig.3]
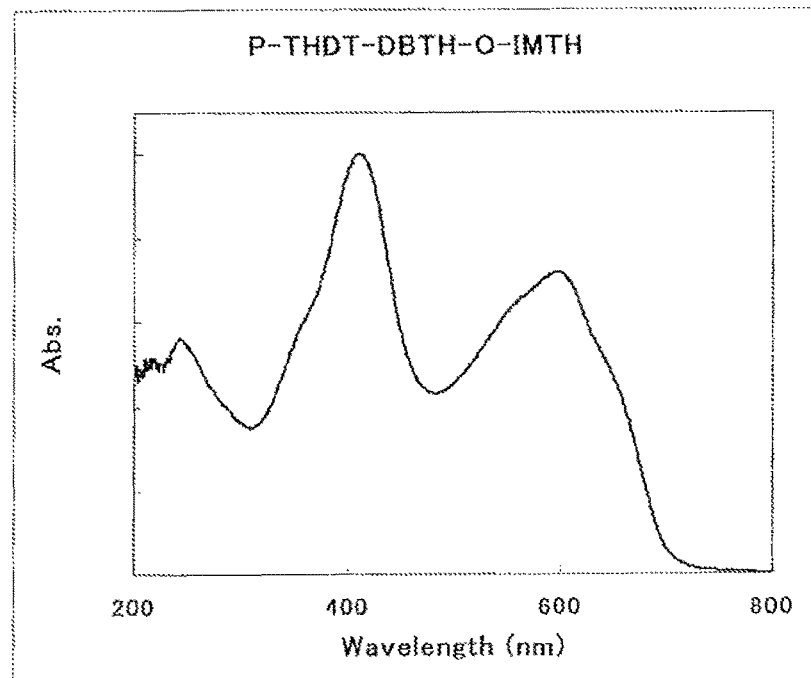
[Fig.4]
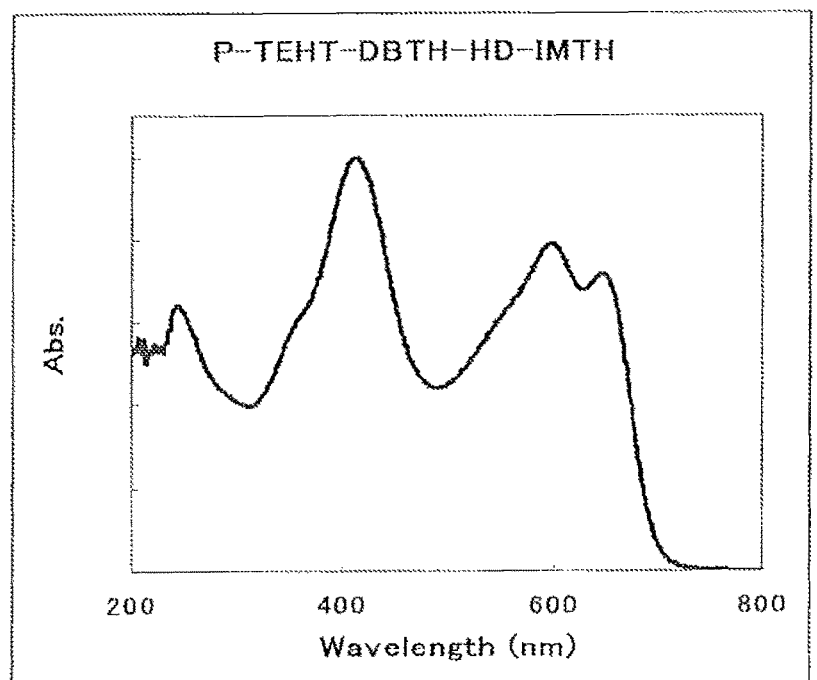

[Fig.5]
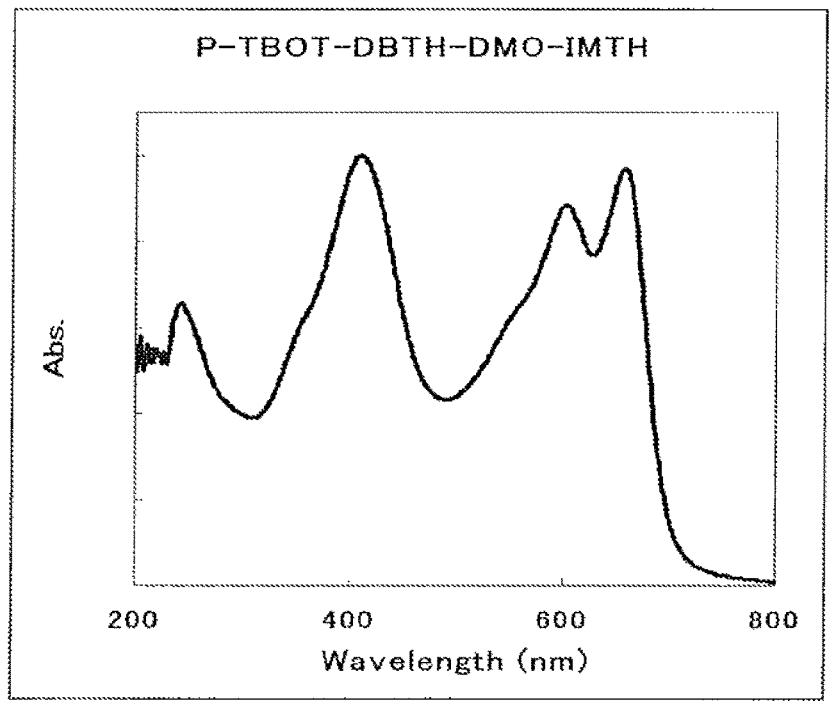
[Fig.6]
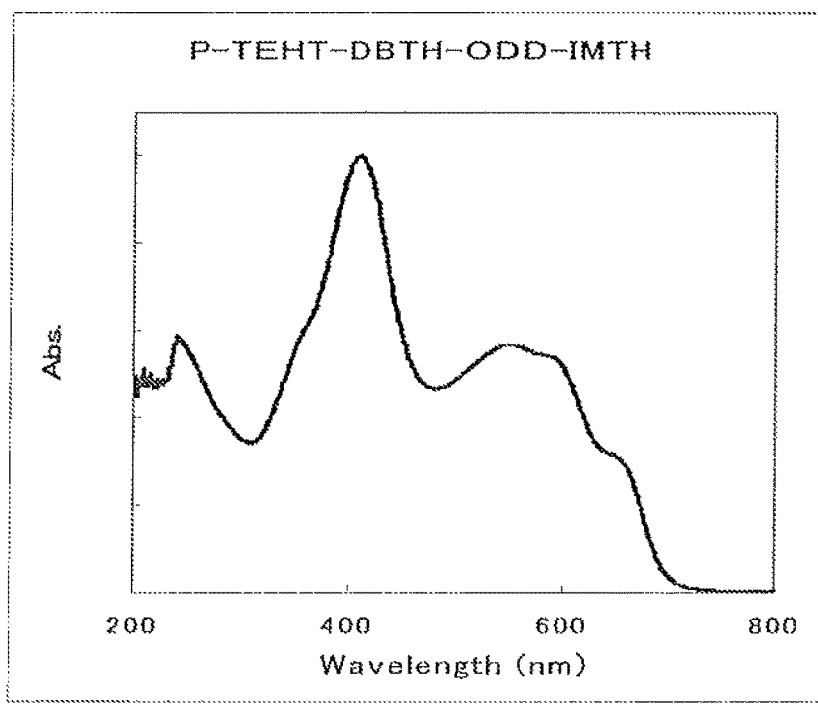

[Fig.7]
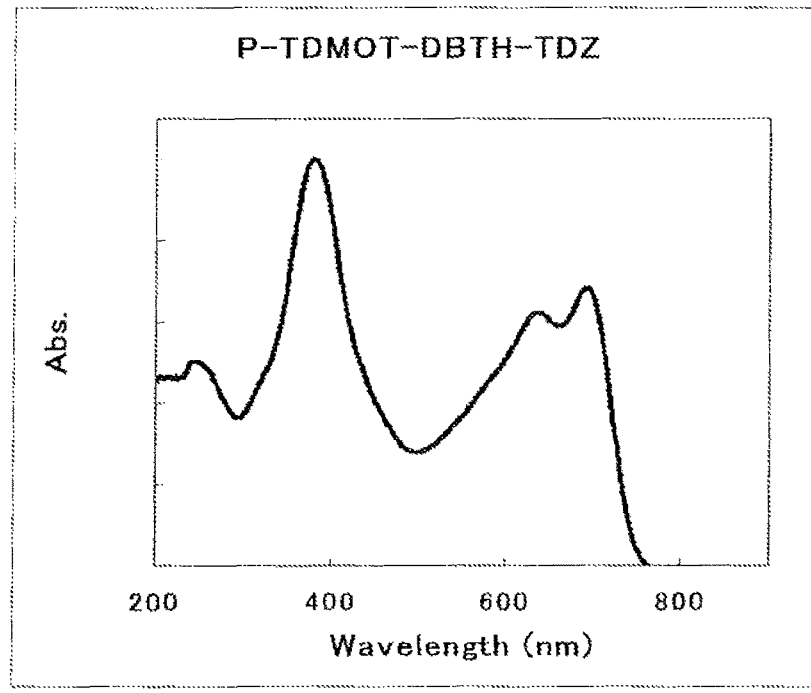
[Fig.8]
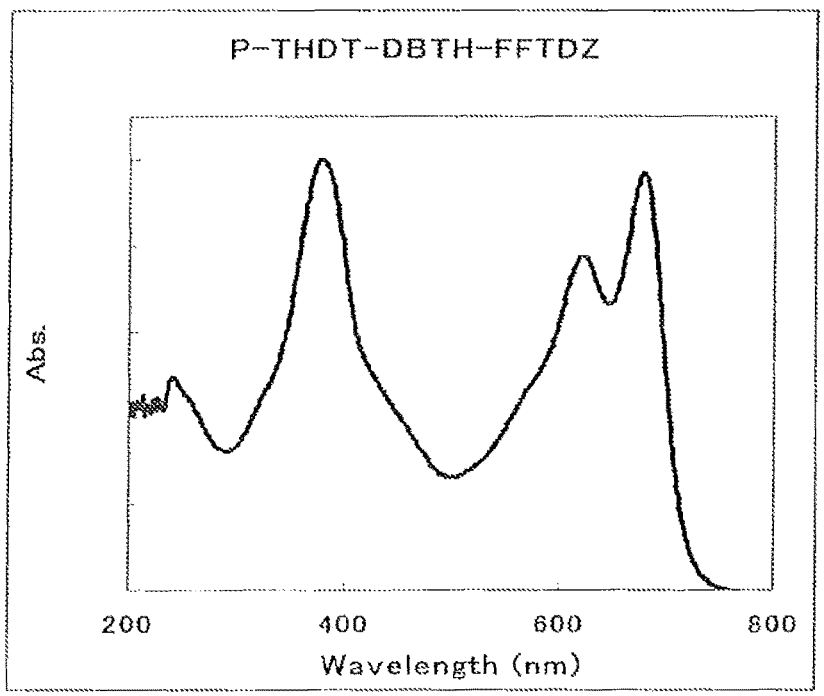

[Fig.9]
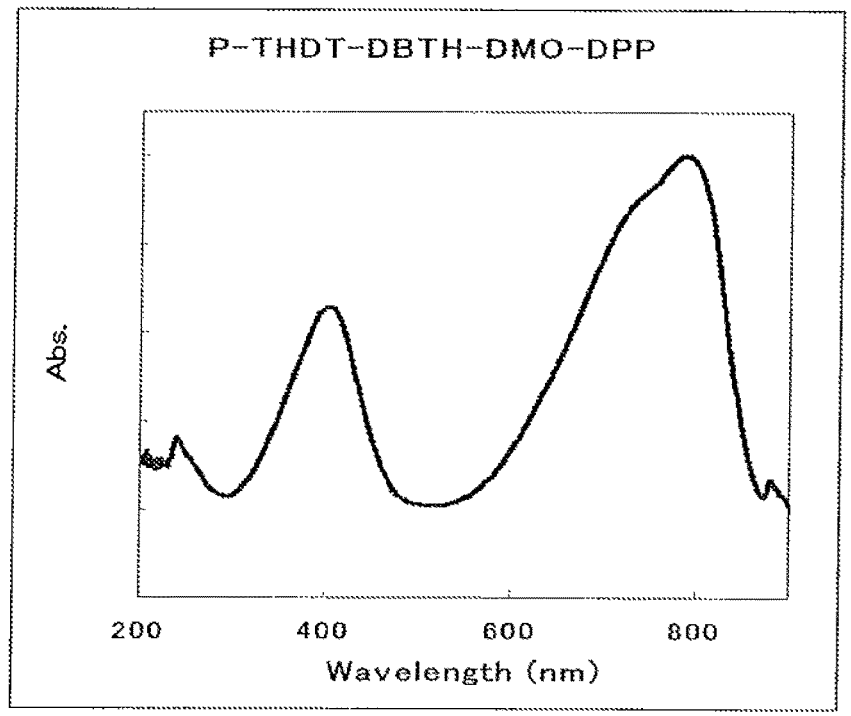
[Fig.10]
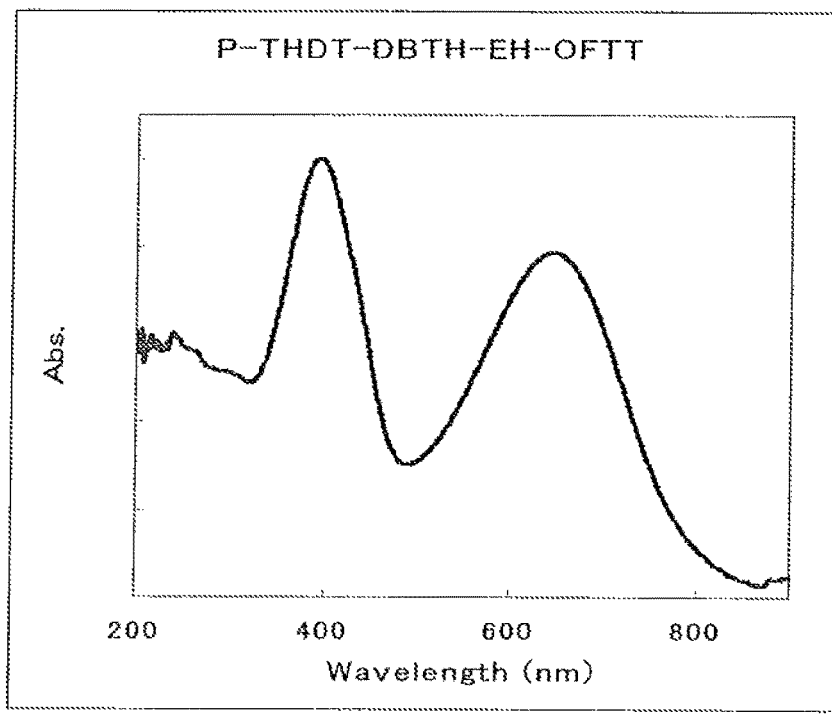

[Fig.11]
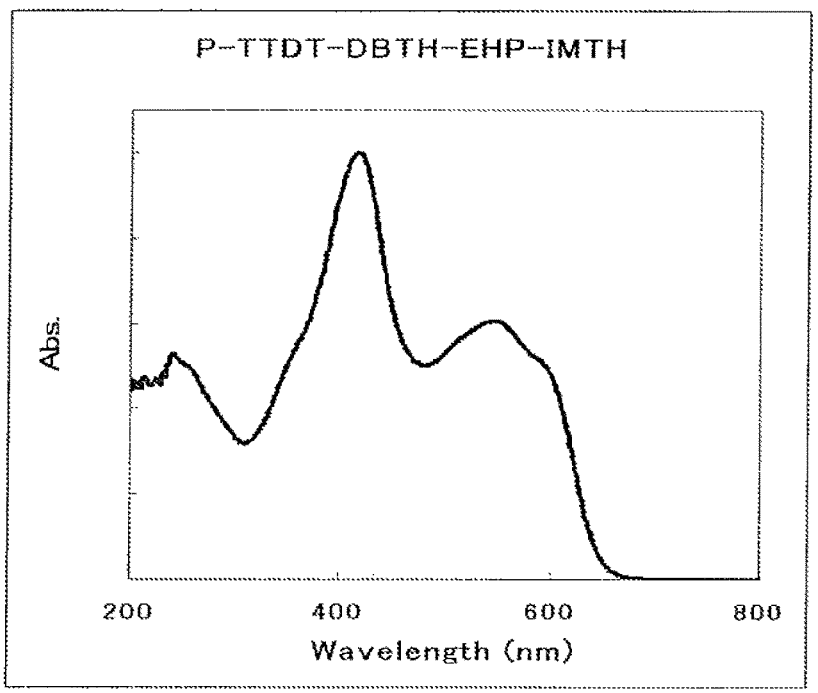
[Fig.12]
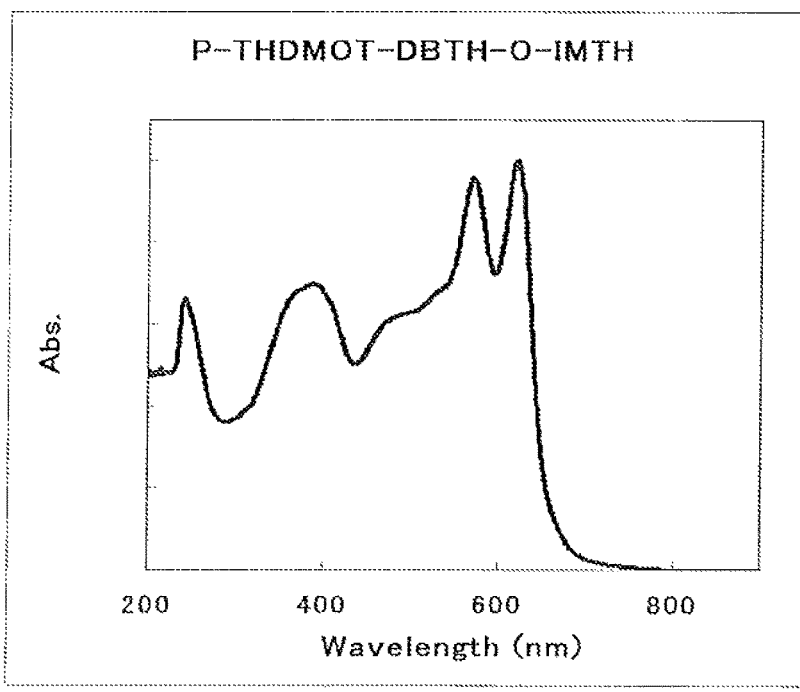

[Fig.13]
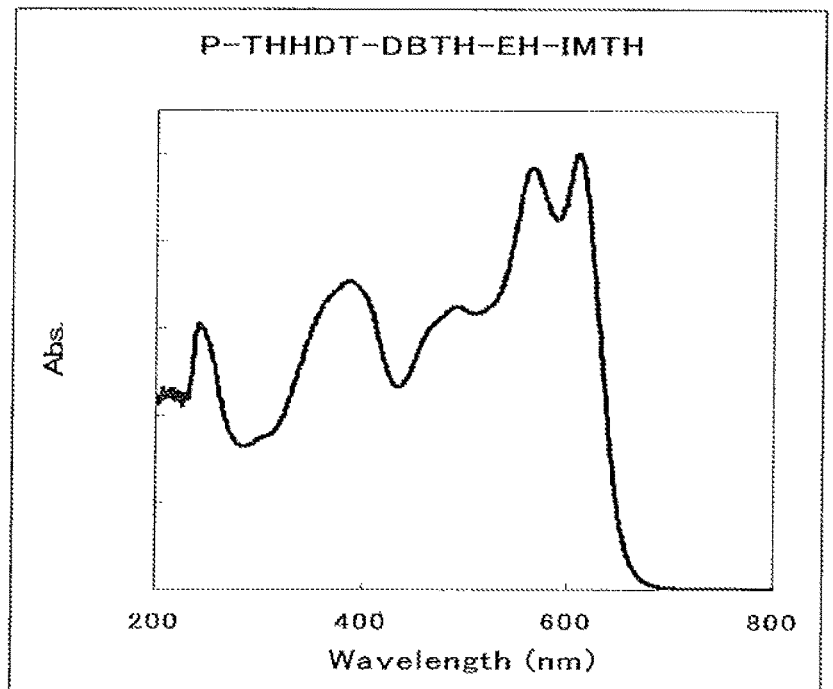
[Fig.14]
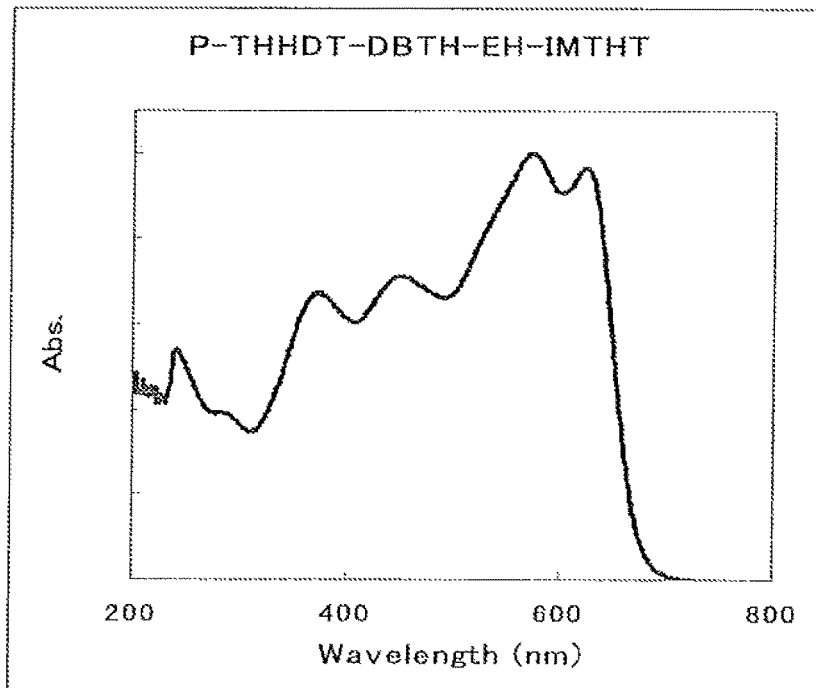

[Fig.15]
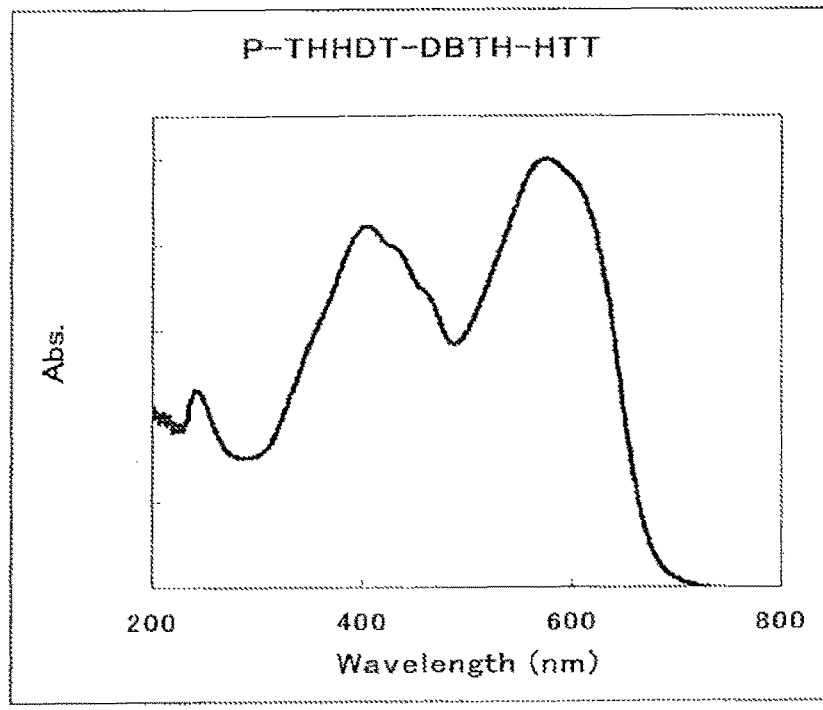
[Fig.16]
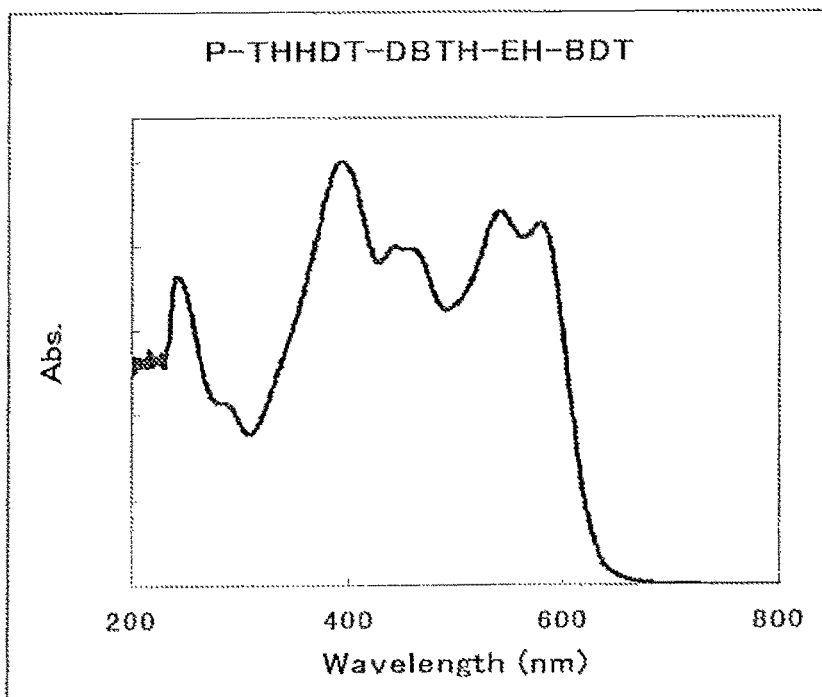

[Fig.17]
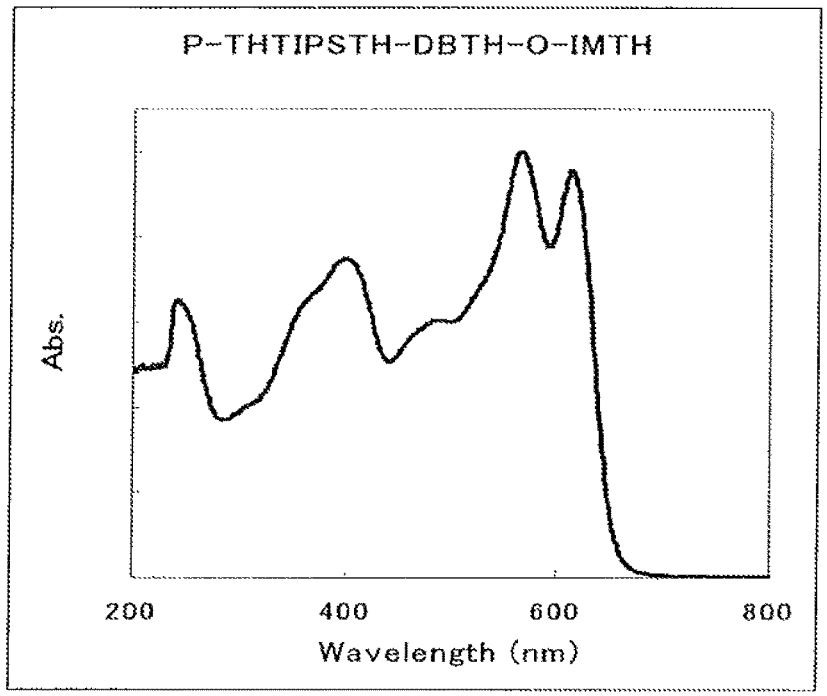
[Fig.18]
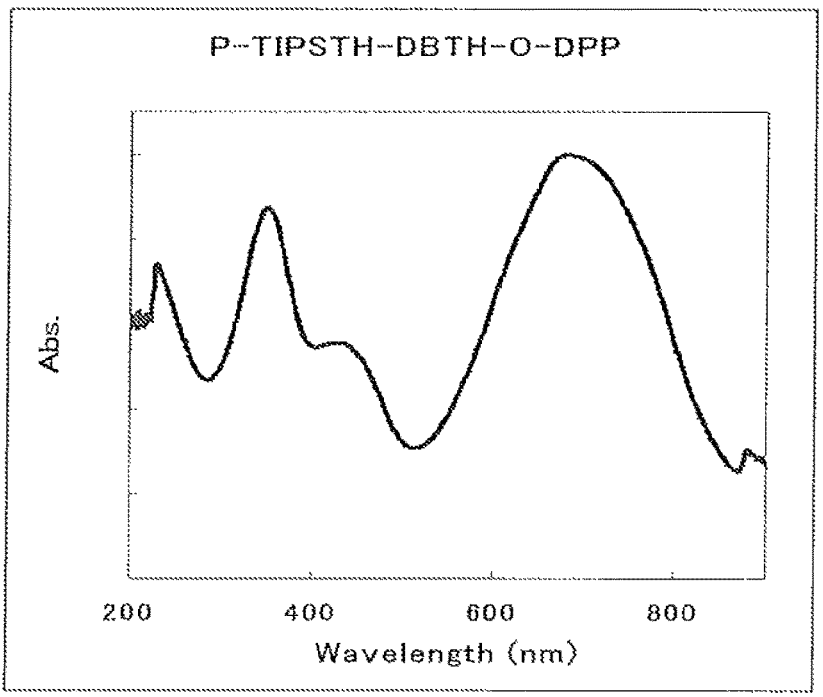

[Fig.19]
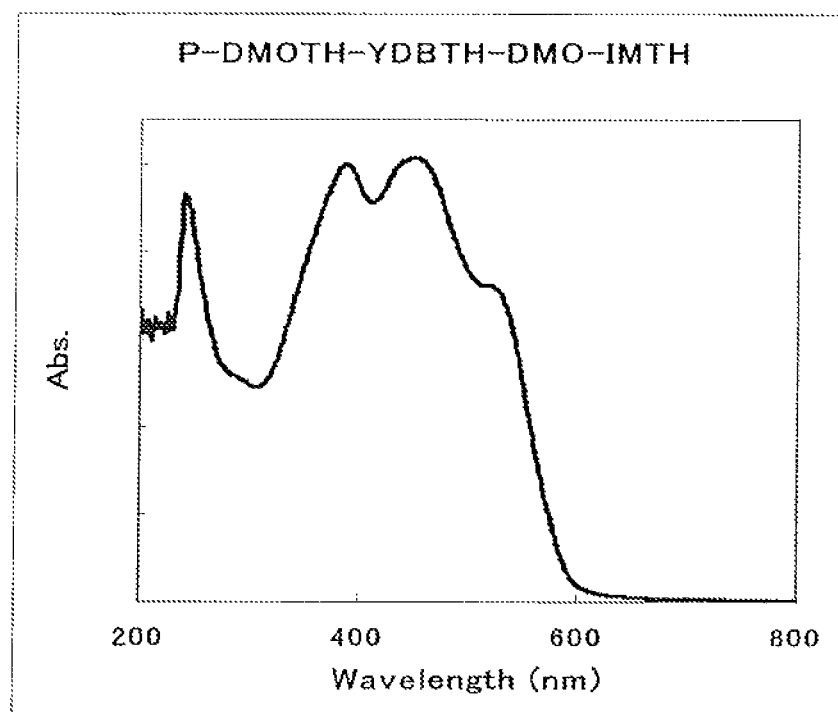

ORGANIC SEMICONDUCTOR MATERIAL

TECHNICAL FIELD

The present invention relates to a macromolecular compound comprising a structural unit having a specific benzobisthiazole backbone; an organic semiconductor material; and a method for production thereof.

BACKGROUND ART

Organic semiconductor materials are one of the most important materials in the field of organic electronics, and can be classified into electron-donating p-type organic semiconductor materials and electron-accepting n-type organic semiconductor materials. Various semiconductor elements can be produced by appropriately combining p-type organic semiconductor materials and n-type organic semiconductor materials, and these elements are applied to, for example, organic electroluminescences which emit light under the action of excitons formed by recombination of electrons and holes, organic thin-film solar cells which convert light into electric power, and organic thin-film transistors which control an amperage and a voltage.

Among them, organic thin-film solar cells are useful for environmental conservation because they do not release carbon dioxide into the air, and also, organic thin-film solar cells are easily produced because they have a simple structure. Therefore, the demand of organic thin-film solar cells is increasing. However, the photoelectric conversion efficiency of the organic thin-film solar cell is not sufficient yet. The photoelectric conversion efficiency η is a value calculated as a product of a short-circuit current density (Jsc), an open circuit voltage (Voc) and a fill factor (FF) (η=open circuit voltage (Voc)× short circuit current density (Jsc)× fill factor (FF)), and for improving the photoelectric conversion efficiency, it is necessary to improve the short-circuit current density (Jsc) and the fill factor (FF) as well as the open circuit voltage (Voc).

The open circuit voltage (Voc) is proportional to a difference in energy between the HOMO (highest occupied molecular orbital) level of a p-type organic semiconductor and the LUMO (lowest unoccupied molecular orbital) level of a n-type organic semiconductor, and therefore for improving the open circuit voltage (Voc), it is necessary to deepen (lower) the HOMO level of the p-type organic semiconductor.

The short-circuit current density (Jsc) correlates to the amount of energy received by an organic semiconductor material, and for improving the short-circuit current density (Jsc) of the organic semiconductor material, it is necessary for the organic semiconductor material to absorb light in a wide wavelength range extending from a visible region to a near-infrared region. The wavelength of a light having the lowest energy in the light that can be absorbed by the organic semiconductor material (the longest wavelength) is an absorption edge wavelength, and the energy corresponding to this wavelength is equal to band gap energy. Accordingly, for the organic semiconductor material to absorb light in a wider wavelength range, it is necessary to narrow the band gap (difference in energy between the HOMO level and the LUMO level of the p-type organic semiconductor).

On the other hand, in Patent Document 1, a compound having a benzobisthiazole backbone is proposed, but conversion efficiency is not known.

PRIOR ART DOCUMENT

Patent Document

Patent Document 1: JP-A-2007-238530

SUMMARY OF THE INVENTION

Problems to be Solved by the Invention

An object of the present invention is to provide an organic semiconductor material that is excellent in photoelectric conversion efficiency. Since in an organic semiconductor material, the chemical structure and the conversion efficiency are closely related to each other, another object of the present invention is to provide a raw material compound capable of introducing more diverse backbones and substituents. Still another object of the present invention is to provide a method for producing the organic semiconductor material and a raw material compound for the organic semiconductor material.

Solutions to the Problems

The present inventors have found that for improving the conversion efficiency, i.e. improving both the open circuit voltage (Voc) and the short-circuit current density (Jsc), it is useful to moderately deepen the HOMO level while causing a p-type organic semiconductor to absorb light in a wide wavelength range. The present inventors have extensively conducted studies with attention paid to a correlation between the conversion efficiency and the chemical structure in the p-type organic semiconductor material, and resultantly learned that by using an organic semiconductor polymer having a specific structure, light with a wide range of wavelengths in the whole visible light region is absorbed, and the HOMO level and the LUMO level can be adjusted to be in an appropriate range, so that both the open circuit voltage (Voc) and the short-circuit current density (Jsc) can be improved. The present inventors have found that when the organic semiconductor polymer is used, charge separation can easily occur between a p-type organic semiconductor and a n-type organic semiconductor, leading to completion of the present invention.

Thus, a macromolecular compound according to the present invention comprises a benzobisthiazole structural unit represented by the formula (1):

[Chemical formula 1]

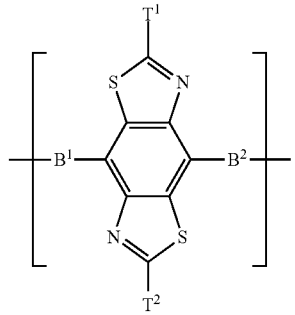

[in the formula (1), $T^1$ and $T^2$ each independently represent an alkoxy group, a thioalkoxy group, a thiophene ring optionally substituted by a hydrocarbon group or an organosilyl group, a thiazole ring optionally substituted by a hydrocarbon group or an organosilyl group, or a phenyl group optionally substituted by a hydrocarbon group, an alkoxy group, a thioalkoxy group, an organosilyl group, a halogen atom or a trifluoromethyl group; and $B^1$ and $B^2$ each represent a thiophene ring optionally substituted by a hydrocarbon group, a thiazole ring optionally substituted by a hydrocarbon group, or an ethynylene group].

In the formula (1), $T^1$ and $T^2$ are each preferably a group represented by any one of the following formulae (t1) to (t5).

[Chemical formula 2]

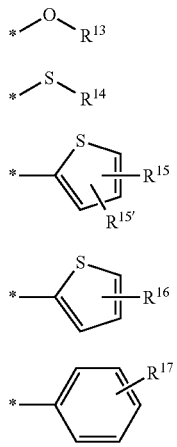

(t1)
(t2)
(t3)
(t4)
(t5)

[in the formulae (t1) to (t5), $R^{13}$ and $R^{14}$ each independently represent a hydrocarbon group with a carbon number of 6 to 30; $R^{15}$ and $R^{16}$ each independently represent a hydrocarbon group with a carbon number of 6 to 30, or a group represented by *—Si$(R^{16})_3$; $R^{15'}$ represents a hydrogen atom, a hydrocarbon group with a carbon number of 6 to 30, or a group represented by *—Si$(R^{18})_3$; $R^{17}$s each independently represent a hydrocarbon group with a carbon number of 6 to 30, *—O—$R^{19}$, *—S—$R^{20}$, *—Si$(R^{18})_3$ or *—CF$_3$; $R^{18}$s each independently represent an aliphatic hydrocarbon group with a carbon number of 1 to 20, or an aromatic hydrocarbon group with a carbon number of 6 to 10, and a plurality of $R^{18}$s may be each same or different: $R^{19}$ and $R^{20}$ each represent a hydrocarbon group with a carbon number of 6 to 30; and * represents a bond].

In the formula (1), $B^1$ and $B^2$ are each preferably a group represented by any one of the following formulae (b1) to (b3).

[Chemical formula 3]

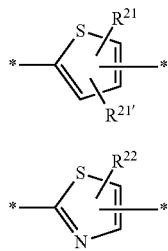

(b1)
(b2)
(b3)

[in the formulae (b1) to (b3), $R^{21}$, $R^{22}$ and $R^{21'}$ each represent a hydrogen atom, or a hydrocarbon group with a carbon number of 6 to 30; and * represents a bond, and in particular, * on the left side represents a bond of a benzobisthiazole compound to a benzene ring].

The macromolecular compound according to the present invention is preferably a donor-acceptor-type semiconductor polymer. An organic semiconductor material comprising the macromolecular compound according to the present invention is also encompassed in the technical scope of the present invention.

The present invention includes a benzobisthiazole compound represented by the formula (5):

[Chemical formula 4]

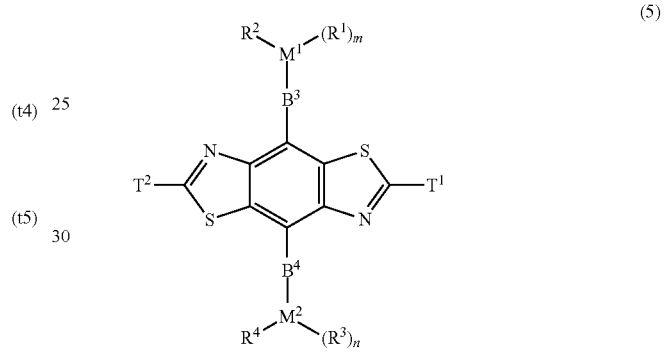

(5)

[In the formula (5), $T^1$ and $T^2$ each represent a group similar to one described above. $B^3$ and $B^4$ each represent a thiophene ring optionally substituted by an alkyl group; or a thiazole ring optionally substituted by an alkyl group; $R^1$ to $R^4$ each independently represent an aliphatic hydrocarbon group with a carbon number of 1 to 6, hydroxyl group, an alkoxy group with a carbon number of 1 to 6, or an aryloxy group with a carbon number of 6 to 10; $M^1$ and $M^2$ each independently represent a boron atom or a tin atom; $R^1$ and $R^2$ may form a ring with $M^1$, $R^3$ and $R^4$ may form a ring with $M^2$; and m and n each represent an integer of 1 or 2, and when m and n each represent 2, a plurality of $R^1$s and a plurality of $R^3$s may be each same or different].

The present invention includes a benzobisthiazole compound represented by the formula (4):

[Chemical formula 5]

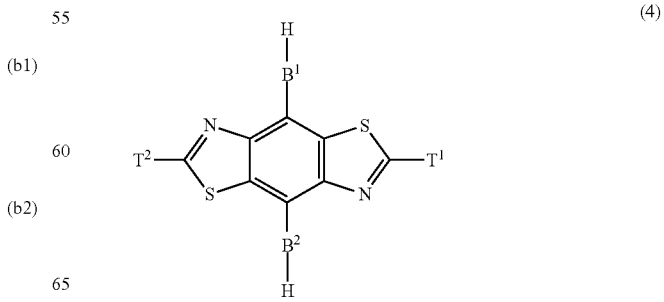

(4)

[In the formula (4), $T^1$, $T^2$, $B^1$ and $B^2$ each represent a group similar to one described above].

The present invention further includes a benzobisthiazole compound represented by the formula (3):

[Chemical formula 6]

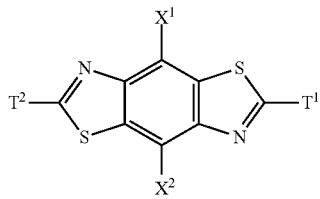

(3)

[In the formula (3), $T^1$ and $T^2$ each represent a group similar to one described above; $X^1$ and $X^2$ each represent a halogen atom].

The present invention further includes a benzobisthiazole compound represented by the formula (2):

[Chemical formula 7]

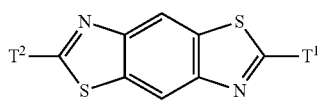

(2)

[In the formula (2), $T^1$ and $T^2$ each represent a group similar to one described above].

A production method for the macromolecular compound according to the present invention comprising: using a compound selected from the group consisting of 2,6-diiodobenzo[1,2-d:4,5-d']bisthiazole and 2,6-dibromobenzo[1,2-d:4,5-d']bisthiazole as a starting material; and going through a compound represented by the formula (2):

[Chemical Formula 8]

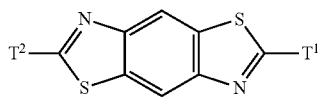

(2)

[in the formula (2), $T^1$ and $T^2$ each represent a group similar to one described above]:
a compound represented by the formula (3):

[Chemical Formula 9]

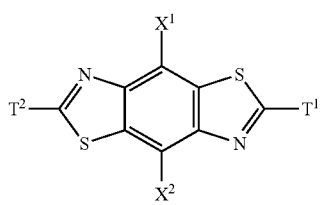

(3)

[in the formula (3), $T^1$, $T^2$, $X^1$, and $X^2$ each represent a group similar to one described above]: and a compound represented by the formula (4):

[Chemical Formula 10]

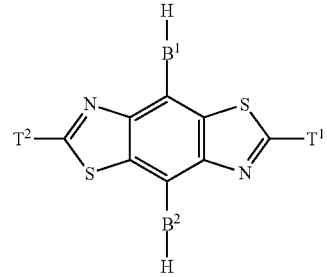

(4)

[in the formula (4), $T^1$, $T^2$, $B^1$, and $B^2$ each represent a group similar to one described above].

Preferably, the production method for the macromolecular compound according to the present invention includes the following first step, second step, and third step.

First step: a step of reacting a compound represented by the formula (6) and/or formula (7):

[Chemical Formula 11]

$T^1$-$R^5$ (6)

$T^2$-$R^6$ (7)

[in the formulae (6) and (7), $T^1$ and $T^2$ each represent a group similar to one described above; $R^5$ and $R^6$ each independently represent a hydrogen atom or *-$M^3(R^7)_k R^8$; $R^7$ and $R^8$ each independently represent an aliphatic hydrocarbon group with a carbon number of 1 to 6, hydroxyl group, an alkoxy group with a carbon number of 1 to 6, or an aryloxy group with a carbon number of 6 to 10; $M^3$ represents a boron atom or a tin atom, and * represents a bond; $R^7$ and $R^8$ may form a ring with $M^3$; and k represents an integer of 1 or 2, and when k is 2, a plurality of $R^7$s may be each same or different]

with a compound selected from the group consisting of 2,6-diiodobenzo[1,2-d:4,5-d']bisthiazole and 2,6-dibromobenzo[1,2-d:4,5-d']bisthiazole in the presence of a metal catalyst to prepare a compound represented by the formula (2);

the second step: a step of reacting a base and a halogenation reagent with the compound represented by the formula (2) to prepare a compound represented by the formula (3); and the third step: a step of reacting a compound represented by the following formula (8) and/or formula (9) with the compound represented by the formula (3) in the presence of a metal catalyst to prepare a compound represented by the formula (4):

[Chemical Formula 12]

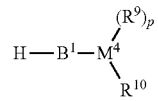

(8)

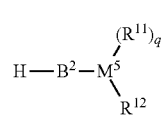

(9)

[in the formulae (8) and (9), $B^1$ and $B^2$ each represent a group similar to one described above; $R^9$ to $R^{12}$ each independently represent an aliphatic hydrocarbon group with a carbon number of 1 to 6, hydroxyl group, an alkoxy group with a carbon number of 1 to 6, an aryl group with a carbon number of 6 to 10, or an aryloxy group with a carbon number of 6 to 10; $M^4$ and $M^5$ each represent a boron atom, a tin atom or a silicon atom; $R^9$ and $R^{10}$ may form a ring with $M^4$, and $R^{11}$ and $R^{12}$ may form a ring with $M^5$; and p and q each represent an integer of 1 or 2, and when p is 2, a plurality of $R^9$s may be each same or different, and when q is 2, a plurality of $R^{11}$s may be each same or different].

Preferably, the production method for the macromolecular compound according to the present invention further going through a compound represented by the formula (5).

[Chemical Formula 13]

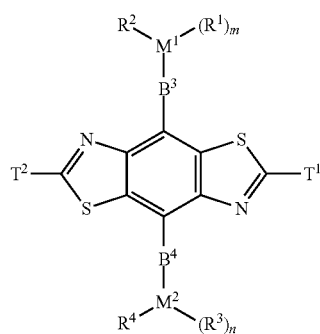

(5)

[in the formula (5), $T^1$, $T^2$, $B^3$, $B^4$, $R^1$ to $R^4$, $M^1$, $M^2$, m and n each represent a group similar to one described above].

Preferably, the production method for the macromolecular compound according to the present invention further comprising the following fourth step:

the fourth step: a step of reacting a base and a tin halide compound with a compound represented by the formula (4) to prepare a compound represented by the formula (5).

A benzobisthiazole compound according to the present invention can form a planar cross-shaped backbone under the intramolecular S—N interaction. As a result, a π-conjugation is extended in the planar cross-shaped backbone, and therefore the benzobisthiazole compound has multi-band light absorptions derived from a plurality of π-π* transitions, and can absorb light in a wide wavelength range extending from a visible region to a near-infrared region. Accordingly, both a high open circuit voltage (Voc) and a high short-circuit current density (Jsc) can be achieved, so that a high photoelectric conversion efficiency η can be achieved. According to a production method according to the present invention, various substituents can be introduced into the benzobisthiazole backbone, so that the properties (e.g. crystallinity, film formability and absorption wavelength) of a material can be controlled.

BRIEF DESCRIPTION OF THE DRAWINGS

FIG. 1 shows an ultraviolet visible absorption spectrum of a macromolecular compound in Example 22.

FIG. 2 shows an ultraviolet visible absorption spectrum of a macromolecular compound in Example 23.

FIG. 3 shows an ultraviolet visible absorption spectrum of a macromolecular compound in Example 24.

FIG. 4 shows an ultraviolet visible absorption spectrum of a macromolecular compound in Example 25.

FIG. 5 shows an ultraviolet visible absorption spectrum of a macromolecular compound in Example 26.

FIG. 6 shows an ultraviolet visible absorption spectrum of a macromolecular compound in Example 27.

FIG. 7 shows an ultraviolet visible absorption spectrum of a macromolecular compound in Example 28.

FIG. 8 shows an ultraviolet visible absorption spectrum of a macromolecular compound in Example 29.

FIG. 9 shows an ultraviolet visible absorption spectrum of a macromolecular compound in Example 30.

FIG. 10 shows an ultraviolet visible absorption spectrum of a macromolecular compound in Example 31.

FIG. 11 shows an ultraviolet visible absorption spectrum of a macromolecular compound in Example 32.

FIG. 12 shows an ultraviolet visible absorption spectrum of a macromolecular compound in Example 37.

FIG. 13 shows an ultraviolet visible absorption spectrum of a macromolecular compound in Example 38.

FIG. 14 shows an ultraviolet visible absorption spectrum of a macromolecular compound in Example 39.

FIG. 15 shows an ultraviolet visible absorption spectrum of a macromolecular compound in Example 40.

FIG. 16 shows an ultraviolet visible absorption spectrum of a macromolecular compound in Example 41.

FIG. 17 shows an ultraviolet visible absorption spectrum of a macromolecular compound in Example 46.

FIG. 18 shows an ultraviolet visible absorption spectrum of a macromolecular compound in Example 47.

FIG. 19 shows an ultraviolet visible absorption spectrum of a macromolecular compound in Example 49.

MODE FOR CARRYING OUT THE INVENTION

1. Macromolecular Compound

The macromolecular compound according to the present invention comprises a benzobisthiazole structural unit represented by the formula (1).

[Chemical Formula 14]

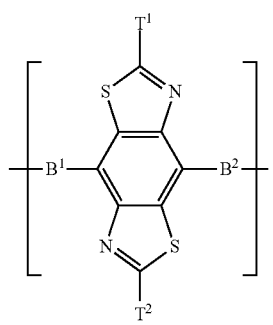

(1)

[in the formula (1), $T^1$ and $T^2$ each independently represent an alkoxy group, a thioalkoxy group, a thiophene ring optionally substituted by a hydrocarbon group or an organosilyl group, a thiazole ring optionally substituted by a hydrocarbon group or an organosilyl group, or a phenyl group optionally substituted by a hydrocarbon group, an alkoxy group, a thioalkoxy group, an organosilyl group, a halogen atom or a trifluoromethyl group; and $B^1$ and $B^2$ each represent a thiophene ring optionally substituted by a hydrocarbon group, a thiazole ring optionally substituted by a hydrocarbon group, or an ethynylene group].

The macromolecular compound according to the present invention has a benzobisthiazole structural unit represented by the formula (1), so that the band gap can be narrowed while the HOMO level is deepened. Thus, the macromolecular compound is advantageous for improving the photoelectric conversion efficiency. The macromolecular compound according to the present invention is preferably a donor-acceptor-type semiconductor polymer. The donor-acceptor-type semiconductor macromolecular compound means a macromolecular compound in which donor units and acceptor units are alternately arranged. The donor unit means an electron-donating structural unit, and the acceptor unit means an electron-accepting structural unit. The donor-acceptor-type semiconductor polymer is preferably a macromolecular compound in which structural units represented by the formula (1) and other structural units are alternately arranged.

In this specification, the organosilyl group means a monovalent group in which a Si atom is substituted with one or more hydrocarbon groups, and the number of hydrocarbon groups with which the Si atom is substituted is preferably 2 or more, further preferably 3.

In the benzobisthiazole structural unit represented by the formula (1), $T^1$ and $T^2$ may be mutually same or different, and they are preferably the same from the viewpoint of ease of production.

In the benzobisthiazole structural unit represented by the formula (1), $T^1$ and $T^2$ are each preferably a group represented by one of the following formulae (t1) to (t5). Specifically, $T^1$ and $T^2$ are each preferably a group represented by the following formula (t1) when they are alkoxy groups; $T^1$ and $T^2$ are each preferably a group represented by the following formula (t2) when they are thioalkoxy groups; $T^1$ and $T^2$ are each preferably a group represented by the following formula (t3) when they are thiophene rings optionally substituted by a hydrocarbon group or an organosilyl group; $T^1$ and $T^2$ are each preferably a group represented by the following formula (t4) when they are thiazole rings optionally substituted by a hydrocarbon group or an organosilyl group; and $T^1$ and $T^2$ are each preferably a group represented by the following formula (t5) when they are phenyl groups optionally substituted by a hydrocarbon group, an alkoxy group, a thioalkoxy group, an organosilyl group, a halogen atom or a trifluoromethyl group. When $T^1$ and $T^2$ are each a group represented by one of the following formulae (t1) to (t5), light having a short wavelength can be absorbed, and high flatness is achieved, so that a π-π stacking is efficiently formed, and therefore the photoelectric conversion efficiency can be further improved.

[Chemical Formula 15]

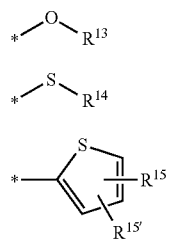

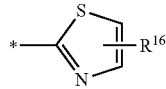

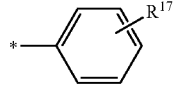

[in the formulae (t1) to (t5), $R^{13}$ and $R^{14}$ each independently represent a hydrocarbon group with a carbon number of 6 to 30; $R^{15}$ and $R^{16}$ each independently represent a hydrocarbon group with a carbon number of 6 to 30, or a group represented by *—Si($R^{18}$)$_3$; $R^{15'}$ represents a hydrogen atom, a hydrocarbon group with a carbon number of 6 to 30, or a group represented by *—Si($R^{18}$)$_3$; $R^{17}$s each independently represent a hydrocarbon group with a carbon number of 6 to 30, *—O—$R^{19}$, *—S—$R^{20}$, *—Si($R^{18}$)$_3$ or *—CF$_3$; $R^{18}$s each independently represent an aliphatic hydrocarbon group with a carbon number of 1 to 20, or an aromatic hydrocarbon group with a carbon number of 6 to 10, and a plurality of $R^{18}$s may be each same or different; $R^{19}$ and $R^{20}$ each represent a hydrocarbon group with a carbon number of 6 to 30; and * represents a bond].

In the above formulae (t1) to (t5), the hydrocarbon groups with a carbon number of 6 to 30 as $R^{13}$ to $R^{17}$, $R^{19}$, $R^{20}$ and $R^{15'}$ are each preferably a branched hydrocarbon group, more preferably a branched chain saturated hydrocarbon group. When the hydrocarbon groups of $R^{13}$ to $R^{17}$, $R^{19}$, $R^{20}$ and $R^{15'}$ are branched, the solubility in an organic solvent can be increased, so that moderate crystallinity can be imparted to the macromolecular compound according to the present invention. The solubility in an organic solvent can be increased as the carbon number of the hydrocarbon groups of $R^{13}$ to $R^{17}$, $R^{19}$, $R^{20}$ and $R^{15'}$ becomes larger, but when the carbon number is excessively large, reactivity in a coupling reaction as described later is reduced, and therefore it is difficult to synthesize a macromolecular compound. Accordingly, the carbon number of the hydrocarbon groups of $R^{13}$ to $R^{17}$, $R^{19}$, $R^{20}$ and $R^{15'}$ is preferably 8 to 25, more preferably 8 to 20, further preferably 8 to 16.

Examples of the hydrocarbon groups with a carbon number of 6 to 30, which are represented by $R^{13}$ to $R^{17}$, $R^{19}$, $R^{20}$ and $R^{15'}$ include alkyl groups with carbon number of 6 such as n-hexyl group; alkyl groups with the carbon number of 7 such as n-heptyl group, alkyl groups with the carbon number of 8 such as n-octyl group, 1-n-butylbutyl group, 1-n-propylpentyl group, 1-ethylhexyl group, 2-ethylhexyl group, 3-ethylhexyl group, 4-ethylhexyl group, 1-methylheptyl group, 2-methylheptyl group, 6-methylheptyl group, 2,4,4-trimethylpentyl group and 2,5-dimethylhexyl group; alkyl groups with the carbon number of 9 such as n-nonyl group, 1-n-propylhexyl group, 2-n-propylhexyl group, 1-ethylheptyl group, 2-ethylheptyl group, 1-methyloctyl group, 2-methyloctyl group, 6-methyloctyl group, 2,3,3,4-tetramethylpentyl group and 3,5,5-trimethylhexyl group; alkyl groups with the carbon number of 10 such as n-decyl group, 1-n-pentylpentyl group, 1-n-butylhexyl group, 2-n-butylhexyl group, 1-n-propylheptyl group, 1-ethyloctyl group, 2-ethyloctyl group, 1-methylnonyl group, 2-methylnonyl group and 3,7-dimethyloctyl group; alkyl groups with the carbon number of 11 such as n-undecyl group, 1-n-butylheptyl group, 2-n-butylheptyl group, 1-n-propyloctyl group, 2-n-propyloctyl group, 1-ethylnonyl group and 2-ethylnonyl group; alkyl groups with the carbon number of 12 such as n-dodecyl group, 1-n-pentylheptyl group, 2-n-pentylheptyl group, 1-n-butyloctyl group, 2-n-butyloctyl group, 1-n-propylnonyl group and 2-n-propylnonyl group; alkyl groups with the carbon number of 13 such as n-tridecyl group, 1-n-pentyloctyl group, 2-n-pentyloctyl group, 1-n-butylnonyl group, 2-n-butylnonyl group, 1-methyldodecyl group and 2-methyldodecyl group; alkyl groups with the carbon number of 14 such as n-tetradecyl group, 1-n-heptylheptyl group, 1-n-hexyloctyl group, 2-n-hexyloctyl group, 1-n-pentylnonyl group and 2-n-pentylnonyl group; alkyl groups with the carbon number of 15 such as n-pentadecyl group, 1-n-heptyloctyl group, 1-n-hexylnonyl group and 2-n-hexylnonyl group; alkyl groups with the carbon number of 16 such as n-hexadecyl group, 2-n-hexyldecyl group, 1-n-octyloctyl group, 1-n-heptylnonyl group and 2-n-heptylnonyl group; alkyl groups with the carbon number of 17 such as n-heptadecyl group and 1-n-octylnonyl group; alkyl groups with the carbon number of 18 such as n-octadecyl group and 1-n-nonylnonyl group; alkyl groups with the carbon number of 19 such as n-nonadecyl group; alkyl groups with the carbon number of 20 such as a-eicosyl group and 2-n-octyldodecyl group; alkyl groups with the carbon number of 21 such as n-heneicosyl group; alkyl groups with the carbon number of 22 such as n-docosyl group; alkyl groups with the carbon number of 23 such as n-tricosyl group; and alkyl groups with the carbon number of 24 such as n-tetracosyl group and 2-n-desyltetradesyl group. Alkyl groups with a carbon number of 8 to 20 are preferable, alkyl groups with a carbon number of 8 to 16 are more preferable, branched chain alkyl groups with a carbon number of 8 to 16 are further preferable, and 2-ethylhexyl group, 3,7-dimethyloctyl group, 2-n-butyloctyl group, 2-n-hexyldecyl group, 2-n-octyldodecyl group and 2-n-decyltetradecyl group are especially preferable. When $R^{13}$ to $R^{17}$, $R^{19}$, $R^{20}$ and $R^{15'}$ are the above-mentioned groups, the macromolecular compound according to the present invention has an increased solubility in an organic solvent, and has moderate crystallinity.

In the groups represented by $*-Si(R^{18})_3$ as $R^{15}$ to $R^{17}$ and $R^{15'}$ in the above formulae (t1) to (t5), the carbon number of the aliphatic hydrocarbon group of $R^{18}$ is preferably 1 to 18, more preferably 1 to 8. Examples of the aliphatic hydrocarbon group of $R^{18}$ include methyl group, ethyl group, isopropyl group, tert-butyl group, isobutyl group, octyl group and octadecyl group. The carbon number of the aromatic hydrocarbon group of $R^{18}$ is preferably 6 to 8, more preferably 6 or 7, especially preferably 6. The aromatic hydrocarbon group of $R^{18}$ is, for example, phenyl group. In particular, $R^{18}$ is preferably an aliphatic hydrocarbon group, more preferably a branched aliphatic hydrocarbon group, especially preferably an isopropyl group. A plurality of $R^{18}$s may be same or different, and they are preferably the same. When $R^{15}$ to $R^{17}$ and $R^{15'}$ are the groups represented by $*-Si(R^{18})_3$, the macromolecular compound according to the present invention has an increased solubility in an organic solvent.

Specific examples of the groups represented by $*-Si(R^{18})_3$ as $R^{15}$ to $R^{17}$ and $R^{15'}$ in the above formulae (t1) to (t5) include alkylsilyl groups such as trimethylsilyl group, ethyldimethylsilyl group, isopropyldimethylsilyl group, triisopropylsilyl group, tert-butyldimethylsilyl group, triethylsilyl group, triisobutylsilyl group, tripropylsilyl group, tributylsilyl group, dimethylphenylsilyl group and methyldiphenylsilyl group; and arylsilyl groups such as triphenylsilyl group and tert-butylchlorodiphenylsilyl group. Among them, alkylsilyl groups are preferable, and trimethylsilyl group and triisopropylsilyl group are especially preferable.

When $R^{17}$ is a halogen atom in the above formula (t5), any of fluorine, chlorine, bromine and iodine may be used.

$R^{15'}$ is a hydrogen atom, or a group similar to the hydrocarbon group with a carbon number of 6 to 30 as shown as an example of $R^{15}$, or the group represented by $*-Si(R^{18})_3$.

The electron-donating groups of $T^1$ and $T^2$ are each more preferably a group represented by one of the formulae (t1), (t3) and (t5), further preferably a group represented by the formula (t3), especially preferably a group represented by one of the following formulae (t3-1) to (t3-16) from the viewpoint of excellent flatness as the whole of the structural unit represented by the formula (1). In the formulae, * represents a bond.

[Chemical Formula 16]

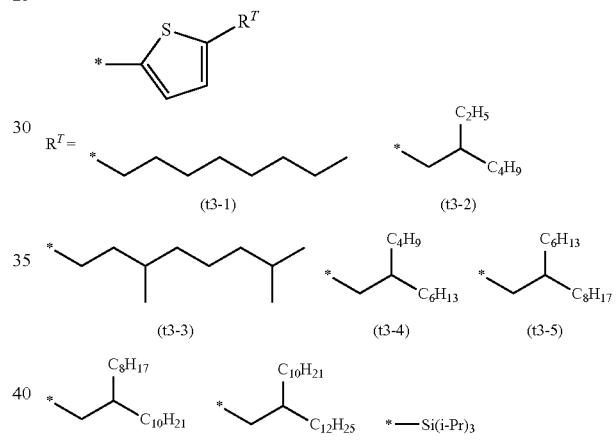

[Chemical Formula 17]

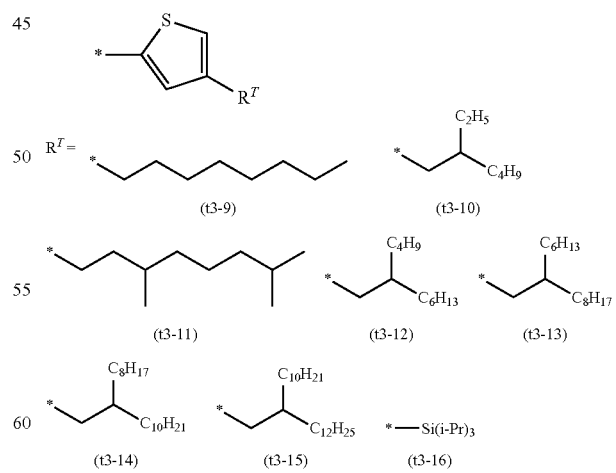

Electron-donating groups or electron-attracting groups may be used as $T^1$ and $T^2$. Examples of the electron-donating group include groups represented by the formulae (t1) to (t3).

[Chemical Formula 18]

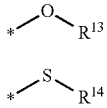  (t1)

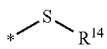  (t2)

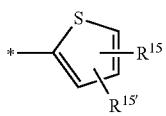  (t3)

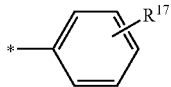  (t5)

[In the formulae (t1) to (t3), * represents a bond, and $R^{13}$ to $R^{15}$ and $R^{15'}$ each represent a group similar to one described above. $R^{17}$s each independently represent a hydrocarbon group with a carbon number of 6 to 30, *—O—$R^{19}$ or *—S—$R^{20}$, and * represents a bond.]

Examples of the electron-attracting group that may be used as $T^1$ and $T^2$ include groups represented by the formulae (t4) to (t5).

[Chemical Formula 19]

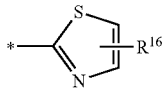  (t4)

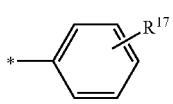  (t5)

[In the formulae (t4) and (t5), $R^{16}$ represents a group similar to one described above, $R^{17}$ represents a halogen atom or a trifluoromethyl group, and * represents a bond.]

In the benzobisthiazole structural unit represented by the formula (1), $B^1$ and $B^2$ may be mutually same or different, and they are preferably the same from the viewpoint of ease of the production. In the structural unit represented by the formula (1), $B^1$ and $B^2$ are each preferably a group represented by any one of the following formulae (b1) to (b3). When $B^1$ and $B^2$ are each a group represented by one of the following formulae (b1) to (b3), the resulting macromolecular compound has proper flatness, so that the photoelectric conversion efficiency can be further improved.

[Chemical Formula 20]

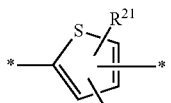  (b1)

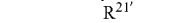  (b2)

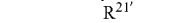  (b3)

[In the formulae (b1) to (b3), $R^{21}$, $R^{22}$ and $R^{21'}$ each represent a hydrogen atom or a hydrocarbon group with a carbon number of 6 to 30. * represents a bond, and in particular, * on the left side represents a bond of a benzobisthiazole compound to a benzene ring.]

As the hydrocarbon groups with a carbon number of 6 to 30 as $R^{21}$, $R^{22}$ and $R^{21'}$, the groups shown as examples of hydrocarbon groups with a carbon number of 6 to 30 as $R^{13}$ to $R^{17}$, $R^{19}$, $R^{20}$ and $R^{15'}$ may be preferably used.

It is preferable that $R^{21}$, $R^{22}$ and $R^{21'}$ are hydrogen atoms in that a donor-acceptor-type semiconductor polymer is easily formed. It is preferable that $R^{21}$, $R^{22}$ and $R^{21'}$ are hydrocarbon groups with a carbon number of 6 to 30 in that the photoelectric conversion efficiency may be further improved.

In the benzobisthiazole structural unit represented by the formula (1), $B^1$ and $B^2$ are each more preferably a group represented by one of the formulae (b1) and (b2) from the viewpoint of excellent flatness as the whole of the structural unit represented by the formula (1) as well as excellent flatness as the whole of the resulting macromolecular compound. When $B^1$ and $B^2$ are each a group represented by one of the formulae (b1) and (b2), the S atom and the N atom interact with each other in the benzobisthiazole structural unit (1), so that flatness is further improved. Specifically, $B^1$ and $B^2$ are each preferably a group represented by one of the following formulae. In the formulae, * represents a bond, and * on the left side represents a bond of benzobisthiazole to a benzene ring.

[Chemical Formula 21]

  (b1-1)

  (b2-1)

  (b3-1)

Examples of the structural unit represented by the formula (1) include groups represented by the following formulae (1-1) to (1-48).

[Chemical Formula 22]

$R^T =$ (1-1) *—CH₂(CH₂)₇CH₃ (n-nonyl chain)

(1-2) 2-ethylhexyl-type: *—CH₂—CH(C₂H₅)(C₄H₉)

(1-3) *—CH₂CH₂CH(CH₃)CH₂CH₂CH₂CH(CH₃)₂

(1-4) *—CH₂—CH(C₄H₉)(C₆H₁₃)

(1-5) *—CH₂—CH(C₆H₁₃)(C₈H₁₇)

(1-6) *—CH₂—CH(C₈H₁₇)(C₁₀H₂₁)

(1-7) *—CH₂—CH(C₁₀H₂₁)(C₂₁H₂₅)

(1-8) *—Si(i-Pr)₃

[Chemical Formula 23]

$R^T =$ (1-9) *—CH₂(CH₂)₇CH₃

(1-10) *—CH₂—CH(C₂H₅)(C₄H₉)

(1-11) *—CH₂CH₂CH(CH₃)CH₂CH₂CH₂CH(CH₃)₂

(1-12) *—CH₂—CH(C₄H₉)(C₆H₁₃)

(1-13) *—CH₂—CH(C₆H₁₃)(C₈H₁₇)

(1-14) *—CH₂—CH(C₈H₁₇)(C₁₀H₂₁)

(1-15) *—CH₂—CH(C₁₀H₂₁)(C₂₁H₂₅)

(1-16) *—Si(i-Pr)₃

[Chemical Formula 24]
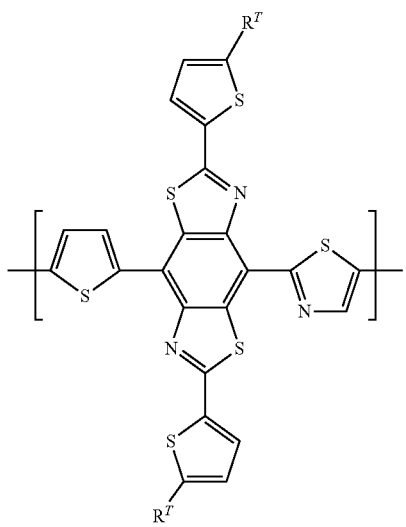
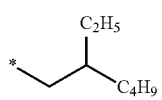 (1-17)
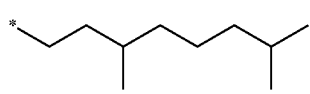 (1-19)
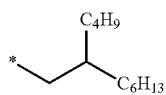 (1-20)
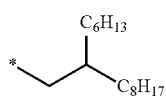 (1-21)
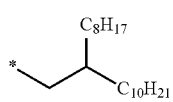 (1-22)
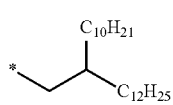 (1-23)
*—Si(i-Pr)$_3$ (1-24)
[Chemical Formula 25]
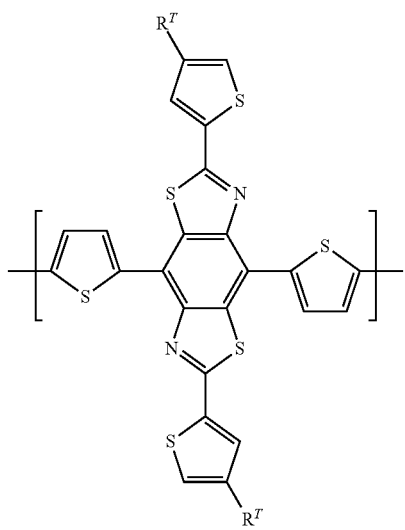
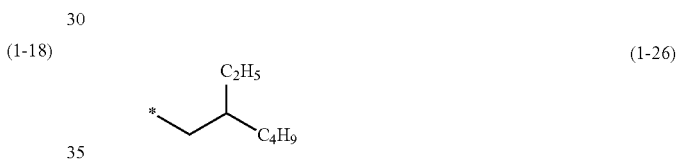
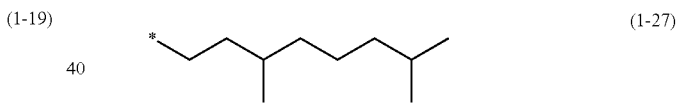
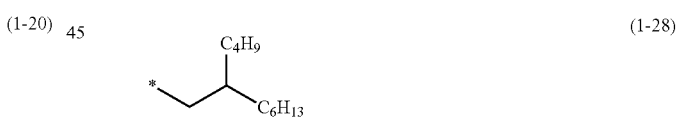
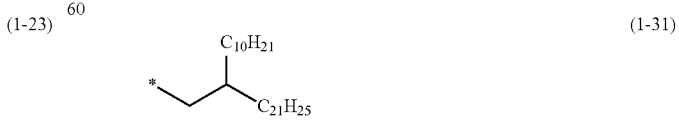

[Chemical Formula 26]

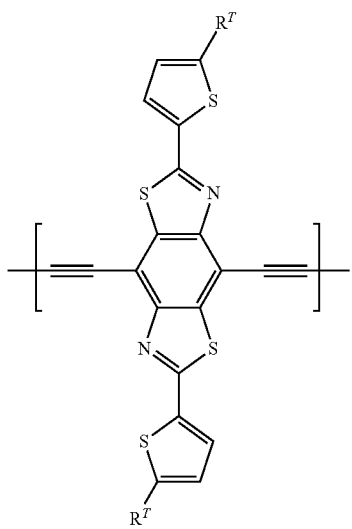

$R^T =$ 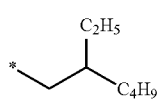 (1-33)

(1-34)

(1-35)

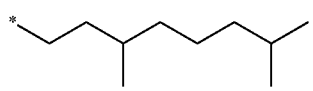 (1-35)

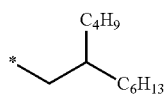 (1-36)

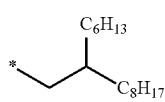 (1-37)

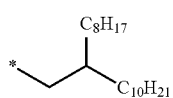 (1-38)

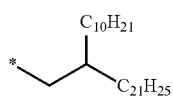 (1-39)

*—Si(i-Pr)$_3$ (1-40)

[Chemical Formula 27]

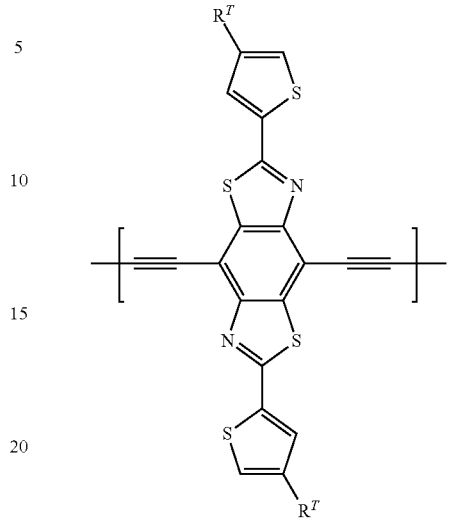

$R^T =$ * ~~~~~~~~~ (1-41)

* C$_2$H$_5$ / C$_4$H$_9$ (1-42)

* ~~~ (1-43)

* C$_4$H$_9$ / C$_6$H$_{13}$ (1-44)

* C$_6$H$_{13}$ / C$_8$H$_{17}$ (1-45)

* C$_8$H$_{17}$ / C$_{10}$H$_{21}$ (1-46)

* C$_{10}$H$_{21}$ / C$_{21}$H$_{25}$ (1-47)

*—Si(i-Pr)$_3$ (1-48)

As a structural unit that is combined with a structural unit represented by the formula (1) to form a donor-acceptor-type semiconductor polymer (donor unit or acceptor unit), a previously known structural unit may be used. Specific examples thereof may include the following structural units.

[Chemical Formula 28]
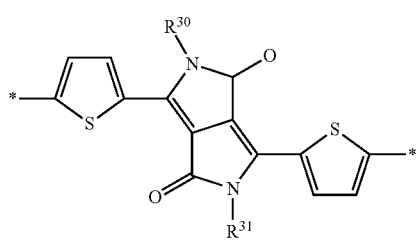
(c1)
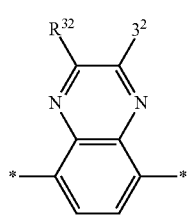
(c2)
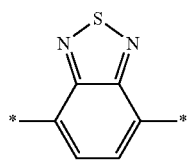
(c3)
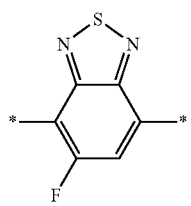
(c4)
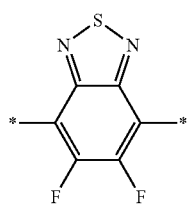
(c5)
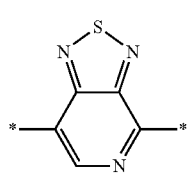
(c6)
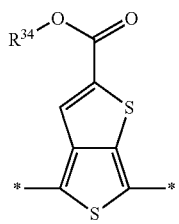
(c7)
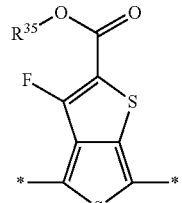
(c8)
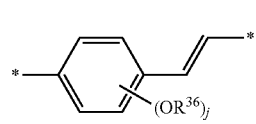
(c9)
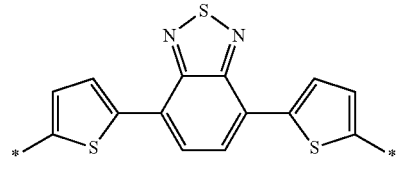
(c10)
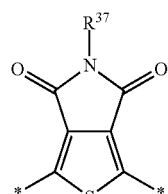
(c11)
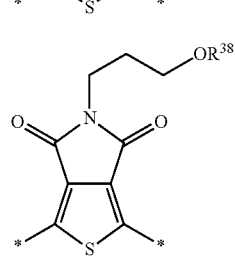
(c12)
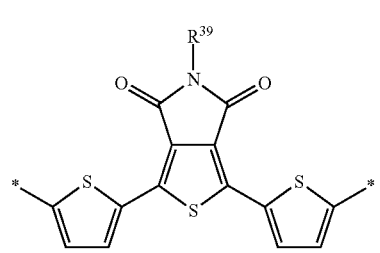
(c13)
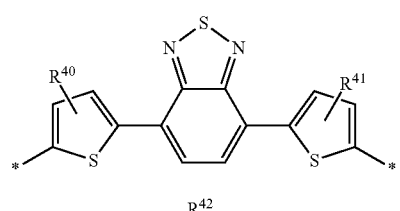
(c14)
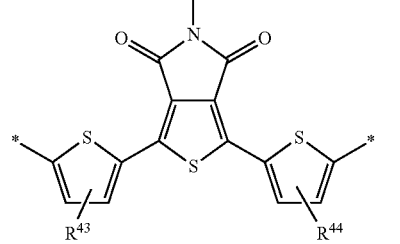
(c15)

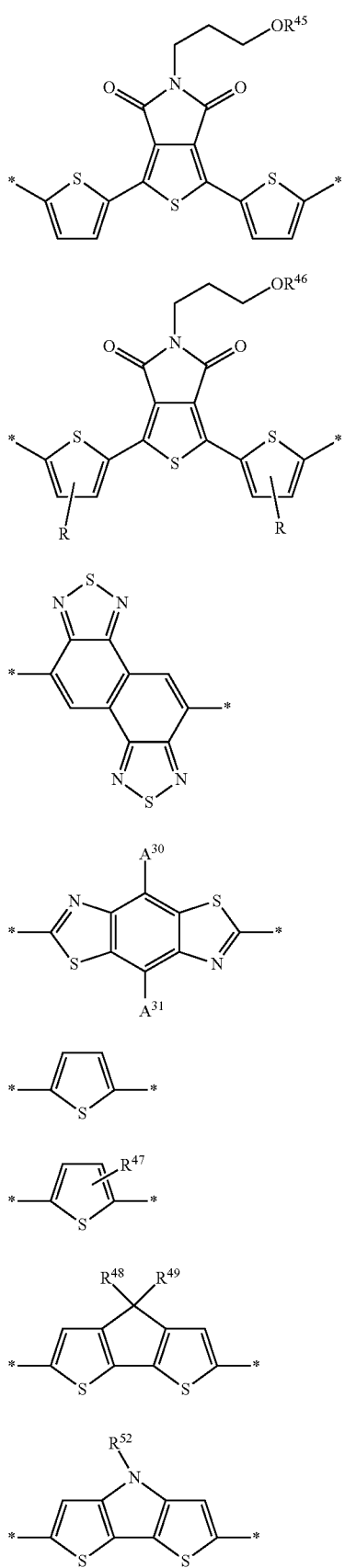
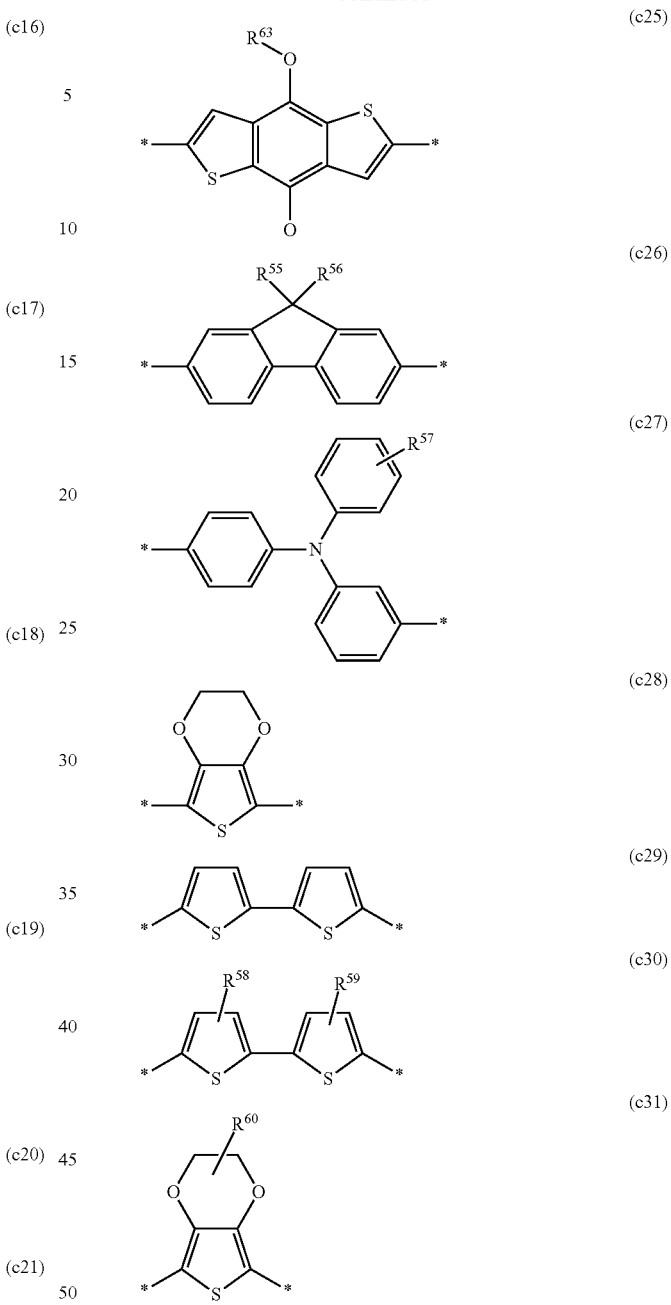

[In the formulae (c1) to (c31), $R^{30}$ to $R^{60}$ each independently represent a group similar to the hydrocarbon groups with a carbon number of 6 to 30 as $R^{13}$ to $R^{17}$, $R^{19}$, $R^{20}$ and $R^{15'}$, and $A^{30}$ and $A^{31}$ each independently represent a group similar to $T^1$ and $T^2$.]

The groups represented by the above formulae (c1) to (c18) are groups which serve as an acceptor unit, and the groups represented by the formulae (c20) to (c31) are groups which serve as a donor unit. The group represented by the formula (c19) may serve as an acceptor unit or serve as a donor unit depending on the type of $A^{30}$ and $A^{31}$.

The weight average molecular weight and number average molecular weight of the macromolecular compound according to the present invention are generally not less than 2,000 and not more than 500,000, more preferably not less than 3,000 and not more than 200,000. The weight average molecular weight and number average molecular weight of the macromolecular compound according to the present invention can be calculated based on a calibration curve prepared with polystyrene as a standard sample using gel permeation chromatography.

The ionization potential of the macromolecular compound according to the present invention is preferably 4 eV or more, more preferably 4.5 eV or more, further preferably 5 eV or more, especially preferably 5.1 eV or more. While the upper limit of the ionization potential is not particularly limited, it is, for example, 7 eV or less, preferably 6.5 eV or less, more preferably 6.2 eV or less. When the ionization potential of the macromolecular compound according to the present invention is in the above-mentioned range, the HOMO level is moderately deepened (lowered), and therefore both a high open circuit voltage (Voc) and a high short-circuit current density (Jsc) can be achieved, so that a higher photoelectric conversion efficiency can be achieved.

2. Compound 2-1. (Compound Represented by Formula (5))

The present invention includes a compound represented by the following formula (5) (hereinafter, sometimes referred to as a "compound (5)").

[Chemical Formula 29]

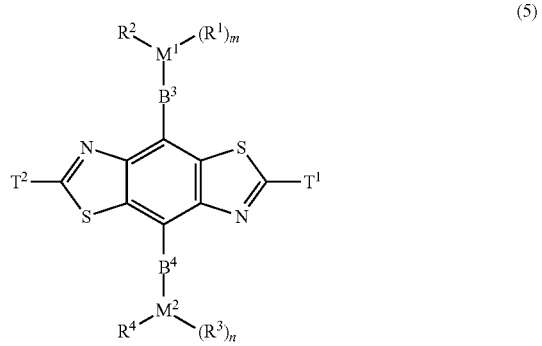

(5)

[in the formula (5), $T^1$ and $T^2$ each independently represent an alkoxy group, a thioalkoxy group, a thiophene ring optionally substituted by a hydrocarbon group or an organosilyl group, a thiazole ring optionally substituted by a hydrocarbon group or an organosilyl group, or a phenyl group optionally substituted by a hydrocarbon group, an alkoxy group, a thioalkoxy group, an organosilyl group, a halogen atom or a trifluoromethyl group; $B^3$ and $B^4$ represent a thiophene ring optionally substituted by an alkyl group, or a thiazole ring optionally substituted by an alkyl group; $R^1$ to $R^4$ each independently represent an aliphatic hydrocarbon group with a carbon number of 1 to 6, hydroxyl group, an alkoxy group with a carbon number of 1 to 6, or an aryloxy group with a carbon number of 6 to 10; $M^1$ and $M^2$ each independently represent a boron atom or a tin atom; $R^1$ and $R^2$ may form a ring with $M^1$, $R^3$ and $R^4$ may form a ring with $M^2$; and m and n each represent an integer of 1 or 2, and when m and n each represent 2, a plurality of $R^1$s and a plurality of $R^3$s may be each same or different].

In the formula (5), $B^3$ and $B^4$ may be mutually same or different, and they are preferably the same from the viewpoint of ease of production. In the formula (5), $B^3$ and $B^4$ are each preferably a group represented by one of the above formulae (b1) and (b2).

In the formula (5), the carbon number of the aliphatic hydrocarbon groups of $R^1$ to $R^4$ is preferably 1 to 5, more preferably 1 to 4. The aliphatic hydrocarbon groups of $R^1$ to $R^4$ are each preferably methyl group, ethyl group, propyl group or butyl group, more preferably methyl group or butyl group. The carbon number of the alkoxy groups of $R^1$ to $R^4$ is preferably 1 to 3, more preferably 1 or 2. The alkoxy groups of $R^1$ to $R^4$ are each preferably methoxy group, ethoxy group, propoxy group or the like, more preferably methoxy group or ethoxy group. The carbon number of the aryloxy groups of $R^1$ to $R^4$ is preferably 6 to 9, more preferably 6 to 8. Examples of the aryloxy groups of $R^1$ to $R^4$ include phenyloxy group, benzyloxy group and phenylenebis(methyleneoxy) group.

When $M^1$ and $M^2$ are boron atoms, $R^1$ to $R^4$ are each preferably hydroxyl group, an alkoxy group with a carbon number of 1 to 6, or an aryloxy group with a carbon number of 6 to 10, and m and n are each preferably 1. When $M^1$ and $M^2$ are boron atoms, examples of $*-M^1(R^1)_m R^2$ and $*-M^2(R^3)_n R^4$ include groups represented by the following formulae. * represents a bond.

[Chemical Formula 30]

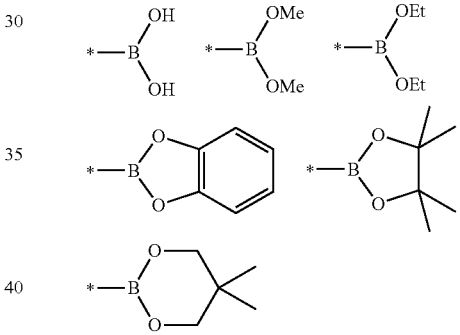

When $M^1$ and $M^2$ are tin atoms, $R^1$ to $R^4$ are each preferably an aliphatic hydrocarbon group with a carbon number of 1 to 6, m and n are each preferably 2. When $M^1$ and $M^2$ are tin atoms, examples of $*-M^1(R^1)_m R^2$ and $*-M^2(R^3)_n R^4$ include groups represented by the following formulae. * represents a bond.

*—Sn(Me)$_3$ *—Sn(Bu)$_3$   [Chemical Formula 31]

The compound (5) is an intermediate compound to be used for synthesis of the macromolecular compound according to the present invention. Since the compound (5) has the predetermined group described above, it has high temporal stability, and can efficiently react to form the macromolecular compound according to the present invention. Examples of the compound (5) may include compounds represented by the following formulae. The compounds represented by the formulae (5-33) to (5-64) in which a methyl group on a tin atom is substituted with a butyl group in the formulae (5-1) to (5-32) may be shown as preferred examples of the compound (5).

[Chemical Formula 32]
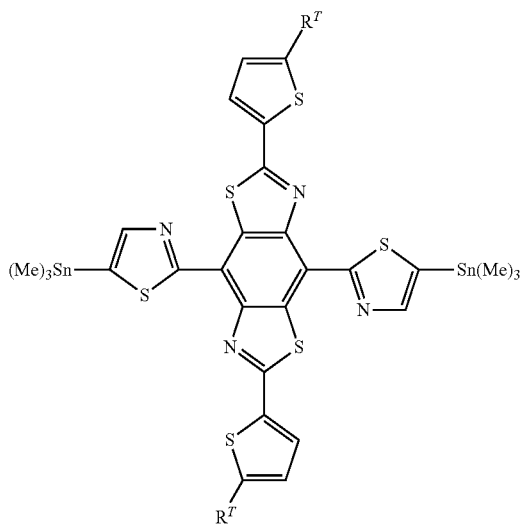
 (5-1)
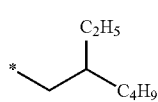 (5-2)
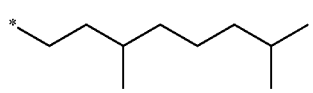 (5-3)
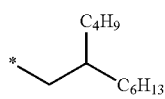 (5-4)
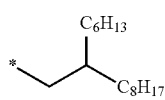 (5-5)
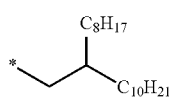 (5-6)
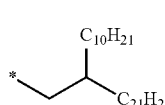 (5-7)
*—Si(i-Pr)₃ (5-8)
[Chemical Formula 33]
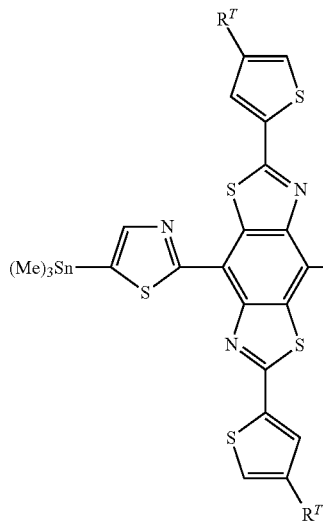
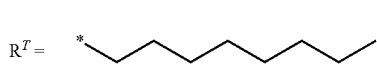 (5-9)
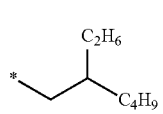 (5-10)
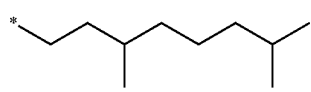 (5-11)
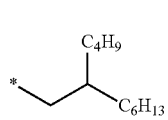 (5-12)
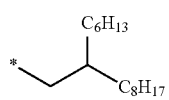 (5-13)
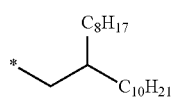 (5-14)
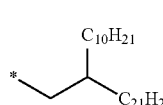 (5-15)
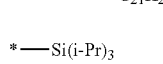 *—Si(i-Pr)₃ (5-16)

-continued
[Chemical Formula 34]
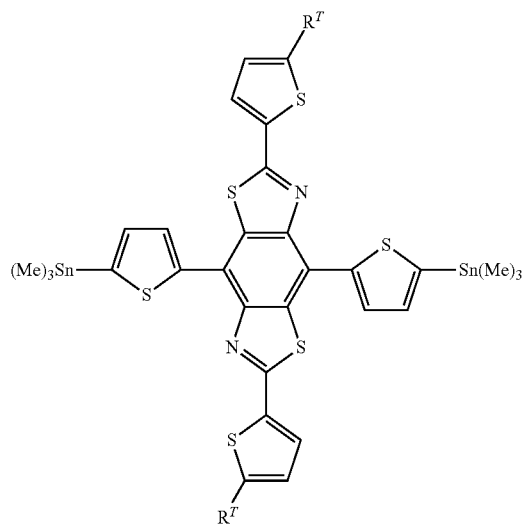
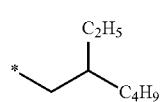 (5-17)
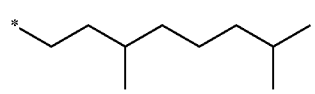 (5-19)
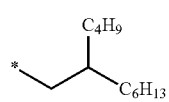 (5-20)
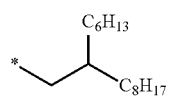 (5-21)
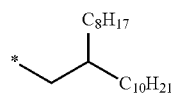 (5-22)
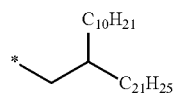 (5-23)
*—Si(i-Pr)$_3$ (5-24)
-continued
[Chemical Formula 35]
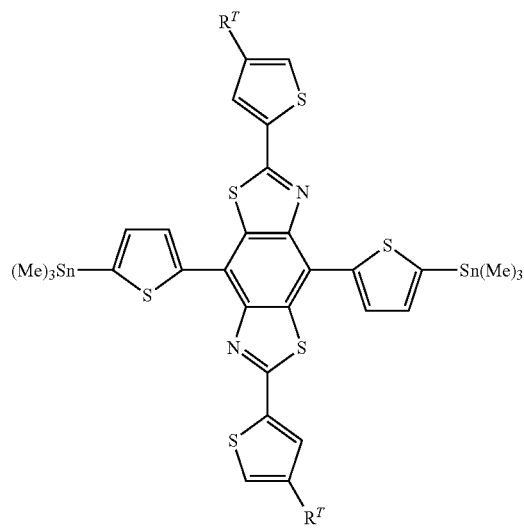
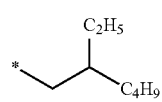 (5-25)
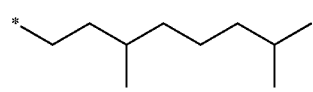 (5-27)
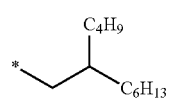 (5-28)
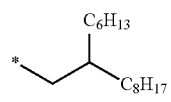 (5-29)
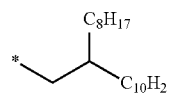 (5-30)
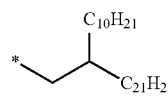 (5-31)
*—Si(i-Pr)$_3$ (5-32)
(5-18) structure with C$_2$H$_5$ and C$_4$H$_9$
(5-26) structure with C$_2$H$_5$ and C$_4$H$_9$

[Chemical Formula 36]
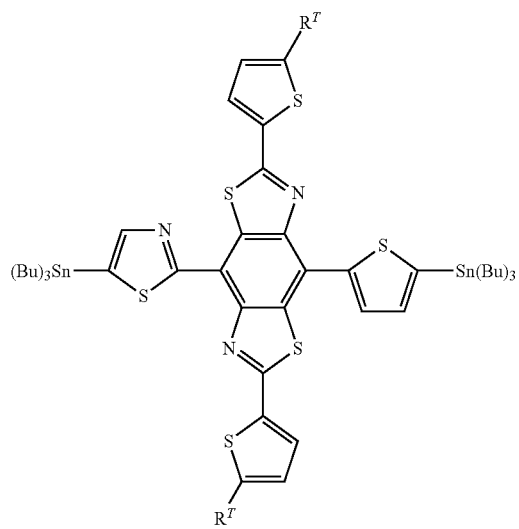
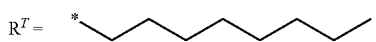 (5-33)
(5-34)
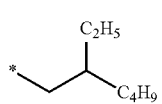
(5-35)
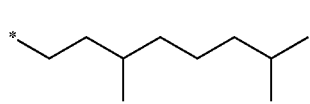
(5-36)
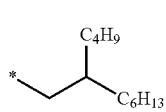
(5-37)
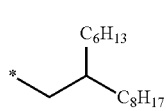
(5-38)
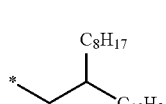
(5-39)
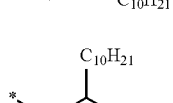
(5-40) *—Si(i-Pr)$_3$
[Chemical Formula 37]
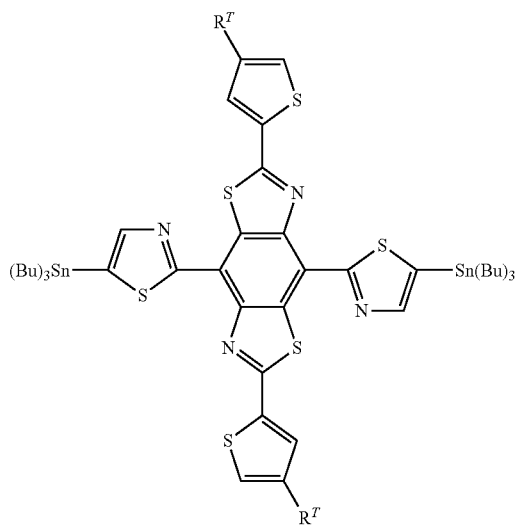
R$^T$ = 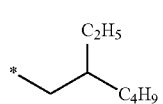 (5-41)
(5-42)
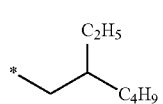
(5-43)
(5-44)
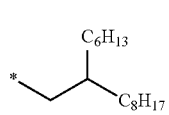
(5-45)
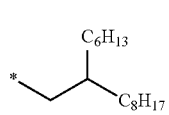
(5-46)
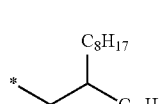
(5-47)
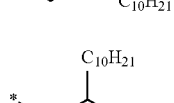
(5-48) *—Si(i-Pr)$_3$

[Chemical Formula 38]
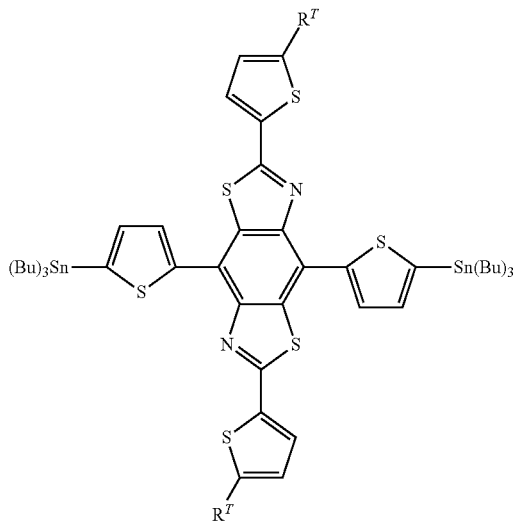
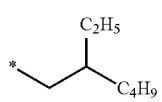 (5-49)
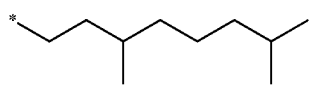 (5-50)
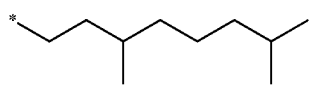 (5-51)
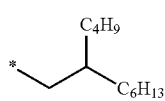 (5-52)
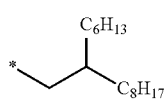 (5-53)
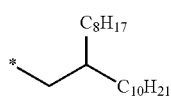 (5-54)
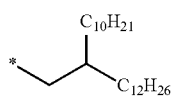 (5-55)
*—Si(i-Pr)$_3$ (5-56)
[Chemical Formula 39]
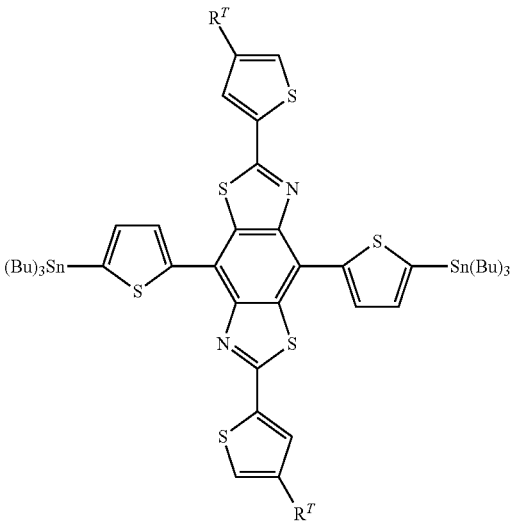
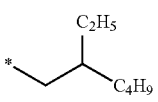 (5-57)
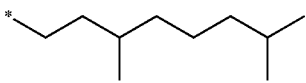 (5-58)
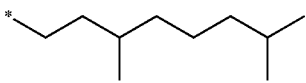 (5-59)
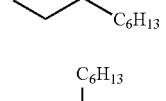 (5-60)
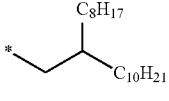 (5-61)
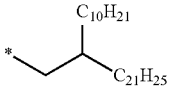 (5-62)
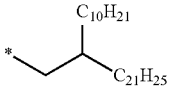 (5-63)
*—Si(i-Pr)$_3$ (5-64)
2-2. Compound Represented by Formula (4)
The present invention includes a compound represented by the following formula (4) (hereinafter, sometimes referred to as a "compound (4)").

[Chemical Formula 40]

(4)

[In the formula (4), $T^1$, $T^2$, $B^1$ and $B^2$ each represent a group similar to one described above.]

The compound (4) is a raw material for the compound (5). In other words, the compound (4) is an intermediate of the compound (5). Since the compound (4) has the predetermined group described above, it has high temporal stability, and efficient reactivity. Examples of the compound (4) may include the following compounds.

[Chemical Formula 41]

$R^T =$ (4-1)

(4-2)

(4-3)

(4-4)

(4-5)

(4-6)

(4-7)

*—Si(i-Pr)$_3$ (4-8)

[Chemical Formula 42]

$R^T =$ (4-9)

(4-10)

(4-11)

(4-12)

(4-13)

(4-14)

(4-15)

*—Si(i-Pr)$_3$ (4-16)

[Chemical Formula 43]
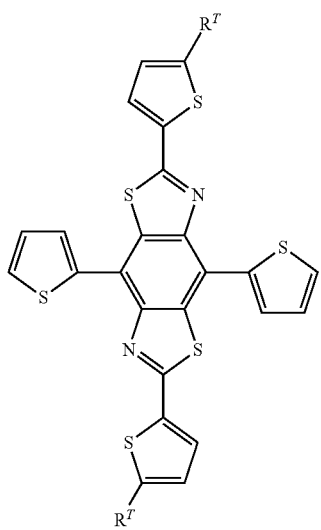
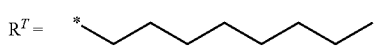 (4-17)
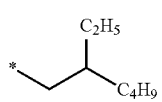 (4-18)
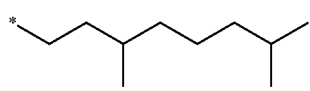 (4-19)
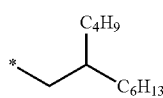 (4-20)
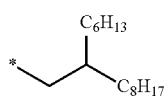 (4-21)
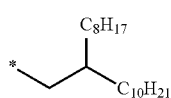 (4-22)
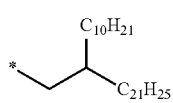 (4-23)
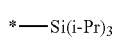 (4-24)
[Chemical Formula 44]
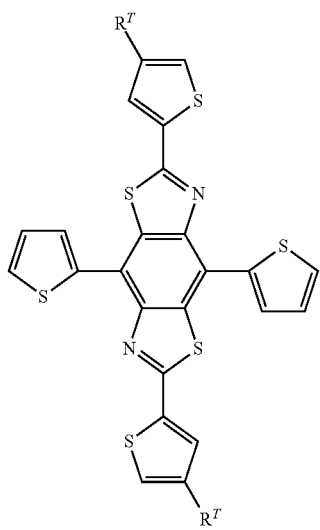
 (4-25)
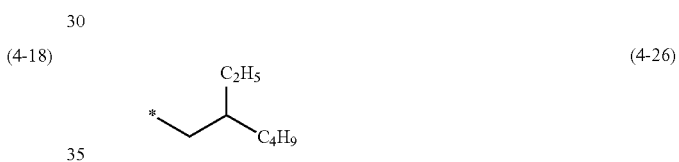 (4-26)
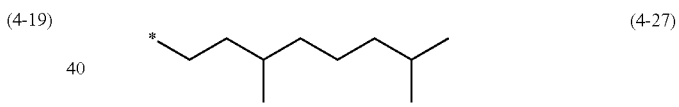 (4-27)
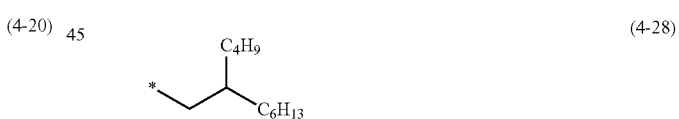 (4-28)
 (4-29)
 (4-30)
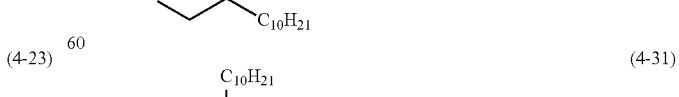 (4-31)
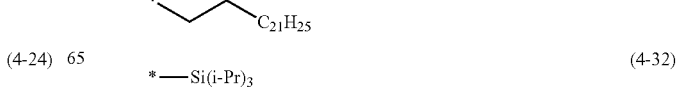 (4-32)

[Chemical Formula 45]

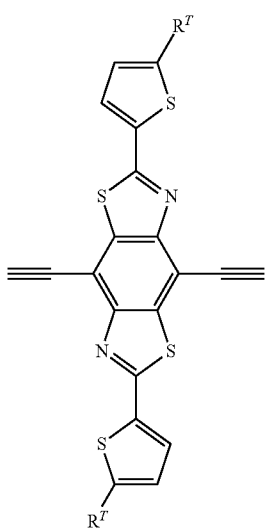

R$^T$ = 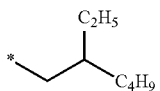 (4-33)

(C$_2$H$_5$, C$_4$H$_9$ branched) (4-34)

(branched alkyl) (4-35)

(C$_4$H$_9$, C$_6$H$_{13}$ branched) (4-36)

(C$_6$H$_{13}$, C$_8$H$_{17}$ branched) (4-37)

(C$_8$H$_{17}$, C$_{10}$H$_{21}$ branched) (4-38)

(C$_{10}$H$_{21}$, C$_{21}$H$_{25}$ branched) (4-39)

*—Si(i-Pr)$_3$ (4-40)

[Chemical Formula 46]

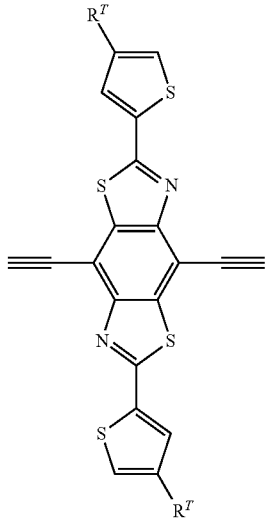

R$^T$ = (n-alkyl) (4-41)

(C$_2$H$_5$, C$_4$H$_9$ branched) (4-42)

(branched alkyl) (4-43)

(C$_4$H$_9$, C$_6$H$_{13}$ branched) (4-44)

(C$_6$H$_{13}$, C$_8$H$_{17}$ branched) (4-45)

(C$_8$H$_{17}$, C$_{10}$H$_{21}$ branched) (4-46)

(C$_{10}$H$_{21}$, C$_{21}$H$_{25}$ branched) (4-47)

*—Si(i-Pr)$_3$ (4-48)

2-3. Compound Represented by Formula (3)

The present invention includes a compound represented by the following formula (3) (hereinafter, sometimes referred to as a "compound (3)").

[Chemical Formula 47]

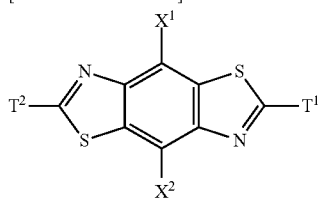
(3)

[In the formula (3), $T^1$, $T^2$, $X^1$ and $X^2$ each represent a group similar to one described above.]

Examples of the halogen atom of X include chlorine, bromine and iodine. While any of these halogen atoms may be used, iodine is especially preferable from the viewpoint of the balance between reactivity and stability.

The compound (3) is a raw material for the compound (4). In other words, the compound (3) is an intermediate of the compound (6). Since the compound (3) has the predetermined group described above, it has high temporal stability, and has a high solubility in an organic solvent, and hence efficient reactivity. Further, by using the compound (3), a variety of backbones and substituents can be introduced into the macromolecular compound according to the present invention. Examples of the compound (3) may include the following compounds.

[Chemical Formula 48]

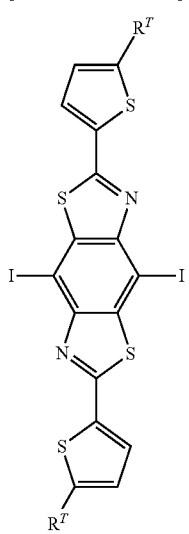

$R^T=$

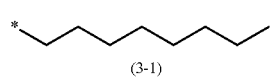  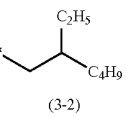
(3-1) (3-2)

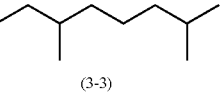  
(3-3) (3-4)

  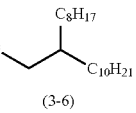
(3-5) (3-6)

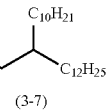  *—Si(i-Pr)$_3$
(3-7)   (3-8)

[Chemical Formula 49]

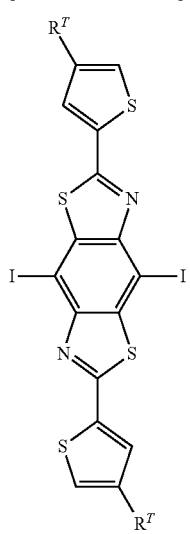

$R^T=$

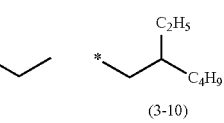
(3-9) (3-10)

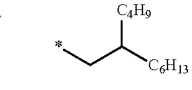
(3-11) (3-12)

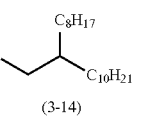
(3-13) (3-14)

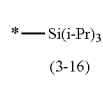  *—Si(i-Pr)$_3$
(3-15)   (3-16)

In the production method according to the present invention, a compound represented by the following formula (3') (hereinafter, sometimes referred to as a "compound (3')") is also generated. By using the compound (3'), a compound substituted with a group represented by $B^1$ or $B^2$ at only one of two substitutable positions present on the benzene ring of benzobisthiazole can be obtained. The compound is useful as, for example, an end part of the macromolecular compound according to the present invention.

[Chemical Formula 50]

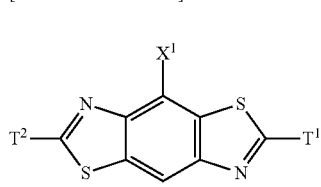
(3')

[In the formula (3'), $T^1$, $T^2$ and $X^1$ each represent a group similar to one described above.]

Examples of the compound (3') may include compounds represented by the following formulae.

[Chemical Formula 51]

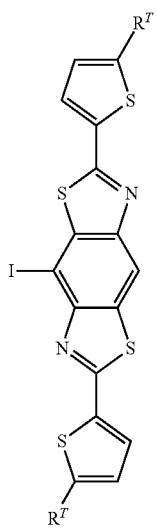

[Chemical Formula 52]

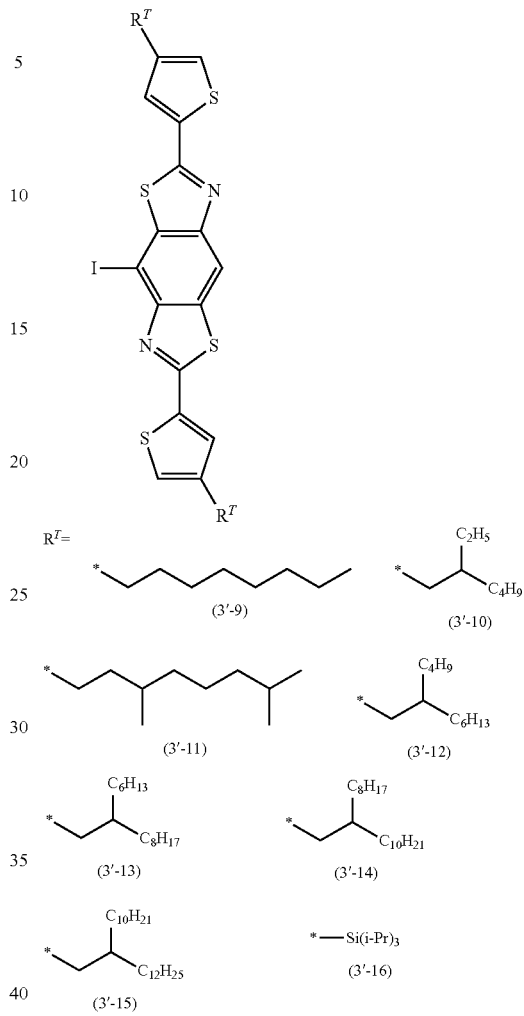

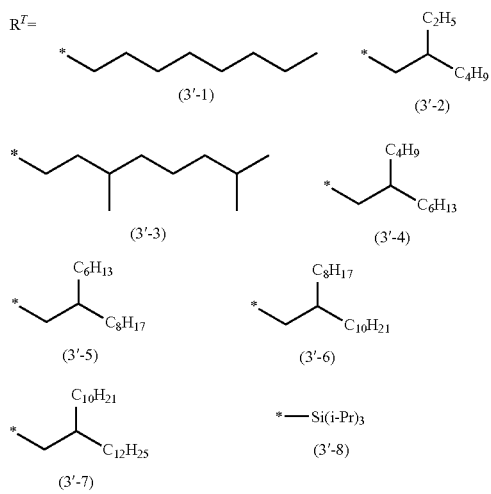

2-4. Compound Represented by Formula (2)

The present invention includes a compound represented by the following formula (2) (hereinafter, sometimes referred to as a "compound (2)").

[Chemical Formula 53]

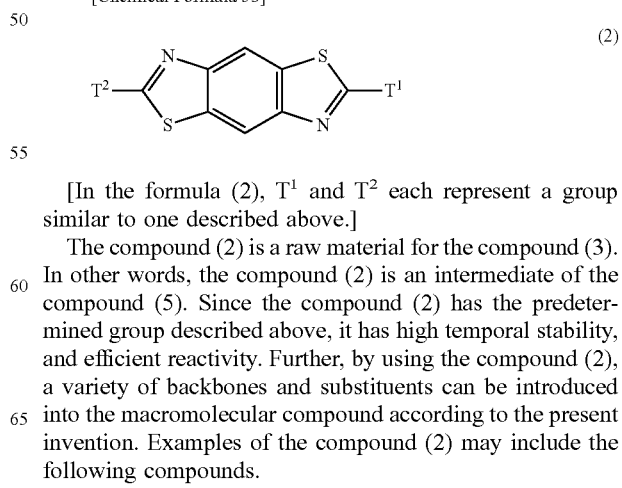

[In the formula (2), $T^1$ and $T^2$ each represent a group similar to one described above.]

The compound (2) is a raw material for the compound (3). In other words, the compound (2) is an intermediate of the compound (5). Since the compound (2) has the predetermined group described above, it has high temporal stability, and efficient reactivity. Further, by using the compound (2), a variety of backbones and substituents can be introduced into the macromolecular compound according to the present invention. Examples of the compound (2) may include the following compounds.

[Chemical Formula 54]

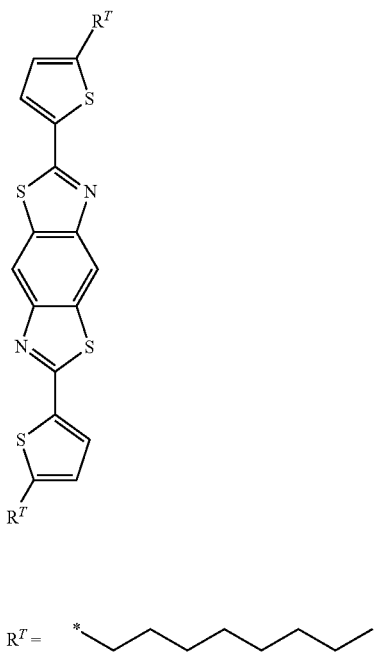

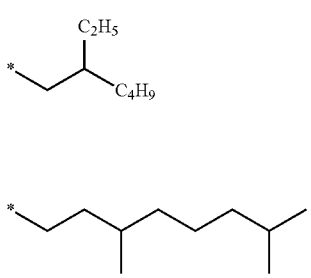 (2-1)

(2-2)

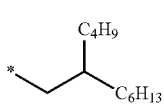 (2-3)

(2-4)

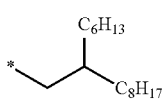 (2-5)

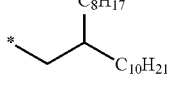 (2-6)

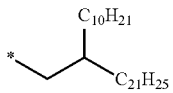 (2-7)

(2-8)

*—Si(i-Pr)₃

[Chemical Formula 55]

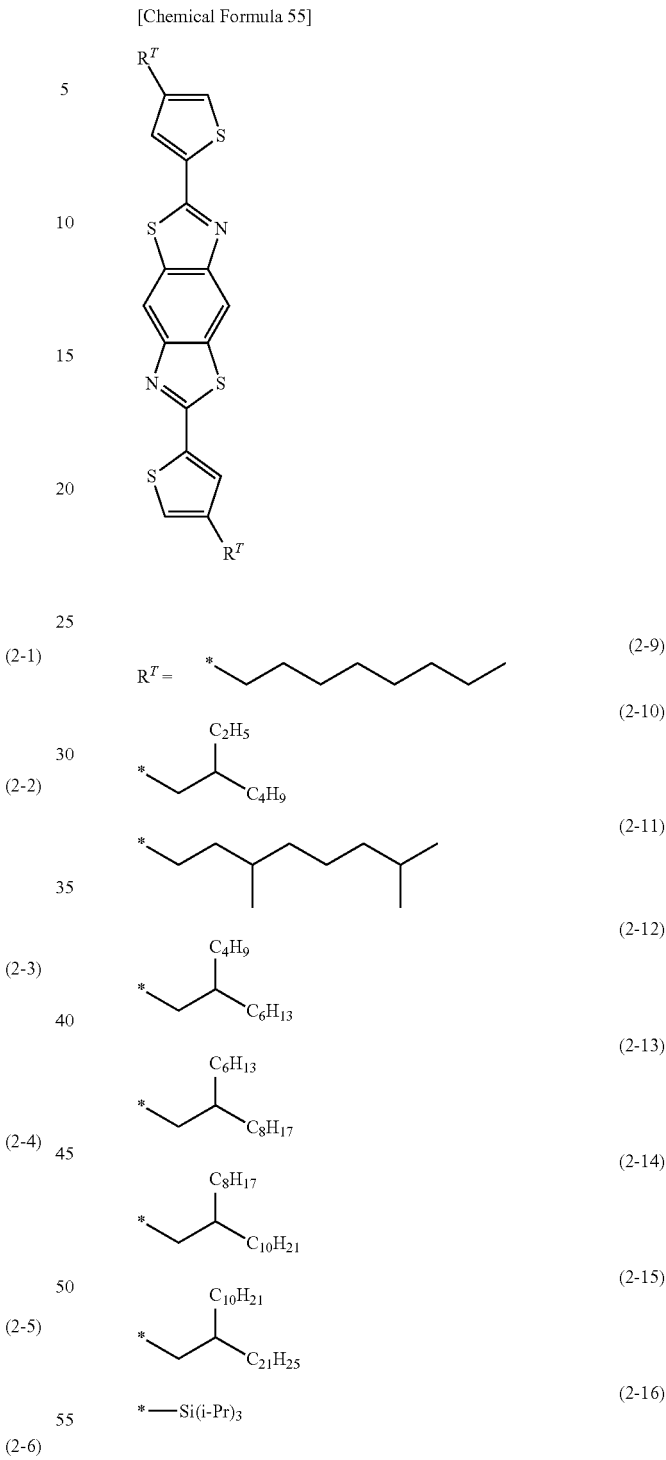

3. Production Method

The macromolecular compound represented by the formula (1) according to the present invention is produced by a production method which includes:

using a compound selected from the group consisting of 2,6-diiodobenzo[1,2-d:4,5-d']bisthiazole and 2,6-dibromobenzo[1,2-d:4,5-d']bisthiazole as a starting material; and going through a compound represented by the formula (2):

[Chemical Formula 56]

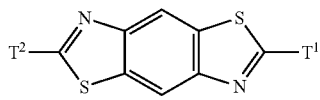

(2)

[in the formula (2), $T^1$ and $T^2$ each represent a group similar to one described above];

a compound represented by the formula (3):

[Chemical Formula 57]

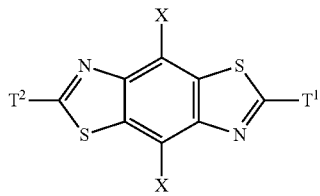

(3)

[in the formula (3), $T^1$, $T^2$, $X^1$ and $X^2$ each represent a group similar to one described above]; and a compound represented by the formula (4):

[Chemical Formula 58]

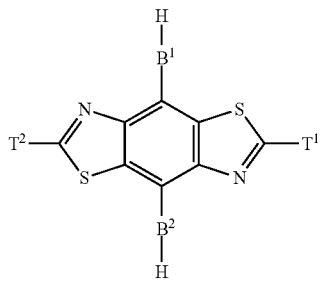

(4)

[in the formula (4), $T^1$, $T^2$, $B^1$ and B2 each represent a group similar to one described above].

Preferably, the method for producing the macromolecular compound according to the present invention further includes going through a compound represented by the formula (5):

[Chemical Formula 59]

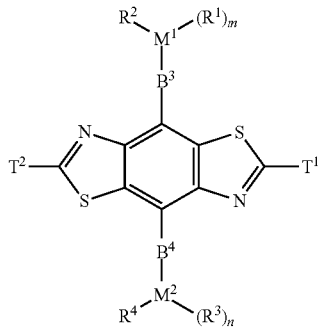

(5)

[in the formula (5), $T^1$, $T^2$, $B^3$, $B^4$, $R^1$ to $R^4$, $M^1$, $M^2$, m and n each represent a group similar to one described above].

According to the production method according to the present invention, a variety of substituents can be introduced into a benzobisthiazole backbone, leading to material design with a high degree of freedom. As a result, the properties of a material (e.g. energy level, solubility, crystallinity, film formability and absorption wavelength) can be easily controlled.

3-1. First Step

Preferably, the production method according to the present invention comprises the following first step.

First step: a step of reacting a compound represented by the formula (6) and/or formula (7):

[Chemical Formula 60]

$$T^1\text{-}R^5 \qquad (6)$$

$$T^2\text{-}R^6 \qquad (7)$$

[in the formulae (6) and (7), $T^1$ and $T^2$ each represent a group similar to one described above; $R^5$ and $R^6$ each independently represent a hydrogen atom or *-$M^3(R^7)_k R^8$; $R^7$ and $R^8$ each independently represent an aliphatic hydrocarbon group with a carbon number of 1 to 6, hydroxyl group, an alkoxy group with a carbon number of 1 to 6, or an aryloxy group with a carbon number of 6 to 10; $M^3$ represents boron atom or tin atom; * represents a bond; $R^7$ and $R^8$ may form a ring with $M^3$; k represents an integer of 1 or 2; and when k is 2, a plurality of $R^7$s may be each same or different]

with a compound selected from the group consisting of 2,6-diiodobenzo[1,2-d:4,5-d']bisthiazole and 2,6-dibromobenzo[1,2-d:4,5-d']bisthiazole in the presence of a metal catalyst to prepare a compound represented by the formula (2).

In the first step, the compound (hereinafter, sometimes referred to as "2,6-dihalogenated benzobisthiazole") selected from the group consisting of 2,6-diiodobenzo[1,2-d:4,5-d']bisthiazole and 2,6-dibromobenzo[1,2-d:4,5-d'] bisthiazole is preferably 2,6-diiodobenzo[1,2-d:4,5-d'] bisthiazole.

The compound represented by the formula (6) and/or formula (7) (hereinafter, sometimes referred to as a "compound (6)" and/or "compound (7)"), which is reacted with 2,6-dihaloganated benzobisthiazole, is preferably a compound in which $T^1$ and $T^2$ are each a group similar to one described above, and $R^5$ and $R^6$ are each a hydrogen atom or *-$M^3(R^7)_k R^8$. * represents a bond.

When $R^5$ and $R^6$ each represent *-$M^3(R^7)_k R^8$, the carbon number of the aliphatic hydrocarbon groups of $R^7$ and $R^8$ is preferably 1 to 5, more preferably 1 to 4. Examples of the aliphatic hydrocarbon groups of $R^7$ and $R^8$ include methyl group, ethyl group, propyl group and butyl group. The carbon number of $R^7$ and $R^8$ is preferably 1 to 3, more preferably 1 or 2. The alkoxy groups of $R^7$ and $R^8$ are each preferably methoxy group, ethoxy group, propoxy group or the like, more preferably methoxy group or ethoxy group. The carbon number of the aryloxy groups of $R^7$ and $R^8$ is preferably 6 to 9, more preferably 6 to 8. Examples of the aryloxy groups of $R^7$ and $R^8$ include phenyloxy group, benzyloxy group and phenylenebis(methyleneoxy) group.

When $R^5$ and $R^6$ are *-$M^3(R^7)_k R^8$, and $M^3$ is a boron atom, $R^7$ and $R^8$ are each preferably hydroxyl group, an alkoxy group with a carbon number of 1 to 6, or an aryloxy group with a carbon number of 6 to 10, and k is preferably 1. When $M^3$ is a boron atom, examples of *-$M^3(R^7)_kR^8$ include groups represented by the following formulae. * represents a bond.

[Chemical Formula 61]

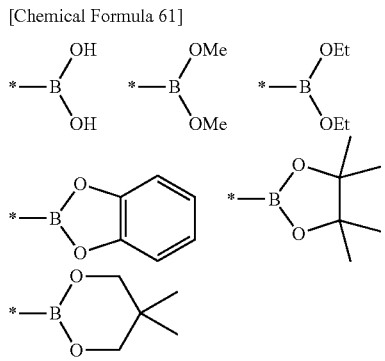

When $R^5$ and $R^6$ are *-$M^3(R^7)_kR^8$, and $M^3$ is tin atom, $R^7$ and $R^8$ are each preferably an aliphatic hydrocarbon group with a carbon number of 1 to 6, and k is preferably 2. When $M^3$ is tin atom, examples of *-$M^3(R^7)_kR^8$ include groups represented by the following formulae. * represents a bond.

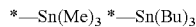 [Chemical Formula 62]

$R^5$ and $R^6$ may be appropriately selected according to the type of $T^1$ and $T^2$. For example, when $T^1$ and $T^2$ are each a group represented by one of the formulae (t1) and (t2), $R^5$ and $R^6$ are each preferably a hydrogen atom. When $T^1$ and $T^2$ are each a group represented by one of the formulae (t3) to (t5), $R^5$ and $R^6$ are each preferably a group represented by *-$M^3(R^7)_kR^8$, more preferably a group represented by *—$Sn(R^7)_2R^8$.

Examples of the compounds (6) and (7) include compounds represented by the following formulae.

[Chemical Formula 63]

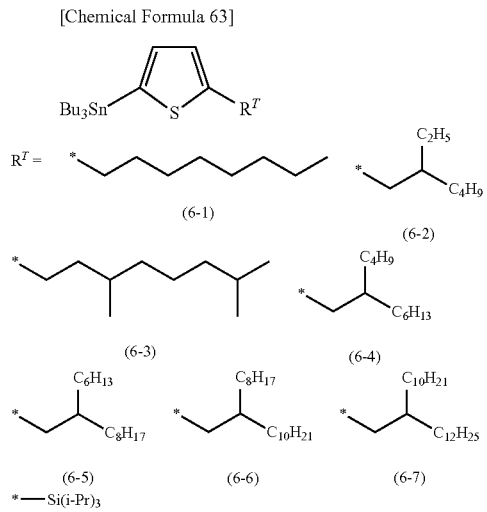

[Chemical Formula 64]

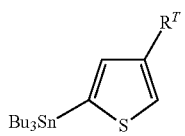

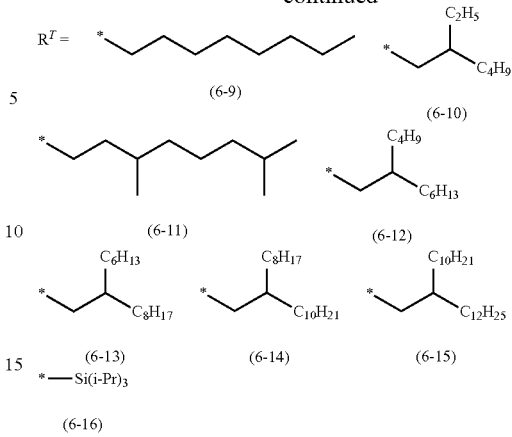

The compounds (6) and (7) may be same or different depending on an intended compound, and they are preferably the same for suppressing generation of byproducts.

In the first step, the molar ratio of 2,6-dihalogenated benzobisthiazole and the total of the compounds (6) and (7) (2,6-dihalogenated benzobisthiazole:total of compounds (6) and (7)) is not particularly limited, and is generally about 1:1 to 1:10, and it is preferably 1:1.5 to 1:8, more preferably 1:2 to 1:6, further preferably 1:2 to 1:5 from the viewpoint of the yield and reaction efficiency.

Examples of the metal catalyst to be used in the reaction of 2,6-dihalogenated benzobisthiazole with the compound (6) and/or compound (7) in the first step include transition metal catalysts such as palladium-based catalysts, nickel-based catalysts, iron-based catalysts, copper-based catalysts, rhodium-based catalysts and ruthenium-based catalysts. Among them, copper-based catalysts and palladium-based catalysts are preferable.

The valence number of palladium is not particularly limited, and palladium may be zero-valent or divalent.

Examples of the palladium-based catalyst include palladium chloride (II), palladium bromide (II), palladium iodide (II), palladium oxide (II), palladium sulfide (II), palladium telluride (II), palladium hydroxide (II), palladium selenide (II), palladium cyanide (II), palladium acetate (II), palladium trifluoroacetate (II), palladium acetylacetonate (II), diacetatebis(triphenylphosphine)palladium (II), tetrakis(triphenylphosphine)palladium (0), dichlorobis(triphenylphosphine)palladium (II), dichlorobis(acetonitrile)palladium (II), dichlorobis(benzonitrile)palladium (II), dichloro[1,2-bis(diphenylphosphino)ethane]palladium (II), dichloro[1,3-bis(diphenylphosphino)propane]palladium (II), dichloro[1,4-bis(diphenylphosphino)butane]palladium (II), dichloro[1,1-bis(diphenylphosphinoferrocene)]palladium (II), dichloro[1,1-bis(diphenylphosphino)ferrocene]palladium (II) dichloromethane adducts, bis(dibenzylideneacetone)palladium (0), tris(dibenzylideneacetone)dipalladium (0), tris(dibenzylideneacetone)dipalladium (0) chloroform adducts, dichloro[1,3-bis(2,6-diisopropylphenyl)imidazole-2-ylidene](3-chloropyridyl)palladium (II), bis(tri-tert-butylphosphine)palladium (0), dichloro[2,5-norbornadiene]palladium (II), dichlorobis(ethylenediamine)palladium (II), dichloro(1,5-cyclooctadiene)palladium (I) and dichlorobis(methyldiphenylphosphine)palladium (II). One of these catalysts may be used alone, or two or more of these catalysts may be used in combination.

Examples of the copper-based catalyst include copper, copper halide compounds such as copper fluoride (I), copper chloride (I), copper bromide (I), copper iodide (I), copper fluoride (II), copper chloride (II), copper bromide (II) and copper iodide (II); copper oxide (I), copper sulfide (I), copper oxide (II), copper sulfide (II), copper acetate (I), copper acetate (II) and copper sulfate (II).

The metal catalyst may be appropriately selected according to the type of $T^1$ and $T^2$, and when $T^1$ and $T^2$ are each a group represented by one of the formulae (t1) and (t2) in the formulae (6) and (7), the metal catalyst is preferably a copper-based catalyst, more preferably a copper halide compound, most preferably copper iodide (I). Preferably, a base coexists. When $T^1$ and $T^2$ are each a group represented by one of the formulae (t3) to (t5) in the formulae (6) and (7), the metal catalyst is preferably a palladium-based catalyst, especially preferably dichlorobis(triphenylphosphine)palladium (II), tris(dibenzylideneacetone)dipalladium (0) or a tris(dibenzylideneacetone)dipalladium (0) chloroform adduct.

In the first step, the molar ratio of 2,6-dihalogenated benzobisthiazole and the metal catalyst (2,6-dihalogenated benzobisthiazole:metal catalyst) is not particularly limited, and is generally about 1:0.0001 to 1:0.5, and it is preferably 1:0.001 to 1:0.4, more preferably 1:0.005 to 1:0.3, further preferably 1:0.01 to 1:0.2 from the viewpoint of the yield and reaction efficiency.

In the first step, a specific ligand may be coordinated to the metal catalyst such as a copper-based catalyst or a palladium-based catalyst. Examples of the ligand include trimethylphosphine, triethylphosphine, tri(n-butyl)phosphine, tri(isopropyl)phosphine, tri(tert-butyl)phosphine, tri-tert-butylphosphonium tetrafluoroborate, bis(tert-butyl)methylphosphine, tricyclohexylphosphine, diphenyl(methyl)phosphine, triphenylphosphine, tris(o-tolyl)phosphine, tris(m-tolyl)phosphine, tris(p-tolyl)phosphine, tris(2-furyl)phosphine, tris(2-methoxyphenyl)phosphine, tris(3-methoxyphenyl)phosphine, tris(4-methoxyphenyl)phosphine, 2-dicyclohexylphosphinobiphenyl, 2-dicyclohexylphosphino-2'-methylbiphenyl, 2-dicyclohexylphosphino-2',4',6'-triisopropyl-1,1'-biphenyl, 2-dicyclohexylphosphino-2',6'-dimethoxy-1,1'-biphenyl, 2-dicyclohexylphosphino-2'-(N,N'-dimethylamino)biphenyl, 2-diphenylphosphino-2'-(N,N'-dimethylamino)biphenyl, 2-(di-tert-butyl)phosphino-2'-(N,N'-dimethylamino)biphenyl, 2-(di-tert-butyl)phosphinobiphenyl, 2-(di-tert-butyl)phosphino-2'-methylbiphenyl, 1,2-bis(diphenylphosphino)ethane, 1,3-bis(diphenylphosphino)propane, 1,4-bis(diphenylphosphino)butane, 1,2-bis(dicyclohexylphosphino)ethane, 1,3-bis(dicyclohexylphosphino)propane, 1,4-bis(dicyclohexylphosphino)butane, 1,2-bisdiphenylphosphinoethylene, 1,1'-bis(diphenylphosphino)ferrocene, 1,2-ethylenediamine, N,N,N',N'-tetramethylethylenediamine, 2,2'-bipyridyl, 1,3-diphenyldihydroimidazolylidene, 1,3-dimethyldihydroimidazolylidene, diethyldihydroimidazolylidene, 1,3-bis(2,4,6-trimethylphenyl)dihydroimidazolylidene, 1,3-bis(2,6-diisopropylphenyl)dihydroimidazolylidene, 1,10-phenanthroline, 5,6-dimethyl-1,10-phenanthroline and bathophenanthroline. Only one ligand may be used, or two or more ligands may be used. Among them, triphenylphosphine, tris(o-tolyl)phosphine and tris(2-furyl)phosphine are preferable.

When a ligand is coordinated to the metal catalyst in the first step, the molar ratio of the metal catalyst and the ligand (metal catalyst:ligand) is not particularly limited, and is generally about 1:0.5 to 1:10, and it is preferably 1:1 to 1:8, more preferably 1:1 to 1:7, further preferably 1:1 to 1:5 from the viewpoint of the yield and reaction efficiency.

In the first step, a base may coexist in the reaction of the compound (6) and/or compound (7) with 2,6-dihalogenated benzobisthiazole in the presence of the metal catalyst. Particularly when $T^1$ and $T^2$ are each a group represented by one of the formulae (t1) and (t2) in the formulae (6) and (7), it is preferable that a base coexists. When $T^1$ and $T^2$ are each a group represented by one of the formulae (t3) to (t5) in the formulae (6) and (7), whether or not a base should coexist can be determined according to the type of $R^5$ and $R^6$. For example, when $R^5$ and $R^6$ are each a group represented by *-$M^3(R^7)_kR^8$, it is preferable that a base coexists when $M^3$ is a boron atom, and a base is not required to coexist when $M^3$ is a tin atom.

Examples of the base include alkali metal salt compounds such as lithium hydride, sodium hydroxide, potassium hydroxide, cesium hydroxide, lithium carbonate, sodium carbonate, potassium carbonate and cesium carbonate; alkali earth metal salt compounds such as magnesium hydroxide, calcium hydroxide, barium hydroxide, magnesium carbonate, calcium carbonate and barium carbonate; alkoxy alkali metal compounds such as lithium methoxide, sodium methoxide, potassium methoxide, lithium ethoxide, sodium ethoxide, potassium ethoxide, lithium isopropoxide, sodium isopropoxide, potassium isopropoxide, lithium tert-butoxide, sodium tert-butoxide, potassium tert-butoxide, lithium tert-amylalkoxide, sodium tert-amylalkoxide and potassium tert-amylalkoxide; and metal hydride compounds such as lithium hydride, sodium hydride and potassium hydride. Particularly, the base is preferably an alkoxy alkali metal compound, more preferably lithium tert-butoxide, sodium tert-butoxide, potassium tert-butoxide, sodium carbonate, potassium carbonate or cesium carbonate.

In the first step, the molar ratio of 2,6-dihalogenated benzobisthiazole and the base (2,6-dihalogenated benzobisthiazole:base) is not particularly limited, and is generally about 1:1 to 1:10, and it is preferably 1:1.5 to 1:8, more preferably 1:1.8 to 1:6, further preferably 1:2 to 1:5 from the viewpoint of the yield and reaction efficiency.

In the first step, the solvent in which the compound (6) and/or compound (7) are reacted with 2,6-dihalogenated benzobisthiazole in the presence of the metal catalyst is not particularly limited as long as the reaction is not affected, and an ether-based solvent, an aromatic-based solvent, an ester-based solvent, a hydrocarbon-based solvent, a halogen-based solvent, a ketone-based solvent, an amide-based solvent or the like may be used. Examples of the ether-based solvent include diethyl ether, dipropyl ether, diisopropyl ether, dibutyl ether, tetrahydrofuran, methyltetrahydrofuran, dimethoxyethane, cyclopentyl methyl ether, t-butyl methyl ether and dioxane. Examples of the aromatic-based solvent include benzene, toluene, xylene, mesitylene, chlorobenzene and dichlorobenzene. Examples of the ester-based solvent include methyl acetate, ethyl acetate, propyl acetate, isopropyl acetate and butyl acetate. Examples of the hydrocarbon-based solvent include pentane, hexane and heptane. Examples of the halogen-based solvent include dichloromethane, chloroform, dichloroethane and dichloropropane. Examples of the ketone-based solvent include acetone, methyl ethyl ketone and methyl isobutyl ketone. Examples of the amide-based solvent include N,N-dimethylformamide, N,N-dimethylacetamide, 1,3-dimethyl-2-imidazolidinone and 1,3-dimethyl-3,4,5,6-tetrahydro-(1H)-pyrimidine. Nitrile-based solvents such as acetonitrile, sulfoxide-based solvents such as dimethylsulfoxide and sulfone-based solvents such as sulfolane may be used.

Among them, tetrahydrofuran, dioxane and N,N-dimethylformamide are especially preferable.

In the first step, the use amount of the solvent based on 1 g of 2,6-dihalogenated benzobisthiazole is not particularly limited, and is generally not less than about 1 mL and not more than about 50 mL, and it is preferably not less than 5 mL and not more than 40 mL, more preferably not less than 8 mL and not more than 35 mL, further preferably not less than 10 mL and not more than 30 mL from the viewpoint of the yield and reaction efficiency.

In the first step, the reaction temperature is not particularly limited, and it is preferably not less than 0° C. and not more than 200° C., more preferably not less than 30° C. and not more than 180° C., further preferably not less than 40° C. and not more than 150° C. for improving the reaction yield.

3.2. Second Step

Preferably, the production method according to the present invention includes the following second step.

Second step: a step of reacting a base and a halogenation reagent with a compound represented by the formula (2) to prepare a compound represented by the formula (3).

Examples of the base to be reacted with the compound (2) in the second step include alkyllithiums, alkyl metal amides, alkylmagnesiums and magnesium complexes, and alkali metal hydrides.

Examples of the alkyllithium include n-butyllithium, sec-butyllithium and tert-butyllithium. Examples of the alkyl metal amide include lithium diisopropylamide, lithium diethylamide, lithium bis(trimethylsilyl)amide, sodium bis(trimethylsilyl)amide, potassium bis(trimethylsilyl)amide, lithium-2,2,6,6-tetramethylpiperidide, lithium amide, sodium amide and potassium amide. Examples of the alkylmagnesium and magnesium complex include tert-butylmagnesium chloride, ethylmagnesium chloride, 2,2,6,6-tetramethylpiperidinylmagnesium chloride and lithium chloride complexes. Examples of the alkali metal hydride include lithium hydride, sodium hydride and potassium hydride. Among them, alkyl metal amides are preferable, and n-butyllithium and lithium diisopropylamide are especially preferable from the viewpoint of position selectivity.

In the second step, the molar ratio of the compound (2) and the base (compound (2):base) is not particularly limited, and is generally about 1:1.8 to 1:3.0, and it is preferably 1:1.9 to 1:2.6, more preferably 1:2.0 to 1:2.4, further preferably 1:2.0 to 1:2.2 from the viewpoint of the yield and reaction efficiency.

In the second step, examples of the halogenation reagent to be reacted with the compound (2) together with the base include halogen molecules and N-halogenated succinimides. Examples of the halogen molecule include chlorine, bromine and iodine. Examples of the N-halogenated succinimide include N-chlorosuccinimide, N-bromosuccinimide and N-iodosuccinimide. From the viewpoint of availability and reactivity, a halogen molecule is preferable, and iodine is especially preferable.

In the second step, the molar ratio of the compound (2) and the halogenation reagent (compound (2):halogenation reagent) is not particularly limited, and is generally about 1:1.5 to 1:20.0, and it is preferably 1:1.7 to 1:17.0, more preferably 1:1.9 to 1:15.0, further preferably 1:2.0 to 1:10.0 from the viewpoint of the yield and reaction efficiency.

The molar ratio of the base and the halogenation reagent (base:halogenation reagent) is, for example, about 1:0.5 to 1:2.0, preferably 1:0.6 to 1:1.7, more preferably 1:0.7 to 1:1.5, further preferably 1:0.8 to 1:1.2.

In the second step, the base and the halogenation reagent may be simultaneously reacted, and from the viewpoint of reaction efficiency, it is preferable that the basic compound is first reacted, and the halogenation reagent is then reacted.

In the second step, the solvent in which the compound (2) is reacted with the base and the halogenation reagent is not particularly limited, and ether-based solvents and hydrocarbon-based solvents may be used. Examples of the ether-based solvent include diethyl ether, dipropyl ether, diisopropyl ether, dibutyl ether, tetrahydrofuran, methyltetrahydrofuran, dimethoxyethane, cyclopentyl methyl ether, t-butyl methyl ether and dioxane. Examples of the hydrocarbon-based solvent include pentane, hexane, heptane, benzene, toluene and xylene. Among them, ether-based solvents are preferable, and tetrahydrofuran is especially preferable. The one solvent may be used alone, or two or more solvents may be used in combination.

In the second step, the use amount of the solvent based on 1 g of the compound (2) is not particularly limited, and is generally not less than 3 mL and about 150 mL, and it is preferably not less than 5 mL and not more than 120 mL, more preferably not less than 8 mL and not more than 100 mL, further preferably not less than 10 mL and not more than 80 mL from the viewpoint of the yield and reaction efficiency.

In the second step, the temperature at which the base and the halogenation reagent are reacted with the compound (2) is preferably equal to or less than room temperature, more preferably −30° C. or less, further preferably −35° C. or less for suppressing generation of byproducts.

3-3. Third Step

Preferably, the production method according to the present invention includes the following third step.

Third step: a step of reacting a compound represented by the following formula (8) and/or formula (9) with a compound represented by the formula (3) in the presence of a metal catalyst to prepare a compound represented by the formula (4).

[Chemical Formula 65]

(8)

(9)

[In the formulae (8) and (9), $B^1$ and $B^2$ each represent a group similar to one described above. $R^9$ to $R^{12}$ each independently represent an aliphatic hydrocarbon group with a carbon number of 1 to 6, hydroxyl group, an alkoxy group with a carbon number of 1 to 6, an aryl group with a carbon number of 6 to 10, or an aryloxy group with a carbon number of 6 to 10. $M^4$ and $M^5$ each represent a boron atom, a tin atom or a silicon atom. $R^9$ and $R^{10}$ may form a ring with $M^4$, and $R^{11}$ and $R^{12}$ may form a ring with $M^5$. p and q each represent an integer of 1 or 2. When p is 2, a plurality of $R^9$s may be each same or different. When q is 2, a plurality of $R^{11}$s may be each same or different].

In the third step, the compound represented by the formula (8) and/or formula (9) (hereinafter, sometimes referred to as a "compound (8)" and/or "compound (9)"), which is reacted with the compound (3), is preferably a compound in which $B^1$ and $B^2$ are each a group similar to one described above. As *-$M^4(R^9)_pR^{10}$ and *-$M^5(R^{11})_qR^{12}$ in the compounds (8) and (9), groups similar to the groups shown as examples when $R^{11}$ and $R^{12}$ in the compounds (6) and (7) to be used in the first step are *-$M^3(R^{13})_kR^{14}$ and the groups shown as examples when $R^{15}$ to $R^{17}$ and $R^{15'}$ in the formulae (1) to (t5) are *—$Si(R^{18})_3$ may be shown as preferred examples.

Particularly, as *-$M^4(R^9)_pR^{10}$ and *-$M^5(R^{11})_qR^{12}$ when $M^4$ and $M^5$ are boron atoms, for example, groups represented by the following formulae may be preferably used. * represents a bond.

[Chemical Formula 66]

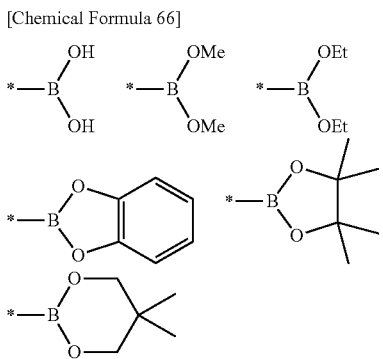

When $M^4$ and $M^5$ are tin atoms, examples of *-$M^4(R^9)_pR^{10}$ and *-$M^5(R^{11})_qR^{12}$ include groups represented by the following formulae. * represents a bond.

*—Sn(Me)$_3$  *—Sn(Bu)$_3$  [Chemical Formula 67]

When $M^4$ and $M^5$ are silicon atoms, *-$M^4(R^9)_pR^{10}$ and *-$M^5(R^{11})_qR^{12}$ are each preferably an alkylsilyl group, especially preferably trimethylsilyl group or triisopropylsilyl group.

*-$M^4(R^9)_pR^{10}$ and *-$M^5(R^{11})_qR^{12}$ in the compounds (8) and (9) may be appropriately selected according to $B^1$ and $B^2$ in the formulae (8) and (9). When $B^1$ and B2 are each a thiophene ring (preferably a group represented by the formula (b1)) optionally substituted by a hydrocarbon group or a thiazole ring (preferably a group represented by the formula (b2)) optionally substituted by a hydrocarbon group, $M^4$ and $M^6$ are each preferably a boron atom or a tin atom. When $B^1$ and $B^2$ are each an ethynylene group (preferably a group represented by the formula (b3)), $M^4$ and $M^3$ are each preferably a silicon atom.

Examples of the compounds (8) and (9) include compounds represented by the following formulae.

[Chemical Formula 68]

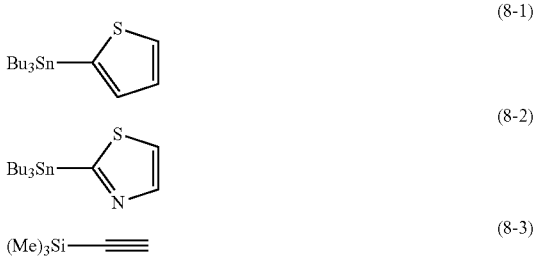

(8-1)

(8-2)

(8-3)

The compounds (8) and (9) may be same or different depending on an intended compound, and they are preferably the same for suppressing generation of byproducts.

In the third step, the molar ratio of the compound (3) and the total of the compounds (8) and (9) (compound (3):total of compounds (8) and (9)) is not particularly limited, and is generally about 1:1 to 1:10, and it is preferably 1:1.5 to 1:8, more preferably 1:2 to 1:6, further preferably 1:2 to 1:5 from the viewpoint of the yield and reaction efficiency.

As the metal catalyst to be used in the reaction of the compound (3) with the compound (8) and/or compound (9) in the third step, metal catalysts similar to those shown as examples of the metal catalyst to be used in the first step may be preferably used. Examples thereof include transition metal catalysts such as palladium-based catalysts, nickel-based catalysts, iron-based catalysts, copper-based catalysts, rhodium-based catalysts and ruthenium-based catalysts. The metal catalyst to be used in the third step is preferably a palladium-based catalyst, especially preferably dichlorobis (triphenylphosphine)palladium (II), tris(dibenzylideneacetone)dipalladium (0) or a tris(dibenzylideneacetone)dipalladium (0) chloroform adduct. When $B^1$ and $B^2$ in the formulae (8) and (9) are each ethynylene group (preferably a group represented by the formula (b3)), it is preferable to use a copper-based catalyst as the metal catalyst. Among copper-based catalysts, copper iodide (II) is especially preferable.

In the third step, the molar ratio of the compound (3) and the metal catalyst (compound (3):metal catalyst) is not particularly limited, and is generally about 1:0.0001 to 1:0.5, and it is preferably 1:0.001 to 1:0.4, more preferably 1:0.005 to 1:0.3, further preferably 1:0.01 to 1:0.2 from the viewpoint of the yield and reaction efficiency.

In the third step, a specific ligand may be coordinated to the metal catalyst such as a copper-based catalyst or a palladium-based catalyst. As the ligand, one similar to the ligand to be used in the first step may be preferably used, and triphenylphosphine, tris(o-tolyl)phosphine and tris(2-furyl) phosphine are preferable. When the ligand is coordinated to the metal catalyst in the third step, the molar ratio of the metal catalyst and the ligand (metal catalyst:ligand) is not particularly limited, and is generally about 1:0.5 to 1:10, and it is preferably 1:1 to 1:8, more preferably 1:1 to 1:7, further preferably 1:1 to 1:5 from the viewpoint of the yield and reaction efficiency.

In the third step, a base may coexist in the reaction of the compound (8) and/or compound (9) with the compound (3) in the presence of the metal catalyst, and whether or not a base should coexist can be determined according to the type of $M^4$ and $M^5$. For example, it is preferable that a base coexists when $M^4$ and $M^5$ are boron atoms or silicon atoms, and a base is not required to coexist when $M^4$ and $M^5$ are tin atoms.

As the base, bases similar to those shown as examples of the base to be used in the first step may be preferably used. Examples of the base include, in addition to the bases to be used in the first step, amines such as tertiary amines such as trimethylamine, triethylamine, tripropylamine, diisopropylethylamine, tributylamine, tripentylamine, trihexylamine, trioctylamine, triallylamine, pyridine, 2-methylpyridine, 3-methylpyridine, 4-methylpyridine, N-methylmorpholine, N,N-dimethylcyclohexylamine, N,N-dimethylaniline, N-methylimidazole, 1,4-diazabicyclo[2.2.2]octane and 1,8-diazabicyclo[5.4.0]undece-7-ene; secondary amines such as dimethylamine, diethylamine, dipropylamine, diisopropylamine, dibutylamine, dipentylamine, dihexylamine, dicyclohexylamine, dioctylamine and diallylamine; and primary amines such as methylamine, ethylamine, propylamine, isopropylamine, butylamine, pentylamine, hexylamine, cyclohexylamine, octylamine and allylamine.

The base may be selected according to the type of $M^4$ and $M^5$, and when $M^4$ and $M^5$ are boron atoms, bases shown as examples of the base to be used in the first step are preferable, alkoxy alkali metal compounds are more preferable, and lithium tert-butoxide, sodium tert-butoxide, potassium tert-butoxide, sodium carbonate, potassium carbonate and cesium carbonate are further preferable. As the base when $M^4$ and $M^5$ are silicon atoms, amines are preferable, secondary amines and tertiary amines are more preferable, and diisopropylamine, diisopropylethylamine and triethylamine are especially preferable.

In the third step, the molar ratio of the compound (3) and the base (compound (3):base) is not particularly limited, and is generally about 1:1 to 1:50, and it is preferably 1:1.5 to 1:40, more preferably 1:1.8 to 1:35, further preferably 1:2 to 1:30 from the viewpoint of the yield and reaction efficiency. When $M^4$ and $M^5$ are boron atoms, the molar ratio of the compound (3) and the base (compound (3):base) is preferably 1:1 to 1:10, more preferably 1:1.5 to 1:8, further preferably 1:1.8 to 1:6, especially preferably 1:2 to 1:5. When $M^4$ and $M^5$ are silicon atoms, the molar ratio of the compound (3) and the base (compound (3):base) is preferably 1:1 to 1:50, more preferably 1:5 to 1:40, further preferably 1:8 to 1:35, especially preferably 1:10 to: 35.

As a solvent in which the compound (8) and/or compound (9) is reacted with the compound (3) in the presence of the metal catalyst in the third step, one similar to the solvent to be used in the first step may be preferably used. In particular, tetrahydrofuran, dioxane and N,N-dimethylformamide are especially preferable.

In the third step, the use amount of the solvent based on 1 g of the compound (3) is not particularly limited, and is generally not less than about 1 mL and not more than about 50 mL, and it is preferably not less than 5 mL and not more than 40 mL, more preferably not less than 8 mL and not more than 35 mL, further preferably not less than 10 mL and not more than 30 mL from the viewpoint of the yield and reaction efficiency.

When $M^4$ and $M^5$ are silicon atoms, the use amount of the total of the solvent and the base (preferably amine) based on 1 g of the compound (3) is not particularly limited, and is generally not less than about 1 mL and not more than about 50 mL, and it is preferably not less than 5 mL and not more than 40 mL, more preferably not less than 8 mL and not more than 35 mL, further preferably not less than 10 mL and not more than 30 mL from the viewpoint of the yield and reaction efficiency. Further, when $M^4$ and $M^5$ are silicon atoms, the use amount of the solvent is, for example, 100% by volume or less, more preferably 80% by volume or less, further preferably 60% by volume or less based on 100% by volume of the total of the solvent and the base. Further, the use amount of the solvent may be 40% by volume or less, more preferably 20% by volume or less based on 100% by volume of the total of the solvent and the base, or the use amount of the solvent may be 0% by volume, i.e. no solvent may be used.

In the third step, the reaction temperature is not particularly limited, and it is preferably not less than 0° C. and not more than 200° C., more preferably not less than 30° C. and not more than 180° C., further preferably not less than 40° C. and not more than 150° C. for improving the reaction yield.

When $B^1$ and $B^2$ in the formulae (8) and (9) are each ethynylene group (preferably a group represented by the formula (b3)), and $M^4$ and $M^5$ are silicon atoms, a compound prepared by reacting the compound (3) with the compounds (8) and (9) in the third step contains organosilyl groups derived from *—$Si(R^9)_pR^{10}$ and *—$Si(R^{11})_qR^{12}$ (* represents a bond) in compounds represented by the general formulae (8) and (9), as shown in the following reaction formula:

[Chemical Formula 69]

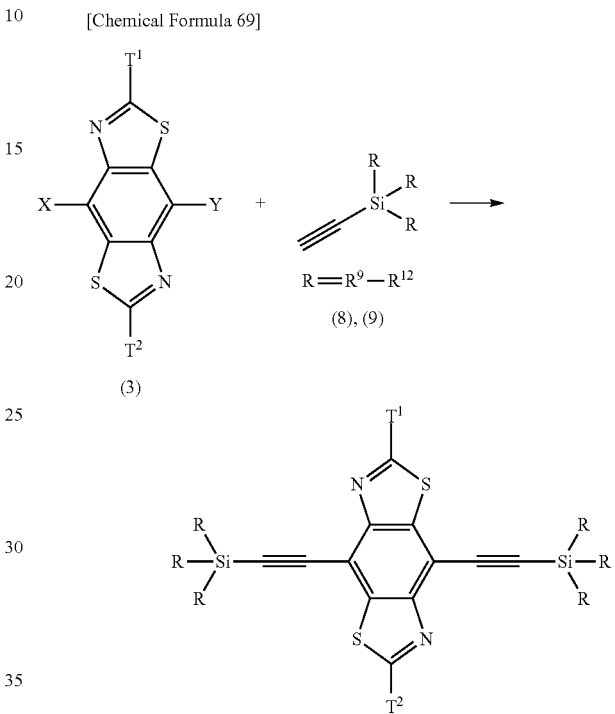

[in the reaction formula, $T^1$, $T^2$, $R^9$ to $R^{12}$, $X^1$ and $X^2$ each represent a group similar to one described above].

Therefore, it is preferable that the production method according to the present invention further includes an organosilyl group removing step. The organosilyl group removing step is preferably the following organosilyl group removing step 1 or organosilyl group removing step 2.

Organosilyl group removing step 1: a step of reacting a base with a compound having groups derived from *—$Si(R^9)_pR^{10}$ and *—$Si(R^{11})_qR^{12}$ in an alcohol-based solvent to remove the groups derived from *—$Si(R^9)_pR^{10}$ and *—$Si(R^{11})_qR^{12}$.

Organosilyl group removing step 2: a step of reacting a fluorine compound with a compound having groups derived from *—$Si(R^9)_pR^{10}$ and *—$Si(R^{11})_qR^{12}$ to remove the groups derived from *—$Si(R^9)_pR^{10}$ and *—$Si(R^{11})_qR^{12}$.

In the production method according to the present invention, the organosilyl group removing step may be carried out for a compound prepared by reacting the compound (3) with the compounds (8) and (9), or may be carried out for a macromolecular compound prepared by a coupling step as described later. In other words, the organosilyl group removing step may be carried out between the third step and the coupling step, or may be carried out after the coupling step. When $B^1$ and $B^2$ are each ethynylene group (preferably a group represented by the formula (b3)), it is not required to carry out a fourth step in the production method according to the present invention).

3-3-1. Organosilyl Group Removing Step 1

Examples of the base to be used in the organosilyl group removing step 1 include alkali metal salt compounds such as sodium hydroxide, cesium hydroxide, lithium carbonate, sodium carbonate, potassium carbonate and cesium carbonate; alkali earth metal salt compounds such as magnesium hydroxide, calcium hydroxide, barium hydroxide, magnesium carbonate, calcium carbonate and barium carbonate; and alkoxy alkali metal compounds such as lithium methoxide, sodium methoxide, potassium methoxide, lithium ethoxide, sodium ethoxide, potassium ethoxide, lithium isopropoxide, sodium isopropoxide, potassium isopropoxide, lithium tert-butoxide, sodium tert-butoxide, potassium tert-butoxide, lithium tert-amylalkoxide, sodium tert-amylalkoxide and potassium tert-amylalkoxide. Particularly, the base is preferably an alkoxy alkali metal compound, more preferably sodium carbonate, potassium carbonate or cesium carbonate.

In the organosilyl group removing step 1, the molar ratio of the compound prepared by reacting the compound (3) with the compounds (8) and (9) and the base (compound:base) is not particularly limited, and is generally about 1:0.01 to 1:10, and it is preferably 1:0.03 to 1:8, more preferably 1:0.05 to 1:6, further preferably 1:0.1 to 1:5 from the viewpoint of the yield and reaction efficiency. The reaction proceeds even when the molar amount of the base is equivalent to that of the catalyst.

Examples of the alcohol-based solvent to be used in the organosilyl group removing step 1 include methanol, ethanol, propanol, isopropyl alcohol, butanol, isobutyl alcohol, tert-butanol, pentanol, hexanol, cyclohexanol, heptanol, octanol and 2-ethylhexanol, and methanol and ethanol are especially preferable. In the organosilyl group removing step 1, a solvent similar to the solvent to be used in the first step may be used in combination as necessary, and examples of the solvent include ether-based solvents such as tetrahydrofuran, aromatic-based solvents such as toluene, amide-based solvents such as dimethylformamide. The use of such a solvent is suitable because the compound having groups derived from *—Si(R$^9$)$_p$R$^{10}$ and *—Si(R$^{11}$)$_q$R$^{12}$ is easily dissolved.

In the organosilyl group removing step 1, the use amount of the alcohol-based solvent based on 1 g of the compound prepared by reacting the compound (3) with the compounds (8) and (9) is not particularly limited, and is generally not less than about 1 mL and not more than about 50 mL, and it is preferably not less than 5 mL and not more than 40 mL, more preferably not less than 8 mL and not more than 35 mL, further preferably not less than 10 mL and not more than 30 mL from the viewpoint of the yield and reaction efficiency.

In the organosilyl group removing step 1, the reaction temperature is not particularly limited, and it is preferably not less than 0° C. and not more than 200° C., more preferably not less than 10° C. and not more than 180° C., further preferably not less than 20° C. and not more than 150° C. for improving the reaction yield.

3-3-2. Organosilyl Group Removing Step 2

Examples of the fluorine compound to be used in the organosilyl group removing step 2 include lithium fluoride, sodium fluoride, potassium fluoride, cesium fluoride, magnesium fluoride, calcium fluoride, barium fluoride, ammonium fluoride, tetramethylammonium fluoride, tetraethylammonium fluoride, tetrapropylammonium fluoride, tetrabutylammonium fluoride, tetrapentylammonium fluoride and tetrahexylammonium fluoride, and sodium fluoride, potassium fluoride, tetraethylammonium fluoride and tetrabutylammonium fluoride are preferable.

In the organosilyl group removing step 2, the molar ratio of the compound prepared by reacting the compound (3) with the compounds (8) and (9) and the fluorine compound (compound:fluorine compound) is not particularly limited, and is generally about 1:1 to 1:10, and it is preferably 1:1.5 to 1:8, more preferably 1:1.8 to 1:6, further preferably 1:2 to 1:5 from the viewpoint of the yield and reaction efficiency.

As a solvent to be used in the organosilyl group removing step 2, one similar to the solvent to be used in the first step may be preferably used. In particular, tetrahydrofuran, dioxane and N,N-dimethylformamide are especially preferable.

In the organosilyl group removing step 2, the use amount of the solvent based on 1 g of the compound prepared by reacting the compound (3) with the compounds (8) and (9) is not particularly limited, and is generally not less than about 1 mL and not more than about 50 mL, and it is preferably not less than 5 mL and not more than 40 mL, more preferably not less than 8 mL and not more than 35 mL, further preferably not less than 10 mL and not more than 30 mL from the viewpoint of the yield and reaction efficiency.

In the organosilyl group removing step 2, the reaction temperature is not particularly limited, and it is preferably not less than 0° C. and not more than 200° C., more preferably not less than 10° C. and not more than 180° C., further preferably not less than 20° C. and not more than 150° C. for improving the reaction yield.

3-4. Fourth Step

Preferably, the production method according to the present invention includes the following fourth step.

Fourth step: a step of reacting a base and a tin halide compound with a compound represented by the formula (4) to prepare a compound represented by the formula (5). In the present invention, it is preferable that the production method includes the fourth step when in the compound (4), $B^1$ and $B^2$ in the formula (4) are each a thiophene ring (preferably a group represented by the formula (b1)) optionally substituted by a hydrocarbon group or a thiazole ring (preferably a group represented by the formula (b2)) optionally substituted by a hydrocarbon group.

As the base to be reacted with the compound (4) in the fourth step, any of the bases shown as examples in the second step may be used, and among them, alkyl metal amides are preferable, and lithium diisopropylamide is especially preferable.

In the fourth step, the molar ratio of the compound (4) and the base (compound (4):base) is not particularly limited, and is generally about 1:1 to 1:5, and it is preferably 1:1.1 to 1:4, more preferably 1:1.5 to 1:3, further preferably 1:1.8 to 1:2.5 from the viewpoint of the yield and reaction efficiency.

Examples of tin halide compound to be reacted with the compound (4) together with the base in the fourth step include alkyltin halide compounds, cycloalkyltin halide compounds and aryltin halide compounds. Examples of the alkyltin halide compound include triethyltin chloride, tripropyltin chloride, tributyltin chloride, trimethyltin bromide, triethyltin bromide, tripropyltin bromide and tributyltin bromide. Examples of the cycloalkyltin halide compound include tricyclohexyltin chloride and tricyclohexyltin bromide. Examples of the aryltin halide compound include triphenyltin chloride, tribenzyltin chloride, triphenyltin bromide and tribenzyltin bromide. Among them, alkyltin halide compounds are preferable, and trimethyltin chloride and tributyltin chloride are more preferable.

In the fourth step, the molar ratio of the compound (4) and the halogenated silane compound (compound (4):halogenated silane compound) is not particularly limited, and is generally about 1:1 to 1:5, and it is preferably 1:1.1 to 1:4, more preferably 1:1.5 to 1:3, further preferably 1:1.8 to 1:2.5 from the viewpoint of the yield and reaction efficiency.

The molar ratio of the base and the tin halide compound (base:tin halide compound) is, for example, about 1:0.5 to 1:2.0, preferably 1:0.6 to 1:1.7, more preferably 1:0.7 to 1:1.5, further preferably 1:0.8 to 1:1.2.

The base and the tin halide compound may be simultaneously reacted with the compound (4), and from the viewpoint of the reaction yield, it is preferable that the base is first reacted with the compound (4), and the tin halide compound is then reacted. In the fourth step, the temperature at which the compound (4) is reacted with the base, and the tin halide compound is then added is preferably equal to or less than room temperature, more preferably 0° C. or less from the viewpoint of suppressing generation of byproducts.

In the fourth step, the solvent in which the base and the tin halide compound are reacted with the compound (4) is not particularly limited, and ether-based solvents, hydrocarbon-based solvents and so on may be used. Examples of the ether-based solvent include diethyl ether, dipropyl ether, diisopropyl ether, dibutyl ether, tetrahydrofuran, methyltetrahydrofuran, dimethoxyethane, cyclopentyl methyl ether, t-butyl methyl ether and dioxane. Examples of the hydrocarbon-based solvent include pentane, hexane, heptane, benzene, toluene and xylene. Among them, tetrahydrofuran is preferable. One solvent may be used alone, or two or more solvents may be used in combination.

In the fourth step, the use amount of the solvent based on 1 g of the compound (4) is not particularly limited, and is generally not less than about 1 mL and not more than about 70 mL, and it is preferably not less than 5 mL and not more than 60 mL, more preferably not less than 10 mL and not more than 50 mL, further preferably not less than 20 mL and not more than 45 mL from the viewpoint of the yield and reaction efficiency.

3-5. Coupling Reaction

Further, using a coupling reaction, structural units according to the present invention and structural units which are combined with the structural units according to the present invention to form a donor-acceptor-type macromolecular compound can be alternately arranged to produce a macromolecular compound according to the present invention.

The coupling reaction can be carried out by reacting the compound (4) or the compound (5) with any of compounds represented by the following formulae (C1) to (C31) in the presence of a metal catalyst.

[Chemical Formula 70]

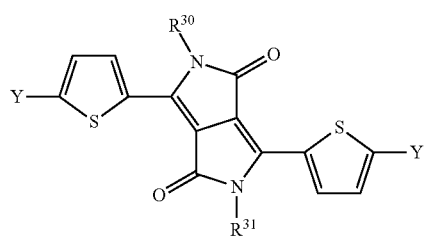

(C1)

-continued

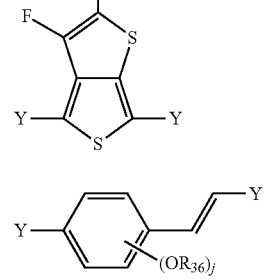

(C2)

(C3)

(C4)

(C5)

(C6)

(C7)

(C8)

(C9)

(C10) 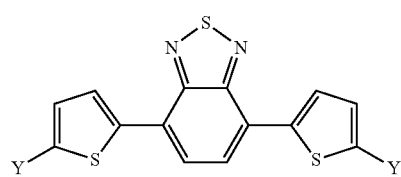
(C11) 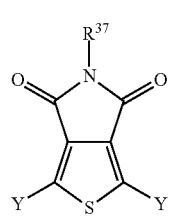
(C12) 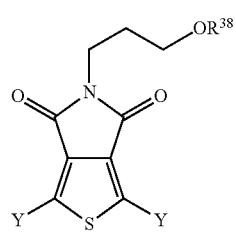
(C13) 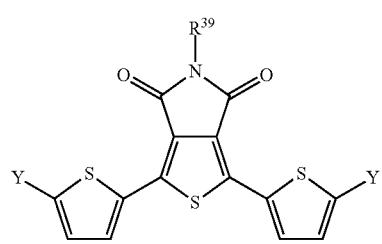
(C14) 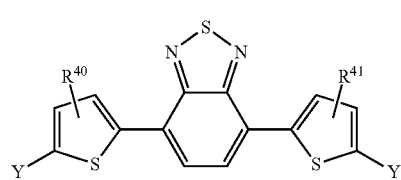
(C15) 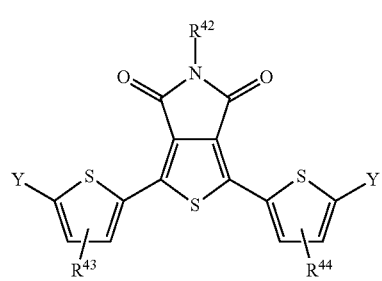
(C16) 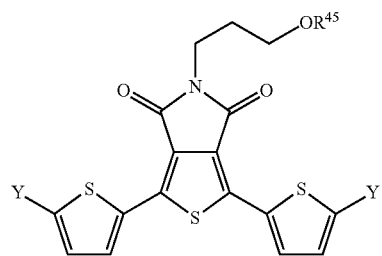
(C17) 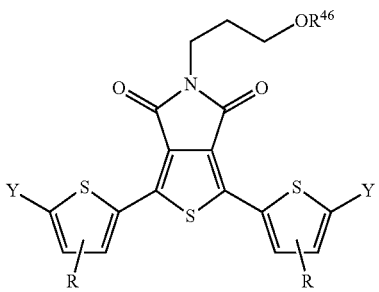
(C18) 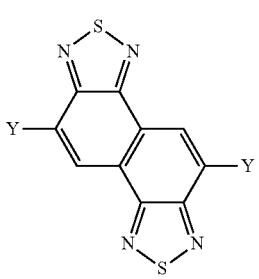
(C19) 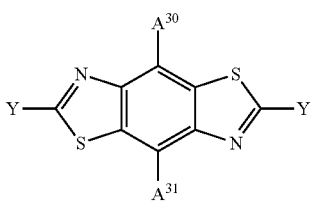
(C20) 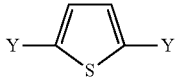
(C21) 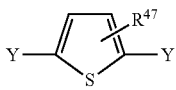
(C22) 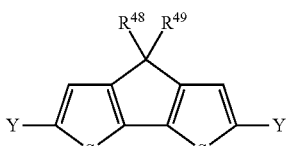
(C23) 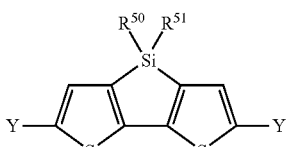
(C24) 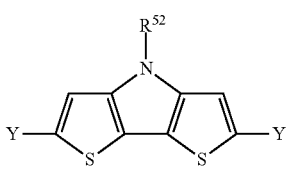

-continued

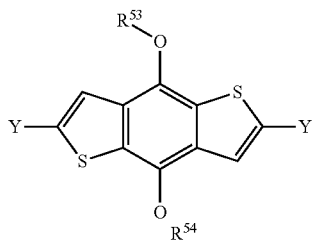
(C25)

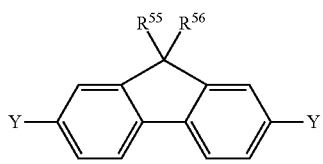
(C26)

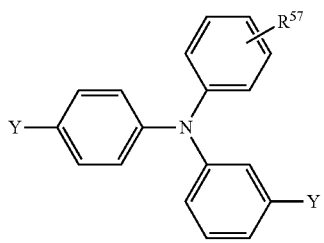
(C27)

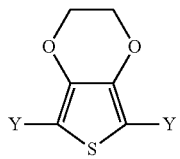
(C28)

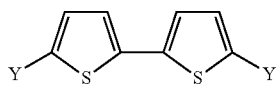
(C29)

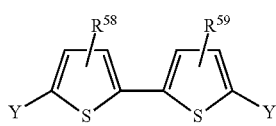
(C30)

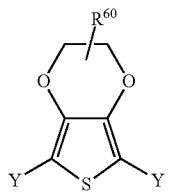
(C31)

[In the formulae (C1) to (C31), R, $R^{30}$ to $R^{60}$ each independently represent a group similar to the hydrocarbon groups with a carbon number of 6 to 30 as $R^{13}$ to $R^{17}$, $R^{19}$ and $R^{20}$, $A^{30}$ and $A^{31}$ each independently represent a group similar to $T^1$ and $T^2$, and Y represents a halogen atom.]

The compounds represented by the above formulae (C1) to (C18) are compounds which form an acceptor unit, and the compounds represented by the above formulae (C20) to (C31) are compounds which form a donor unit. The compound represented by the formula (C19) may form an acceptor unit or form a donor unit depending on the type of $A^{30}$ and $A^{31}$.

The compound according to the present invention which is subjected to the coupling reaction may be selected according to the type of $B^1$ and $B^2$ in the formulae (4) and (5). When $B^1$ and $B^2$ are each a thiophene ring (preferably a group represented by the formula (b1)) optionally substituted by a hydrocarbon group or a thiazole ring (preferably a group represented by the formula (b2)) optionally substituted by a hydrocarbon group, it is preferable to use the compound (5), and when $B^1$ and $B^2$ are each ethynylene group (preferably a group represented by the formula (b3)), it is preferable to use the compound (4).

The molar ratio of the compound (4) or the compound (5) and any one of compounds represented by the formulae (C1) to (C26) is preferably in the range of 1:99 to 99:1, preferably in the range of 20:80 to 80:20, preferably in the range of 40:60 to 60:40.

The metal catalyst for coupling is preferably a transition metal catalyst, and examples of the transition metal catalyst include palladium-based catalyst, nickel-based catalysts, iron-based catalysts, copper-based catalysts, rhodium-based catalysts and ruthenium-based catalysts. Among them, palladium-based catalysts are preferable. Palladium of the palladium-based catalyst may be zero-valent or divalent.

As the palladium-based catalyst, any of the palladium-based catalysts shown as examples in the first step may be used, and one of these catalysts may be used alone, or two or more of these catalysts may be used in combination. Among them, dichlorobis(triphenylphosphine)palladium (II), tris(dibenzylideneacetone)dipalladium (0) and tris(dibenzylideneacetone)dipalladium (0) chloroform adducts are especially preferable.

In the coupling step, the molar ratio of the compound represented by the formula (4) or (5) and the metal catalyst (compound (4) or (5):metal catalyst) is not particularly limited, and is generally about 1:0.0001 to 1:0.5, and it is preferably 1:0.001 to 1:0.3, more preferably 1:0.005 to 1:0.2, further preferably 1:0.01 to 1:0.1 from the viewpoint of the yield and reaction efficiency.

In the coupling reaction, a specific ligand may be coordinated to the metal catalyst. As the ligand, any of the ligands shown as examples in the first step may be used, and a catalyst to which any one of these ligands is coordinated may be used in the reaction. One ligand may be used alone, or two or more ligands may be used in combination. Among them, triphenylphosphine, tris(o-tolyl)phosphine and tris(2-methoxyphenyl)phosphine are preferable.

When a ligand is coordinated to the metal catalyst in the coupling step, the molar ratio of the metal catalyst and the ligand (metal catalyst:ligand) is not particularly limited, and is generally about 1:0.5 to 1:10, and it is preferably 1:1 to 1:8, more preferably 1:1 to 1:7, further preferably 1:1 to 1:5 from the viewpoint of the yield and reaction efficiency.

The solvent in which the compound (4) or the compound (5) is reacted with any one of compounds represented by the formulae (C1) to (C26) in the coupling reaction is not particularly limited as long as the reaction is not affected, and previously known solvents, for example ether-based solvents, aromatic-based solvents, ester-based solvents, hydrocarbon-based solvents, halogen-based solvents, ketone-based solvents, amide-based solvents and so on may be used. Examples of the ether-based solvent include diethyl ether, dipropyl ether, diisopropyl ether, dibutyl ether, tetrahydrofuran, methyltetrahydrofuran, dimethoxyethane, cyclopentyl methyl ether, tert-butyl methyl ether and dioxane. Examples of the aromatic-based solvent include benzene, toluene, xylene, mesitylene, chlorobenzene, dichlorobenzene and tetralin. Examples of the ester-based solvent include methyl acetate, ethyl acetate, propyl acetate, isopropyl acetate and butyl acetate. Examples of the hydrocarbon-based solvent include pentane, hexane, heptane, octane and decalin. Examples of the halogen-based solvent include dichloromethane, chloroform, dichloroethane and dichloropropane. Examples of the ketone-based solvent include acetone, methyl ethyl ketone and methyl isobutyl ketone. Examples of the amide-based solvent include N,N-dimethylformamide, N,N-dimethylacetamide, 1,3-dimethyl-2-imidazolidinone and 1,3-dimethyl-3,4,5,6-tetrahydro-(1H)-pyrimidinone. In addition, nitrile-based solvents such as acetonitrile, sulfoxide-based solvents such as dimethylsulfoxide, and sulfone-based solvents such as sulfolane may be used. Among them, tetrahydrofuran, toluene, chlorobenzene and N,N-dimethylformamide are preferable, and chlorobenzene is especially preferable. One solvent may be used alone, or two or more solvents may be used in combination.

In the coupling step, the use amount of the solvent based on 1 g of the total of the compound (4) or the compound (5) and any one of compounds represented by the formulae (C1) to (C26) is not particularly limited, and is generally not less than about 1 mL and not more than about 150 mL, and it is preferably not less than 5 mL and not more than 100 mL, more preferably not less than 8 mL and not more than 90 mL, further preferably not less than 10 mL and not more than 80 mL from the viewpoint of the yield and reaction efficiency.

The present application claims the benefit of priority based on Japanese Patent Application No. 2014-026951 filed on Feb. 14, 2014. The disclosure of the description of Japanese Patent Application No. 2014-026951 filed on Feb. 14, 2014 is incorporated herein by reference in its entirety.

EXAMPLES

Hereinafter, the present invention will be described more in detail by way of examples, and the present invention is not limited to the following examples. Of course, the present invention can be carried out while changes are appropriately made without departing from the spirit of the foregoing and following descriptions, and these change are all encompassed in the technical scope of the present invention. In the following, "%" means "% by mass" unless otherwise specified.

Measurement methods used in examples are as described below.

(NMR Spectrum Measurement)

For the benzobisthiazole compound, a NMR spectrum measurement was made using a NMR spectrum measuring apparatus ("400 MR" manufactured by Agilent, Inc. (former Varian, Inc.) and "AVANCE 500" manufactured by Bruker Corporation).

(High-Resolution Mass Spectrum Measurement)

For the benzobisthiazole compound, a high-resolution mass spectrum measurement was made using a mass spectrometer ("MicrOTOF" manufactured by Bruker Daltnics K.K).

(Gel Permeation Chromatography (GPC))

For the benzobisthiazole compound, a molecular weight measurement was made using gel permeation chromatography (GPC). In the measurement, the benzobisthiazole compound was dissolved in a mobile phase solvent (chloroform) in a concentration of 0.5 g/L, the measurement was made under the following conditions, and the measured value was calculated based on a calibration curve prepared with polystyrene as a standard sample to calculate the number average molecular weight and weight average molecular weight of the benzobisthiazole compound. GPC conditions in the measurement are as described below.

Mobile phase: chloroform flow rate: 0.6 mL/min
Apparatus: HLC-8320GPC (manufactured by TOSOH CORPORATION)
Column: TSKgel (registered trademark), SuperHM-H' 2+TSKgel (registered trademark), SuperH2000 (manufactured by TOSOH CORPORATION)

IR Spectrum

For the benzobisthiazole compound, an IR spectrum measurement was made using an infrared spectrometer ("FT/IR-6100" manufactured by JASCO Corporation).

Ultraviolet-Visible Absorption Spectrum

The obtained benzobisthiazole compound was dissolved in chloroform in a concentration of 0.03 g/L, and an ultraviolet-visible absorption spectrum measurement was made using an ultraviolet/visible spectrometer ("UV-2450" and "UV-3150" manufactured by Shinmadzu Corporation) and a cell having an optical path length of 1 cm.

Melting Point Measurement

For the benzobisthiazole compound, a melting point measurement was made using a melting point measuring apparatus ("M-560" manufactured by Buchi, Inc.).

Ionization Potential Measurement

The benzobisthiazole compound was deposited to form a film with a thickness of 50 nm to 100 nm on a glass plate. For the film, an ionization potential measurement was made at normal temperature and normal pressure using an ultraviolet photoelectron analyzer ("AC-3" manufactured by RIKEN KEIKI Co., Ltd.)

Example 1

Synthesis of 2,6-bis[5-(3,7-dimethyloctyl)thiophene-2-yl]benzo[1,2-d; 4,5-d']bisthiazole (DBTH-DMOTH)

[Chemical Formula 71]

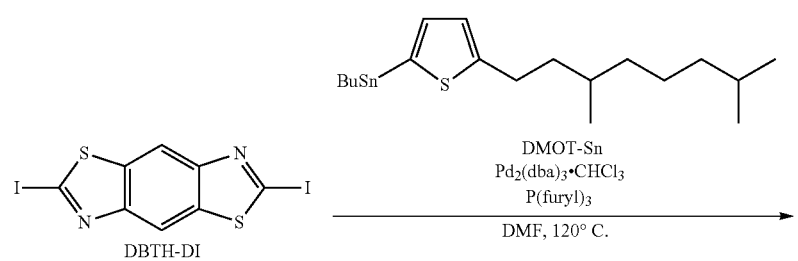

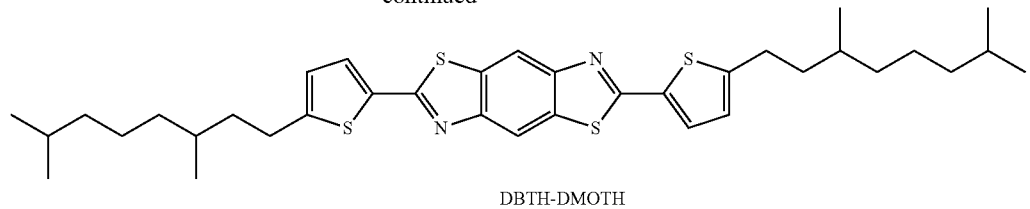

DBTH-DMOTH 2,6-diiodobenzo[1,2-d; 4,5-d']bisthiazole (DBTH-DI, 3 g, 6.76 mmol), tributyl[5-(3,7-dimethyloctyl)thiophene-2-yl]stannane (DMOT-Sn, 12.1 g, 22.6 mmol), tris(2-furyl)phosphine (188 mg, 0.81 mmol), a tris(dibenzylideneacetone) dipalladium (0)-chloroform adduct (420 mg, 0.41 mmol) and N,N-dimethylformamide (60 mL) were added in a 100 mL flask, and reacted at 120° C. for 21 hours. After the reaction was completed, the reaction product was cooled to room temperature, water was then added, the mixture was extracted twice with chloroform, and the organic layer was washed with water, and then dried with anhydrous magnesium sulfate. The organic layer was then filtered and concentrated to obtain a crude product, and the crude product was purified by column chromatography (silica gel, chloroform/hexane=1/1) to prepare 2.0 g of 2,6-bis[5-(3,7-dimethyloctyl)thiophene-2-yl]benzo[1,2-d; 4,5-d']bisthiazole (DBTH-DMOTH) as a yellow solid (yield: 46%).

Generation of an intended compound was confirmed by $^{1}$H-NMR measurement. $^{1}$H NMR (400 MHz, CDCl$_3$): δ 8.38 (s, 2H), 7.50 (d, J=3.8 Hz, 2H), 6.84 (d, J=3.8 Hz, 2H), 2.89 (m, 4H), 1.76 (m, 2H), 1.54 (m, 6H), 1.33 (m, 6H), 1.15 (m, 6H), 0.92 (d, J=5.6 Hz, 6H), 0.87 (d, J=6.4 Hz, 12H).

Example 2

Synthesis of 2,6-bis[5-(2-ethylhexyl)thiophene-2-yl]benzo[1,2-d; 4,5-d']bisthiazole (DBTH-EHTH)

[Chemical Formula 72]

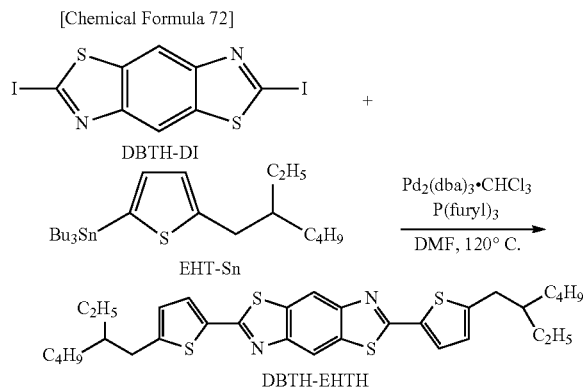

2,6-diiodobenzo[1,2-d; 4,5-d']bisthiazole (DBTH-DI, 2.7 g, 6.03 mmol), tributyl[5-(2-ethylhexyl)thiophene-2-yl]stannane (EHT-Sn, 10.2 g, 22.11 mmol), tris(2-furyl)phosphine (140 mg, 0.60 mmol), a tris(dibenzylideneacetone) dipalladium (0)-chloroform adduct (156 mg, 0.15 mmol) and N,N-dimethylformamide (55 mL) were added in a 100 mL flask, and reacted at 120° C. for 22 hours. After the reaction was completed, the reaction product was cooled to room temperature, water was then added, the mixture was extracted twice with chloroform, and the organic layer was washed with water, and then dried with anhydrous magnesium sulfate. The organic layer was then filtered and concentrated to obtain a crude product, and the crude product was purified by column chromatography (silica gel, chloroform/hexane=1/1) to prepare 1.38 g of 2,6-bis[5-(2-ethylhexyl)thiophene-2-yl]benzo[1,2-d; 4,5-d']bisthiazole (DBTH-EHTH) as a pale yellow solid (yield: 39%).

Generation of an intended compound was confirmed by $^{1}$H-NMR measurement.

$^{1}$H NMR (400 MHz, CDCl$_3$): δ 8.39 (s, 2H), 7.53 (d, J=3.8 Hz, 2H), 6.83 (d, J=3.8 Hz, 2H), 2.81 (m, 4H), 1.63 (m, 2H), 1.38 (m, 4H), 1.31 (m, 12H), 0.91 (t, J=6.4 Hz, 6H), 0.88 (t, J=6.4 Hz, 6H).

Example 3

Synthesis of 2,6-bis[5-(2-butyloctyl)thiophene-2-yl]benzo[1,2-d; 4,5-d']bisthiazole (DBTH-BOTH)

[Chemical Formula 73]

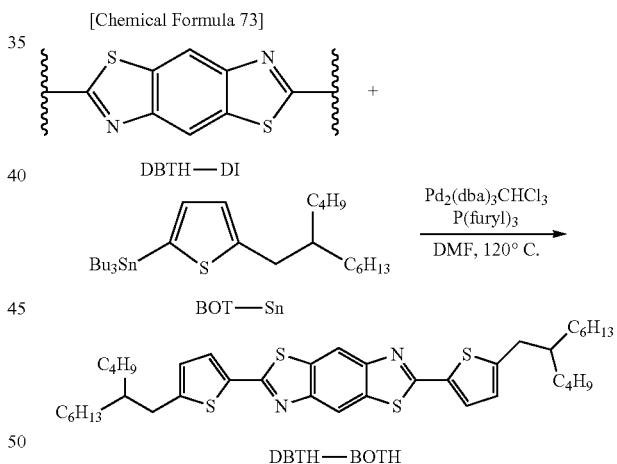

2,6-diiodobenzo[1,2-d; 4,5-d']bisthiazole (DBTH-DI, 0.86 g, 1.93 mmol), tributyl[5-(2-butyloctyl)thiophene-2-yl]stannane (BOT-Sn, 3.4 g, 6.37 mmol), tris(2-furyl)phosphine (72 mg, 0.31 mmol), a tris(dibenzylideneacetone) dipalladium (0)-chloroform adduct (8 mg, 0.08 mol) and N,N-dimethylformamide (20 mL) were added in a 50 mL flask, and reacted at 120° C. for 24 hours. After the reaction was completed, the reaction product was cooled to room temperature, water was then added, the mixture was extracted twice with chloroform, and the organic layer was washed with water, and then dried with anhydrous magnesium sulfate. The organic layer was then filtered and concentrated to obtain a crude product, and the crude product was purified by column chromatography (silica gel, chloroform/hexane=1/1) to prepare 0.68 g of 2,6-bis[5-(2-butyloctyl)thiophene-2-yl]benzo[1,2-d; 4,5-d']bisthiazole (DBTH-BOTH) as a pale yellow solid (yield: 51%).

Generation of an intended compound was confirmed by $^1$H-NMR measurement.

$^1$H NMR (400 MHz, CDCl$_3$): δ 8.42 (s, 2H), 7.59 (d, J=3.8 Hz, 2H), 6.82 (d, J=3.8 Hz, 2H), 2.81 (m, 4H), 1.66 (m, 2H), 1.37-1.24 (m, 32H), 0.91 (t, J=6.4 Hz, 6H), 0.88 (t, J=6.4 Hz, 6H).

Example 4

Synthesis of 2,6-bis[5-(2-hexyldecyl)thiophene-2-yl]benzo[1,2-d; 4,5-d']bisthiazole (DBTH-HDTH)

[Chemical Formula 74]

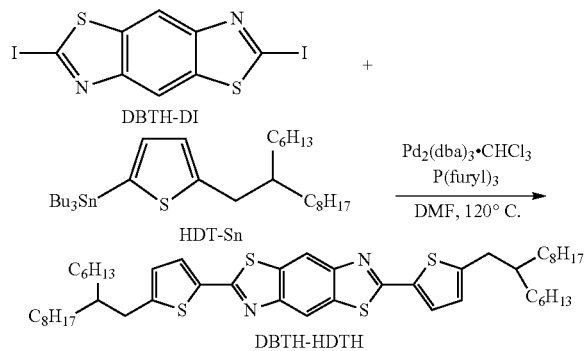

2,6-diiodobenzo[1,2-d; 4,5-d']bisthiazole (DBTH-DI, 5.2 g, 11.7 mmol), tributyl[5-(2-hexyldecyl)thiophene-2-yl] stannane (HDT-Sn, 23.2 g, 38.6 mmol), tris(2-furyl)phosphine (443 mg, 1.87 mmol), a tris(dibenzylideneacetone) dipalladium (0)-chloroform adduct (490 mg, 0.47 mol) and N,N-dimethylformamide (115 mL) were added in a 300 mL flask, and reacted at 120° C. for 23 hours. After the reaction was completed, the reaction product was cooled to room temperature, water was then added, the mixture was extracted twice with chloroform, and the organic layer was washed with water, and then dried with anhydrous magnesium sulfate. The organic layer was then filtered and concentrated to obtain a crude product, and the crude product was purified by column chromatography (silica gel, chloroform/hexane=1/1) to prepare 5.62 g of 2,6-bis[5-(2-hexyldecyl)thiophene-2-yl]benzo[1,2-d; 4,5-d']bisthiazole (DBTH-HDTH) as a pale yellow solid (yield: 60%).

Generation of an intended compound was confirmed by $^1$H-NMR measurement.

$^1$H NMR (400 MHz, CDCl$_3$): δ 8.39 (s, 2H), 7.53 (d, J=3.6 Hz, 2H), 6.81 (d, J=3.6 Hz, 2H), 2.81 (m, 4H), 1.66 (m, 2H), 1.37-1.24 (m, 48H), 0.90 (t, J=6.4 Hz, 6H), 0.88 (t, J=6.4 Hz, 6H).

Example 5

Synthesis of 2,6-bis[5-(2-decyltetradecyl)thiophene-2-yl]benzo[1,2-d; 4,5-d']bisthiazole (DBTH-TDTH)

[Chemical Formula 75]

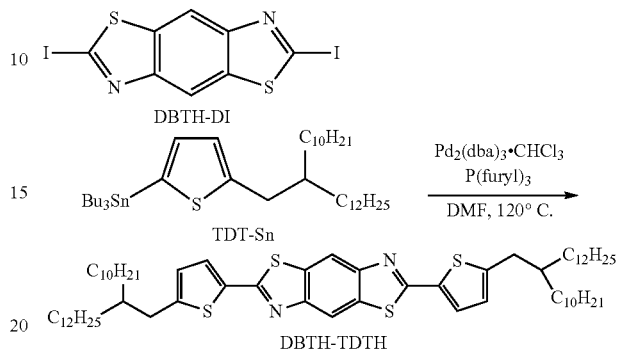

2,6-diiodobenzo[1,2-d; 4,5-d']bisthiazole (DBTH-DI, 5.2 g, 11.6 mmol), tributyl[5-(2-dodecyltetradecyl)thiophene-2-yl]stannane (TDT-Sn, 60.8 g, 38.0 mmol), tris(2-furyl)phosphine (448 mg, 2.09 mmol), a tris(dibenzylideneacetone) dipalladium (0)-chloroform adduct (493 mg, 0.46 mol) and N,N-dimethylformamide (112 mL) were added in a 200 mL flask, and reacted at 120° C. for 23 hours. After the reaction was completed, the reaction product was cooled to room temperature, water was then added, the mixture was extracted twice with chloroform, and the organic layer was washed with water, and then dried with anhydrous magnesium sulfate. The organic layer was then filtered and concentrated to obtain a crude product, and the crude product was purified by column chromatography (silica gel, chloroform/hexane=1/1) to prepare 6.12 g of 2,6-bis[5-(2-decyltetradecyl)thiophene-2-yl]benzo[1,2-d; 4,5-d']bisthiazole (DBTH-TDTH) as a pale yellow solid (yield: 51%).

Generation of an intended compound was confirmed by $^1$H-NMR measurement.

$^1$H NMR (400 MHz, CDCl$_3$): δ 8.40 (s, 2H), 7.56 (d, J=3.6 Hz, 2H), 6.81 (d, J=3.6 Hz, 2H), 2.80 (m, 4H), 1.69 (m, 2H), 1.35-1.20 (m, 80H), 0.87 (t, J=6.4 Hz, 6H), 0.86 (t, J=6.4 Hz, 6H).

Example 6

Synthesis of 2,6-bis[5-(3,7-dimethyloctyl)thiophene-2-yl]-4,8-diiodobenzo[1,2-d; 4,5-d']bisthiazole (DI-DBTH-DMOTH)

[Chemical Formula 76]

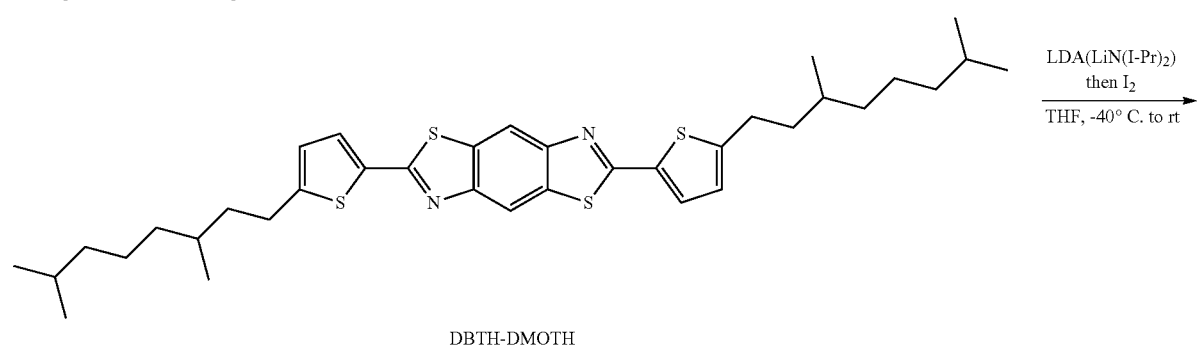

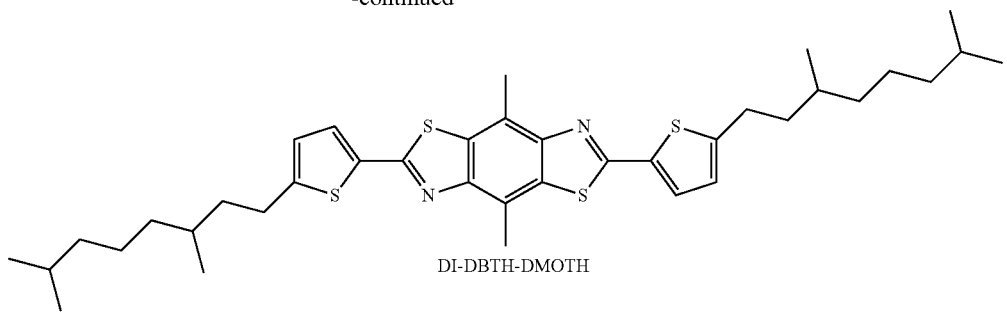

DI-DBTH-DMOTH 2,6-bis[5-(3,7-dimethyloctyl)thiophene-2-yl]benzo[1,2-d; 4,5-d']bisthiazole (DBTH-DMOTH, 1.4 g, 2.12 mmol) and tetrahydrofuran (27 mL) were added in a 50 mL flask, and cooled to −40° C., lithium diisopropylamide (2 M solution, 2.3 mL, 4.66 mmol) was then added dropwise, and the mixture was stirred for 30 minutes. Then, iodine (1.6 g, 6.36 mmol) was added, and the mixture was then reacted at room temperature for 2 hours. After the reaction was completed, 10% sodium hydrogen sulfite was added, the mixture was extracted with chloroform, and the resulting organic layer was washed with saturated sodium bicarbonate water, and then a saturated saline solution, and dried with anhydrous magnesium sulfate. Then, the organic layer was filtered and concentrated to obtain a crude product, and the crude product was purified by column chromatography (silica gel, chloroform/hexane=1/1) to prepare 1.32 g of 2,6-bis[5-(3,7-dimethyloctyl)thiophene-2-yl]-4,8-diiodobenzo[1,2-d; 4,5-d']bisthiazole (DI-DBTH-DMOTH) as a yellow solid (yield: 70%).

Generation of an intended compound was confirmed by $^1$H-NMR measurement.

$^1$H NMR (400 MHz, CDCl$_3$): δ 7.51 (d, J=3.8 Hz, 2H), 6.83 (d, J=3.8 Hz, 2H), 2.88 (m, 4H), 1.76 (m, 2H), 1.56 (m, 6H), 1.33 (m, 6H), 1.15 (m, 6H), 0.93 (d, J=5.6 Hz, 6H), 0.87 (d, J=6.4 Hz, 12H).

Example 7

Synthesis of 2,6-bis[5-(2-ethylhexyl)thiophene-2-yl]-4,8-diiodobenzo[1,2-d; 4,5-d']bisthiazole (DI-DBTH-EHTH)

2,6-bis[5-(2-ethylhexyl)thiophene-2-yl]benzo[1,2-d; 4,5-d']bisthiazole (DBTH-EHTH, 1.3 g, 2.24 mmol) and tetrahydrofuran (26 mL) were added in a 50 mL flask, and cooled to −40° C., lithium diisopropylamide (2 M solution, 2.2 mL, 4.48 mmol) was then added dropwise, and the mixture was stirred for 30 minutes. Then, iodine (1.7 g, 6.72 mmol) was added, and the mixture was then reacted at room temperature for 2 hours. After the reaction was completed, 10% sodium hydrogen sulfite was added, the mixture was extracted with chloroform, and the resulting organic layer was washed with saturated sodium bicarbonate water, and then a saturated saline solution, and dried with anhydrous magnesium sulfate. Then, the organic layer was filtered and concentrated to obtain a crude product, and the crude product was purified by column chromatography (silica gel, chloroform/hexane=1/1) to prepare 0.66 g of 2,6-bis[5-(2-ethylhexyl)thiophene-2-yl]-4,8-diiodobenzo[1,2-d; 4,5-d']bisthiazole (DI-DBTH-EHTH) as a yellow solid (yield: 36%).

Generation of an intended compound was confirmed by $^1$H-NMR measurement.

$^1$H NMR (400 MHz, CDCl$_3$): δ 7.51 (d, J=3.6 Hz, 2H), 6.81 (d, J=3.6 Hz, 2H), 2.80 (m, 4H), 1.66 (m, 2H), 1.38 (m, 4H), 1.35-1.25 (m, 12H), 0.91 (t, J=6.4 Hz, 6H), 0.88 (t, J=6.4 Hz, 6H).

[Chemical Formula 77]

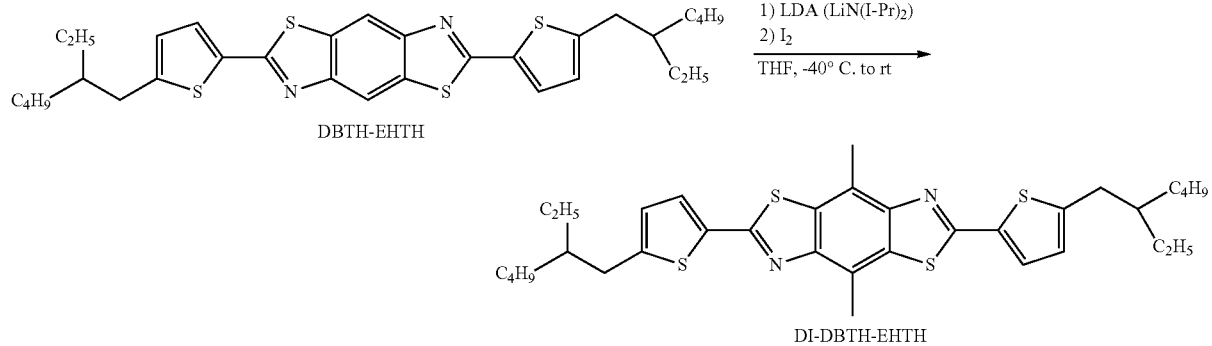

Example 8

Synthesis of 2,6-bis[5-(2-butyloctyl)thiophene-2-yl]-4,8-diiodobenzo[1,2-d; 4,5-d']bisthiazole (DI-DBTH-BOTH)

[Chemical Formula 78]

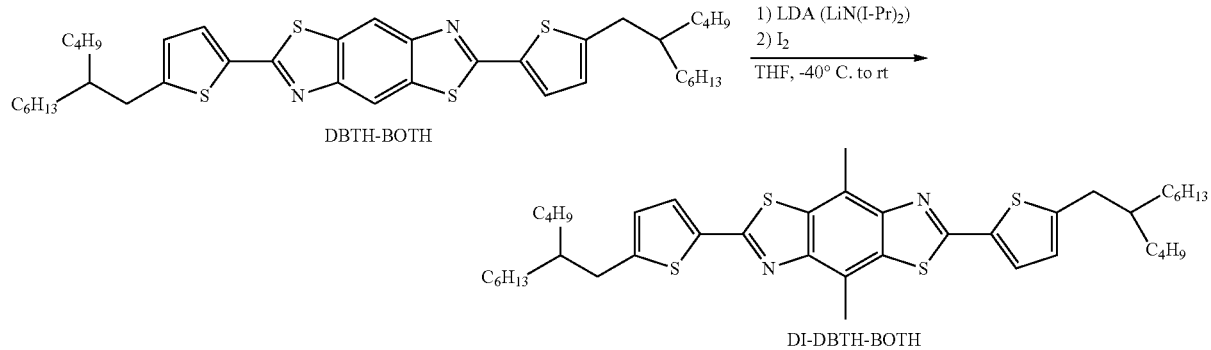

2,6-bis[5-(2-butyloctyl)thiophene-2-yl]benzo[1,2-d; 4,5-d']bisthiazole (DBTH-BOTH, 1.5 g, 2.16 mmol) and tetrahydrofuran (30 mL) were added in a 100 mL flask, and cooled to −40° C., lithium diisopropylamide (2 M solution, 2.4 mL, 4.75 mmol) was then added dropwise, and the mixture was stirred for 30 minutes. Then, iodine (1.7 g, 6.48 mmol) was added, and the mixture was then reacted at room temperature for 2 hours. After the reaction was completed, 10% sodium hydrogen sulfite was added, the mixture was extracted with chloroform, and the resulting organic layer was washed with saturated sodium bicarbonate water, and then a saturated saline solution, and dried with anhydrous magnesium sulfate. Then, the organic layer was filtered and concentrated to obtain a crude product, and the crude product was purified by column chromatography (silica gel, chloroform/hexane=1/1) to prepare 1.15 g of 2,6-bis[5-(2-butyloctyl)thiophene-2-yl]-4,8-diiodobenzo[1,2-d; 4,5-d'] bisthiazole (DI-DBTH-BOTH) as a yellow solid (yield: 56%).

Generation of an intended compound was confirmed by $^1$H-NMR measurement.

$^1$H NMR (400 MHz, CDCl$_3$): δ 7.52 (d, J=3.6 Hz, 2H), 6.80 (d, J=3.6 Hz, 2H), 2.80 (m, 4H), 1.69 (m, 2H), 1.34-1.23 (m, 32H), 0.89 (t, J=6.4 Hz, 6H), 0.86 (t, J=6.4 Hz, 6H).

Example 9

Synthesis of 2,6-bis[5-(2-hexyldecyl)thiophene-2-yl]-4,8-diiodobenzo[1,2-d; 4,5-d']bisthiazole (DI-DBTH-HDTH)

[Chemical Formula 79]

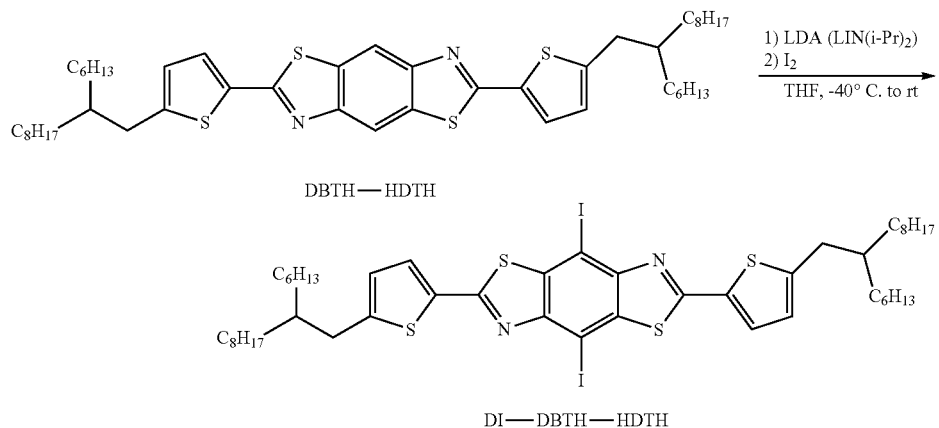

2,6-bis[5-(2-hexyldecyl)thiophene-2-yl]benzo[1,2-d; 4,5-d']bisthiazole (DBTH-HDTH, 4 g, 4.97 mmol) and tetrahydrofuran (80 mL) were added in a 100 mL flask, and cooled to −40° C., lithium diisopropylamide (2 M solution, 5.5 mL, 10.9 mmol) was then added dropwise, and the mixture was stirred for 30 minutes. Then, iodine (3.8 g, 14.9 mol) was added, and the mixture was then reacted at room temperature for 2 hours. After the reaction was completed, 10% sodium hydrogen sulfite was added, the mixture was extracted with chloroform, and the resulting organic layer was washed with saturated sodium bicarbonate water, and then a saturated saline solution, and dried with anhydrous magnesium sulfate. Then, the organic layer was filtered and concentrated to obtain a crude product, and the crude product was purified by column chromatography (silica gel, chloroform/hexane=1/1) to prepare 2.66 g of 2,6-bis[5-(2-hexyldecyl)thiophene-2-yl]-4,8-diiodobenzo[1,2-d; 4,5-d']bisthiazole (DI-DBTH-HDTH) as a yellow solid (yield: 51%).

Generation of an intended compound was confirmed by $^1$H-NMR measurement.

$^1$H NMR (400 MHz, CDCl$_3$): δ 7.53 (d, J=3.6 Hz, 2H), 6.81 (d, J=3.6 Hz, 2H), 2.80 (m, 4H), 1.70 (m, 2H), 1.36-1.24 (m, 48H), 0.89 (t, J=6.4 Hz, 6H), 0.86 (t, J=6.4 Hz, 6H).

Example 10

Synthesis of 2,6-bis[5-(2-decyltetradecyl)thiophene-2-yl]-4,8-diiodobenzo[1,2-d; 4,5-d']bisthiazole (DI-DBTH-TDTH)

[Chemical Formula 80]

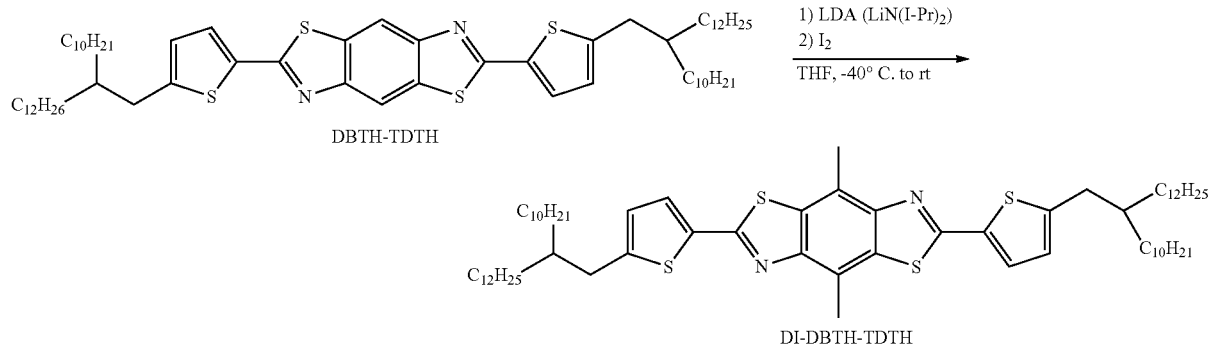

2,6-bis[5-(2-decyltetradecyl)thiophene-2-yl]benzo[1,2-d; 4,5-d']bisthiazole (DBTH-TDTH, 4.1 g, 3.97 mmol) and tetrahydrofuran (80 mL) were added in a 200 mL flask, and cooled to −40° C., lithium diisopropylamide (2 M solution, 4.4 mL, 8.8 mmol) was then added dropwise, and the mixture was stirred for 30 minutes. Then, iodine (3.1 g, 24.0 mmol) was added, and the mixture was then reacted at room temperature for 2 hours. After the reaction was completed, 10% sodium hydrogen sulfite was added, the mixture was extracted with chloroform, and the resulting organic layer was washed with saturated sodium bicarbonate water, and then a saturated saline solution, and dried with anhydrous magnesium sulfate. Then, the organic layer was filtered and concentrated to obtain a crude product, and the crude product was purified by column chromatography (silica gel, ethyl acetate/hexane=5/95) to prepare 3.98 g of 2,6-bis[5-(2-decyltetradecyl)thiophene-2-yl]-4,8-diiodobenzo[1,2-d; 4,5-d']bisthiazole (DI-DBTH-TDTH) as a yellow solid (yield: 69%).

Generation of an intended compound was confirmed by $^1$H-NMR measurement.

$^1$H NMR (400 MHz, CDCl$_3$): δ 7.53 (d, J=3.6 Hz, 2H), 6.80 (d, J=3.6 Hz, 2H), 2.80 (m, 4H), 1.70 (m, 2H), 1.38-1.20 (m, 80H), 0.89 (t, J=6.4 Hz, 6H), 0.86 (t, J=6.4 Hz, 6H).

Example 11

Synthesis of 2,6-bis[5-(3,7-dimethyloctyl)thiophene-2-yl]-4,8-dithiophene-2-yl-benzo[1,2-d; 4,5-d']bisthiazole (DTH-DBTH-DMOTH)

[Chemical Formula 81]

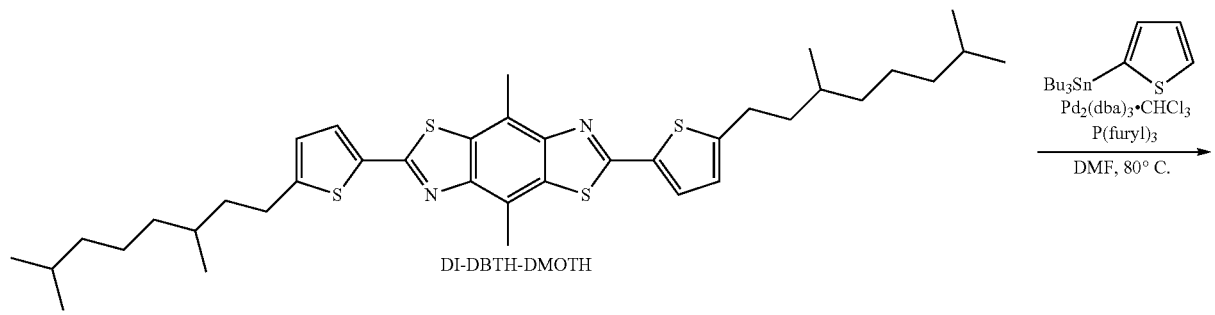

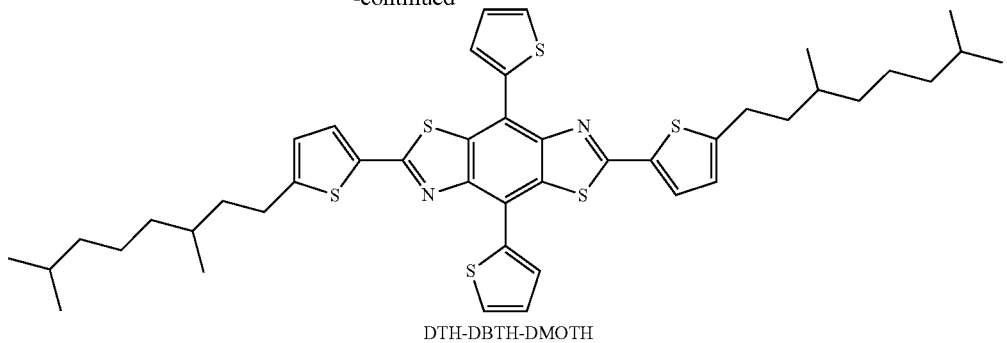

DTH-DBTH-DMOTH 2,6-bis[5-(3,7-dimethyloctyl)thiophene-2-yl]-4,8-diiodobenzo[1,2-d; 4,5-d']bisthiazole (DI-DBTH-DMOTH, 335 mg, 0.38 mmol), tributylthiophene-2-yl-stannane (301 μL, 0.94 mmol), tris(2-furyl)phosphine (14 mg, 60 μmol), a tris(dibenzylideneacetone)dipalladium (0)-chloroform adduct (16 mg, 15 μmol) and N,N-dimethylformamide (7 mL) were added in a 30 mL flask, and reacted at 80° C. for 18 hours. After the reaction was completed, the reaction product was cooled to room temperature, water was then added, the mixture was extracted twice with chloroform, and the organic layer was washed with water, and then dried with anhydrous magnesium sulfate. Then, the organic layer was filtered and concentrated to obtain a crude product, and the crude product was purified by column chromatography (silica gel, chloroform/hexane=1/1–chloroform) to prepare 248 mg of 2,6-bis[5-(3,7-dimethyloctyl)thiophene-2-yl]-4, 8-dithiophene-2-yl-benzo[1,2-d; 4,5-d']bisthiazole (DTH-DBTH-DMOTH) as a yellow solid (yield: 82%).

Generation of an intended compound was confirmed by $^1$H-NMR measurement.

$^1$H NMR (400 MHz, CDCl$_3$): δ 8.00 (d, J=4.0 Hz, 2H), 7.59 (d, J=5.2 Hz, 2H), 7.56 (d, J=4.0 Hz, 2H), 7.27 (dd, J=5.2, 4.0 Hz, 2H), 6.85 (d, J=4.0 Hz, 2H), 2.90 (m, 4H), 1.76 (m, 2H), 1.53 (m, 6H), 1.34 (m, 6H), 1.16 (m, 6H), 0.95 (d, J=5.8 Hz, 6H), 0.88 (d, J=6.4 Hz, 12H).

Example 12

Synthesis of 2,6-bis[5-(2-ethylhexyl)thiophene-2-yl]-4,8-dithiophene-2-yl-benzo[1,2-d; 4,5-d']bisthiazole (DTH-DBTH-EHTH)

[Chemical Formula 82]

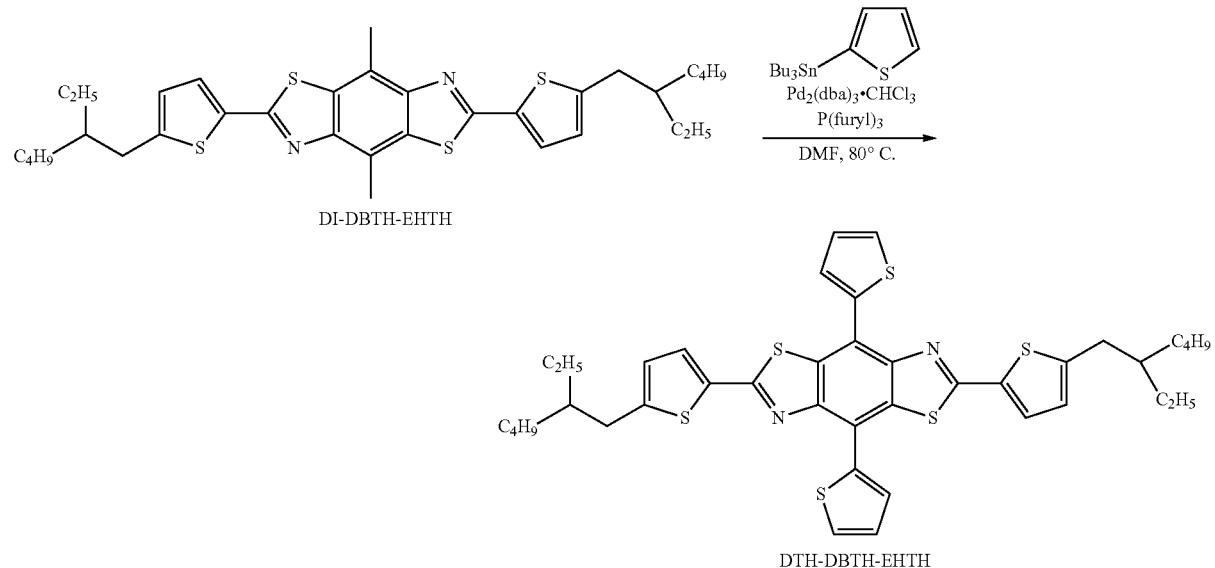

2,6-bis[5-(2-ethylhexyl)thiophene-2-yl]-4,8-diiodobenzo[1,2-d; 4,5-d']bisthiazole (DI-DBTH-EHTH, 657 mg, 0.78 mmol), tributylthiophene-2-yl-stannane (630 μL, 1.95 mmol), tris(2-furyl)phosphine (30 mg, 0.12 mmol), a tris(dibenzylideneacetone)dipalladium (0)-chloroform adduct (34 mg, 0.03 mmol) and N,N-dimethylformamide (12 mL) were added in a 20 mL flask, and reacted at 80° C. for 19 hours. After the reaction was completed, the reaction product was cooled to room temperature, water was then added, the mixture was extracted twice with chloroform, and the organic layer was washed with water, and then dried with anhydrous magnesium sulfate. Then, the organic layer was filtered and concentrated to obtain a crude product, and the crude product was purified by column chromatography (silica gel, chloroform/hexane=1/1–chloroform) to prepare 525 mg of 2,6-bis[5-(2-ethylhexyl)thiophene-2-yl]-4,8-dithiophene-2-yl-benzo[1,2-d; 4,5-d']bisthiazole (DTH-DBTH-EHTH) as a yellow solid (yield: 89%).

Generation of an intended compound was confirmed by $^1$H-NMR measurement.

$^1$H NMR (400 MHz, CDCl$_3$): δ 8.00 (dd, J=4.0, 0.8 Hz, 2H), 7.59 (dd, J=5.2, 0.8 Hz, 2H), 7.55 (d, J=4.0 Hz, 2H), 7.27 (dd, J=5.2, 4.0 Hz, 2H), 6.82 (d, J=4.0 Hz, 2H), 2.81 (m, 4H), 1.67 (m, 2H), 1.41-1.27 (m, 16H), 0.92 (t J=6.4 Hz, 6H), 0.88 (t, J=6.4 Hz, 12H).

Example 13

Synthesis of 2,6-bis[5-(2-butyloctyl)thiophene-2-yl]-4,8-dithiophene-2-yl-benzo[1,2-d; 4,5-d']bisthiazole (DTH-DBTH-BOTH)

[Chemical Formula 83]

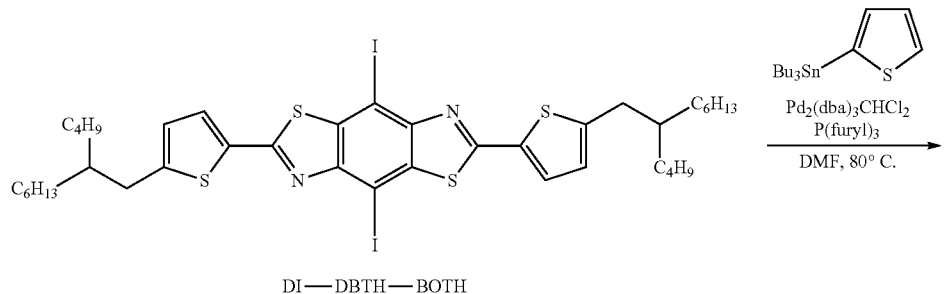

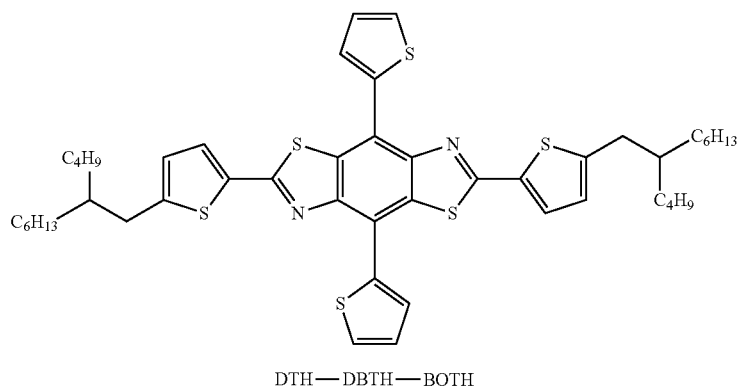

2,6-bis[5-(2-butyloctyl)thiophene-2-yl]-4,8-diiodobenzo[1,2-d; 4,5-d']bisthiazole (DI-DBTH-BOTH, 1.1 g, 1.16 mmol), tributylthiophene-2-yl-stannane (930 μL, 2.90 mmol), tris(2-furyl)phosphine (33 mg, 0.14 mmol), a tris(dibenzylideneacetone)dipalladium (0)-chloroform adduct (36 mg, 0.03 mmol) and N,N-dimethylformamide (22 mL) were added in a 50 mL flask, and reacted at 80° C. for 22 hours. After the reaction was completed, the reaction product was cooled to room temperature, water was then added, the mixture was extracted twice with chloroform, and the organic layer was washed with water, and then dried with anhydrous magnesium sulfate. Then, the organic layer was filtered and concentrated to obtain a crude product, and the crude product was purified by column chromatography (silica gel, chloroform/hexane=1/1–chloroform) to prepare 0.99 g of 2,6-bis[5-(2-butyloctyl)thiophene-2-yl]-4,8-dithiophene-2-yl-benzo[1,2-d; 4,5-d']bisthiazole (DTH-DBTH-BOTH) as a yellow solid (yield: 99%).

Generation of an intended compound was confirmed by $^1$H-NMR measurement.

$^1$H NMR (400 MHz, CDCl$_3$): δ 8.00 (dd, J=4.0, 0.8 Hz, 2H), 7.58 (dd, J=5.2, 0.8 Hz, 2H), 7.55 (d, J=4.0 Hz, 2H), 7.27 (dd, J=5.2, 4.0 Hz, 2H), 6.81 (d, J=4.0 Hz, 2H), 2.81 (m, 4H), 1.71 (m, 2H), 1.35-1.24 (m, 32H), 0.90 (t J=6.4 Hz, 6H), 0.88 (t, J=6.4 Hz, 12H).

Example 14

Synthesis of 2,6-bis[5-(2-hexyldecyl)thiophene-2-yl]-4,8-dithiophene-2-yl-benzo[1,2-d; 4,5-d']bisthiazole (DTH-DBTH-HDTH)

[Chemical Formula 84]

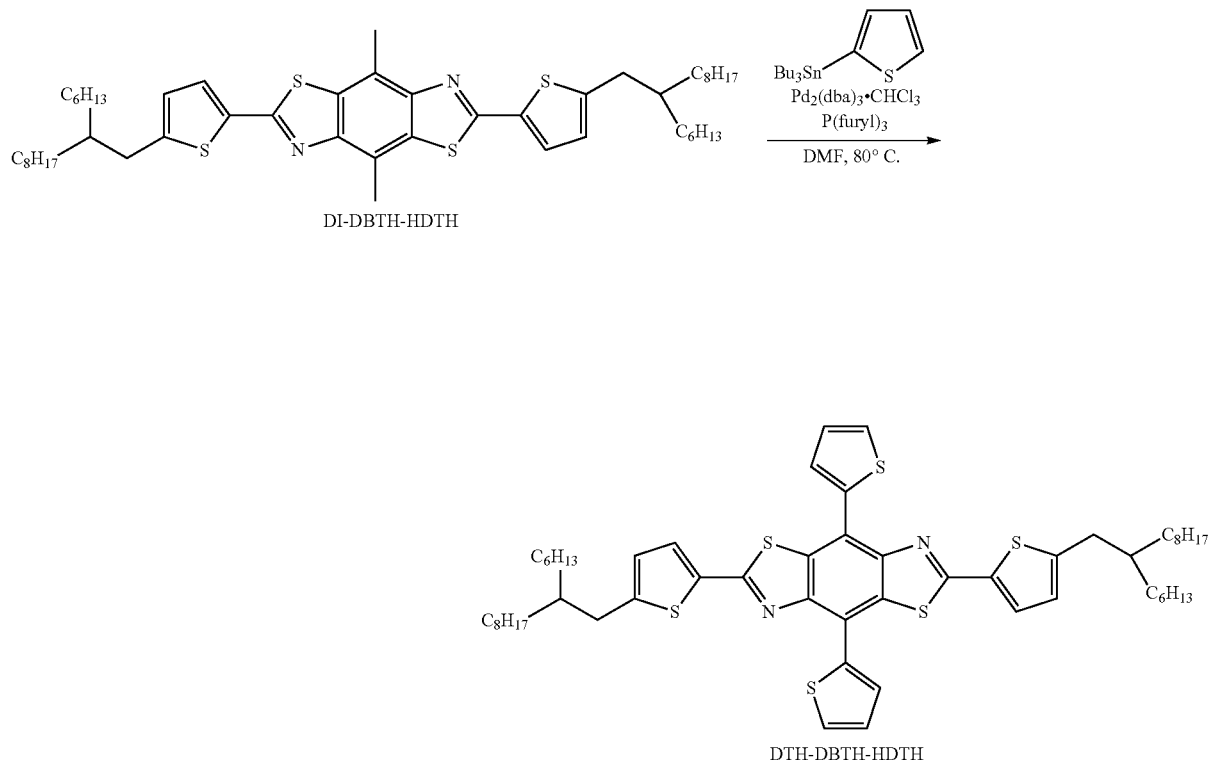

2,6-bis[5-(2-hexyldecyl)thiophene-2-yl]-4,8-diiodobenzo[1,2-d; 4,5-d']bisthiazole (DI-DBTH-HDTH, 1.1 g, 1.04 mmol), tributylthiophene-2-yl-stannane (830 μL, 2.60 mmol), tris(2-furyl)phosphine (40 mg, 0.17 mmol), a tris(dibenzylideneacetone)dipalladium (0)-chloroform adduct (45 mg, 0.04 mmol) and N,N-dimethylformamide (22 mL) were added in a 50 mL flask, and reacted at 80° C. for 19 hours. After the reaction was completed, the reaction product was cooled to room temperature, water was then added, the mixture was extracted twice with chloroform, and the organic layer was washed with water, and then dried with anhydrous magnesium sulfate. Then, the organic layer was filtered and concentrated to obtain a crude product, and the crude product was purified by column chromatography (silica gel, chloroform/hexane=1/1–chloroform) to prepare 1.01 g of 2,6-bis[5-(2-hexyldecyl)thiophene-2-yl]-4,8-dithiophene-2-yl-benzo[1,2-d; 4,5-d']bisthiazole (DTH-DBTH-HDTH) as a yellow solid (yield: 100%).

Generation of an intended compound was confirmed by $^1$H-NMR measurement.

$^1$H NMR (400 MHz, CDCl$_3$): δ 8.00 (dd, J=4.0, 0.8 Hz, 2H), 7.58 (dd, J=5.2, 0.8 Hz, 2H), 7.55 (d, J=4.0 Hz, 2H), 7.27 (dd, J=5.2, 4.0 Hz, 2H), 6.81 (d, J=4.0 Hz, 2H), 2.81 (m, 4H), 1.72 (m, 2H), 1.34-1.25 (m, 48H), 0.89 (t J=6.4 Hz, 6H), 0.87 (t, J=6.4 Hz, 12H).

Example 15

Synthesis of 2,6-bis[5-(2-decyltetradecyl)thiophene-2-yl]-4,8-dithiophene-2-yl-benzo[1,2-d; 4,5-d']bisthiazole (DTH-DBTH-TDTH)

[Chemical Formula 85]

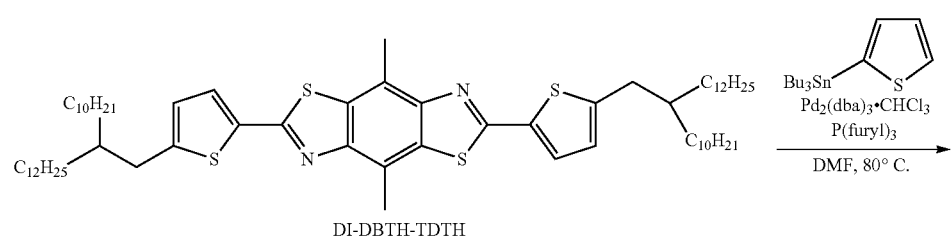

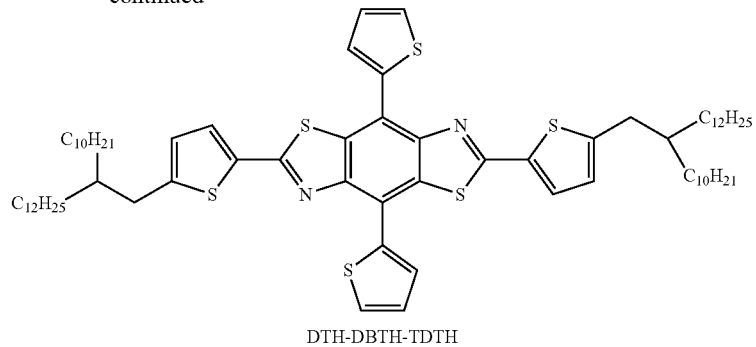

DTH-DBTH-TDTH 2,6-bis[5-(2-decyltetradecyl)thiophene-2-yl]-4,8-diiodobenzo[1,2-d; 4,5-d']bisthiazole (DI-DBTH-TDTH, 2.5 g, 1.95 mmol), tributylthiophene-2-yl-stannane (1.6 mL, 4.88 mmol), tris(2-furyl)phosphine (55 mg, 0.23 mmol), a tris(dibenzylideneacetone)dipalladium (0)-chloroform adduct (62 mg, 0.06 mmol) and N,N-dimethylformamide (50 mL) were added in a 100 mL flask, and reacted at 100° C. for 23 hours. After the reaction was completed, the reaction product was cooled to room temperature, water was then added, the mixture was extracted twice with chloroform, and the organic layer was washed with water, and then dried with anhydrous magnesium sulfate. Then, the organic layer was filtered and concentrated to obtain a crude product, and the crude product was purified by column chromatography (silica gel, ethyl acetate/hexane=1/9) to prepare 2.21 g of 2,6-bis[5-(2-tetradecyldodecyl)thiophene-2-yl]-4,8-dithiophene-2-yl-benzo[1,2-d; 4,5-d']bisthiazole (DTH-DBTH-TDTH) as a yellow solid (yield: 95%).

Generation of an intended compound was confirmed by $^1$H-NMR measurement.

$^1$H NMR (400 MHz, CDCl$_3$): δ 8.00 (dd, J=4.0, 0.8 Hz, 2H), 7.58 (dd, J=5.2, 0.8 Hz, 2H), 7.55 (d, J=4.0 Hz, 2H), 7.27 (dd, J=5.2, 4.0 Hz, 2H), 6.81 (d, J=4.0 Hz, 2H), 2.82 (m, 4H), 1.71 (m, 2H), 1.39-1.20 (m, 80H), 0.88 (t J=6.4 Hz, 6H), 0.87 (t, J=6.4 Hz, 12H).

Example 16

Synthesis of 2,6-bis[5-(3,7-dimethyloctyl)thiophene-2-yl]-4,8-bis(5-tributylstannylthiophene-2-yl)-benzo[1,2-d; 4,5-d']bisthiazole (DTH-DBTH-DMOTH-DSB)

[Chemical Formula 86]

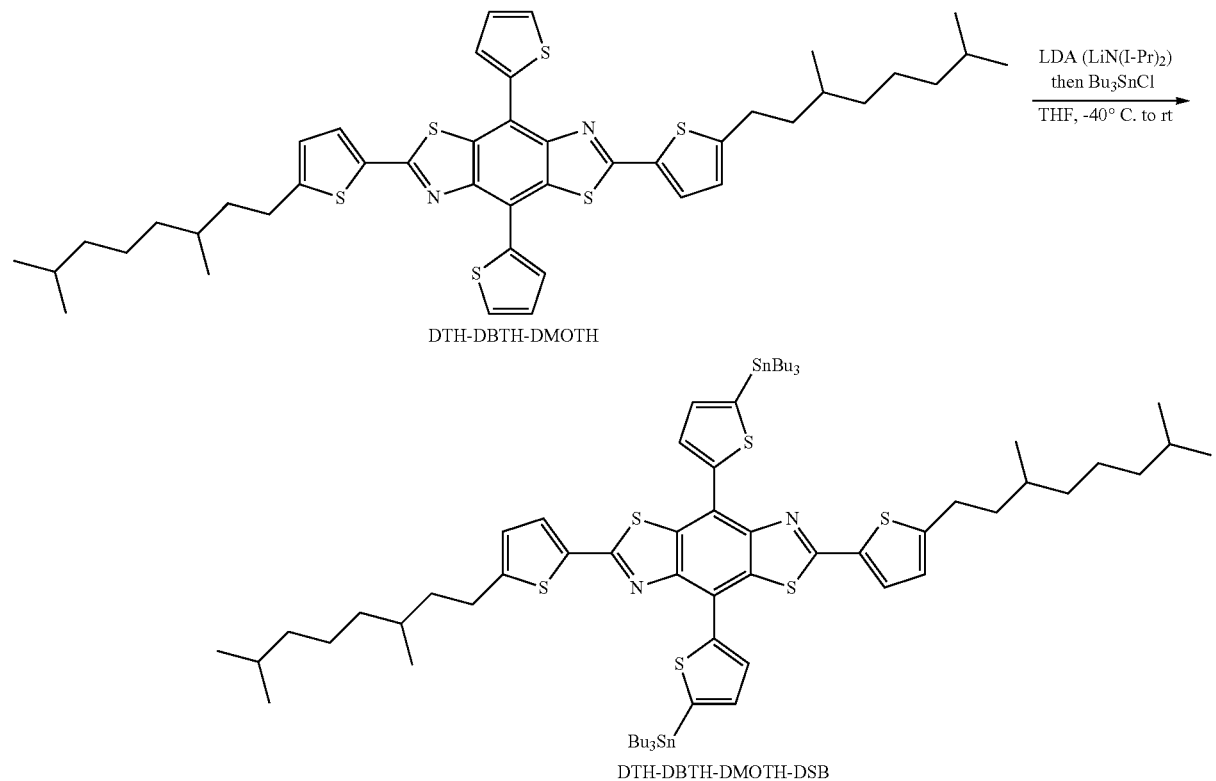

2,6-bis[5-(3,7-dimethyloctyl)thiophene-2-yl]-4,8-dithiophene-2-yl-benzo[1,2-d; 4,5-d']bisthiazole (DTH-DBTH-DMOTH, 150 mg, 0.19 mmol) and tetrahydrofuran (6 mL) were added in a 20 mL flask, and cooled to −40° C., lithium diisopropylamide (2 M solution, 0.20 mL, 0.39 mmol) was added dropwise, and the mixture was stirred for 30 minutes. Thereafter, tributyltin chloride (107 μL, 0.39 mmol) was added, and the mixture was heated to room temperature, and stirred for 2 hours. After the reaction was completed, water was added, the mixture was extracted twice with toluene, and the organic layer was washed with water, and then dried with anhydrous magnesium sulfate. Then, the organic layer was filtered and concentrated to obtain a crude product, and the crude product was purified by GPC-HPLC (JAIGEL-1H, 2H, chloroform) to prepare 163 mg of 2,6-bis[5-(3,7-dimethyloctyl)thiophene-2-yl]-4,8-bis(5-tributylstannylthiophene-2-yl)-benzo[1,2-d; 4,5-d']bisthiazole (DTH-DBTH-DMOTH-DSB) as a light brown oil (yield: 63%).

Generation of an intended compound was confirmed by $^1$H-NMR measurement.

$^1$H NMR (400 MHz, $C_6D_6$): δ 8.53 (d, J=3.6 Hz, 2H), 7.53 (d, J=3.6 Hz, 2H), 7.38 (d, J=3.6 Hz, 2H), 6.55 (d, J=3.6 Hz, 2H), 2.69 (m, 4H), 1.79 (m, 14H), 1.51 (m, 18H), 1.34 (m, 18H), 1.12 (m, 6H), 1.03 (t, J=6.8 Hz, 18H), 0.96 (d, J=7.2 Hz, 12H), 0.88 (d, J=6.4 Hz, 6H).

Example 17

Synthesis of 2,6-bis[5-(2-ethylhexyl)thiophene-2-yl]-4,8-bis(5-trimethylstannylthiophene-2-yl)-benzo[1,2-d; 4,5-d']bisthiazole (DTH-DBTH-EHTH-DSM)

[Chemical Formula 87]

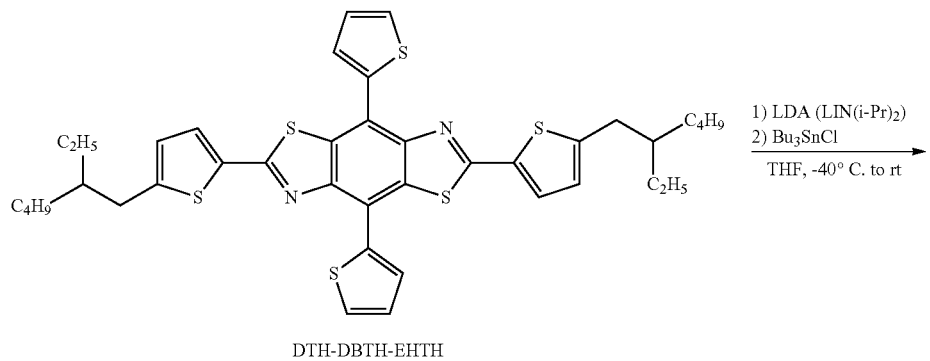

DTH-DBTH-EHTH

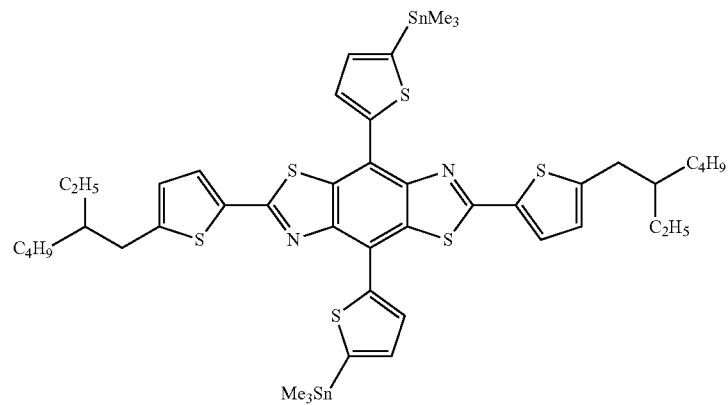

DTH-DBTH-EHTH-DSM 2,6-bis[5-(2-ethylhexyl)thiophene-2-yl]-4,8-dithiophene-2-yl-benzo[1,2-d; 4,5-d']bisthiazole (DTH-DBTH-EHTH, 500 mg, 0.67 mmol) and tetrahydrofuran (10 mL) were added in a 20 mL flask, and cooled to −50° C., lithium diisopropylamide (2 M solution, 0.74 mL, 1.47 mmol) was added dropwise, and the mixture was stirred for 30 minutes. Thereafter, trimethyltin chloride (1 M solution, 15 mL, 1.47 mmol) was added, and the mixture was heated to room temperature, and stirred for 2 hours. After the reaction was completed, water was added, the mixture was extracted twice with toluene, and the organic layer was washed with water, and then dried with anhydrous magnesium sulfate. Then, the organic layer was filtered and concentrated to obtain a crude product, and the crude product was purified by GPC-HPLC (JAIGEL-1H, 2H, chloroform) to prepare 309 mg of 2,6-bis[5-(2-ethylhexyl)thiophene-2-yl]-4,8-bis(5-trimethylstannylthiophene-2-yl)-benzo[1,2-d; 4,5-d']bisthiazole (DTH-DBTH-EHTH-DSM) as a yellow solid (yield 4396).

Generation of an intended compound was confirmed by $^1$H-NMR measurement.

$^1$H NMR (400 MHz, CDCl$_3$): δ 8.16 (d, J=3.6 Hz, 2H), 7.56 (d, J=3.6 Hz, 2H), 7.37 (d, J=3.6 Hz, 2H), 6.82 (d, J=3.6 Hz, 2H), 2.82 (m, 4H), 1.66 (m, 2H), 1.42-1.30 (m, 16H), 0.90 (t J=6.4 Hz, 6H), 0.88 (t, J=6.4 Hz, 6H), 0.46 (s, 18H).

Example 18

2,6-bis[5-(2-butyloctyl)thiophene-2-yl]-4,8-bis(5-trimethylstannylthiophene-2-yl)-benzo[1,2-d; 4,5-d']bisthiazole (DTH-DBTH-BOTH-DSM)

2,6-bis[5-(2-butyloctyl)thiophene-2-yl]-4,8-dithiophene-2-yl-benzo[1,2-d; 4,5-d']bisthiazole (DTH-DBTH-BOTH, 400 mg, 0.47 mmol) and tetrahydrofuran (8 mL) were added in a 20 mL flask, and cooled to −50° C., lithium diisopropylamide (2 M solution, 0.51 mL, 1.03 mmol) was added dropwise, and the mixture was stirred for 30 minutes. Thereafter, trimethyltin chloride (1 M solution, 10 mL, 1.03 mmol) was added, and the mixture was heated to room temperature, and stirred for 2 hours. After the reaction was completed, water was added, the mixture was extracted twice with toluene, and the organic layer was washed with water, and then dried with anhydrous magnesium sulfate. Then, the organic layer was filtered and concentrated to obtain a crude product, and the crude product was purified by GPC-HPLC (JAIGEL-1H, 2H, chloroform) to prepare 149 mg of 2,6-bis[5-(2-butyloctyl)thiophene-2-yl]-4,8-bis(5-trimethylstannylthiophene-2-yl)-benzo[1,2-d; 4,5-d']bisthiazole (DTH-DBTH-BOTH-DSM) as a yellow solid (yield 27%).

Generation of an intended compound was confirmed by $^1$H-NMR measurement.

$^1$H NMR (400 MHz, CDCl$_3$): δ 8.16 (d, J=3.6 Hz, 2H), 7.56 (d, J=3.6 Hz, 2H), 7.37 (d, J=3.6 Hz, 2H), 6.82 (d, J=3.6 Hz, 2H), 2.82 (m, 4H), 1.71 (m, 2H), 1.35-1.22 (m, 32H), 0.89 (t J=6.4 Hz, 6H), 0.88 (t, J=6.4 Hz, 6H), 0.47 (s, 18H).

[Chemical Formula 88]

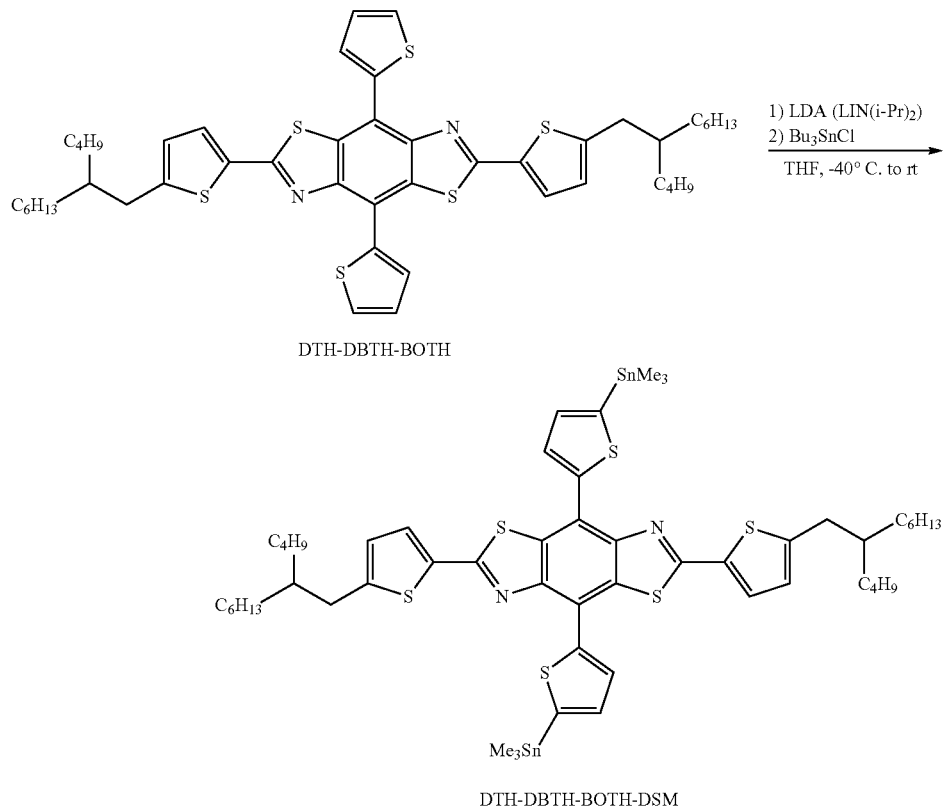

Example 19

2,6-bis[5-(2-hexyldecyl)thiophene-2-yl]-4,8-bis(5-trimethylstannylthiophene-2-yl-benzo[1,2-d; 4,5-d']bisthiazole (DTH-DBTH-HDTH-DSM)

[Chemical Formula 89]

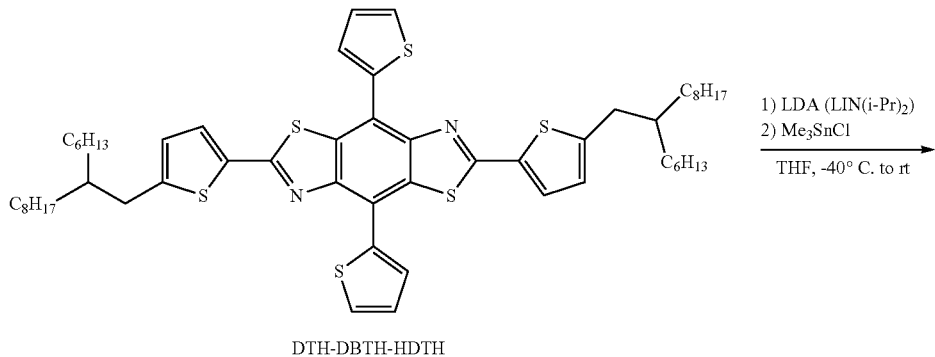

DTH-DBTH-HDTH

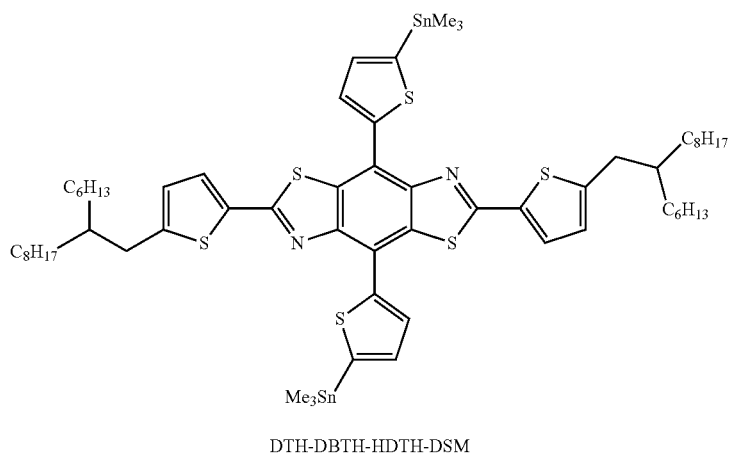

DTH-DBTH-HDTH-DSM 2,6-bis[5-(2-hexyldecyl)thiophene-2-yl]-4,8-dithiophene-2-yl-benzo[1,2-d; 4,5-d']bisthiazole (DTH-DBTH-HDTH, 700 mg, 0.72 mmol) and tetrahydrofuran (14 mL) were added in a 30 mL flask, and cooled to −50° C., lithium diisopropylamide (2 M solution, 0.79 mL, 1.58 mmol) was added dropwise, and the mixture was stirred for 30 minutes. Thereafter, trimethyltin chloride (1 M solution, 16 mL, 1.58 mmol) was added, and the mixture was heated to room temperature, and stirred for 2 hours. After the reaction was completed, water was added, the mixture was extracted twice with toluene, and the organic layer was washed with water, and then dried with anhydrous magnesium sulfate. Then, the organic layer was filtered and concentrated to obtain a crude product, and the crude product was purified by GPC-HPLC (JAIGEL-1H, 2H, chloroform) to prepare 518 mg of 2,6-bis[5-(2-hexyldecyl)thiophene-2-yl]-4,8-bis(5-trimethylstannylthiophene-2-yl)-benzo[1,2-d; 4,5-d']bisthiazole (DTH-DBTH-HDTH-DSM) as a yellow solid (yield 55%).

Generation of an intended compound was confirmed by $^1$H-NMR measurement.

$^1$H NMR (400 MHz, CDCl$_3$): δ8.16 (d, J=3.6 Hz, 2H), 7.56 (d, J=3.6 Hz, 2H), 7.37 (d, J=3.6 Hz, 2H), 6.82 (d, J=3.6 Hz, 2H), 2.82 (m, 4H), 1.71 (m, 2H), 1.35-1.25 (m, 48H), 0.88 (t J=6.4 Hz, 6H), 0.87 (t, J=6.4 Hz, 6H), 0.47 (s, 18H).

Example 20

2,6-bis[5-(2-hexyldecyl)thiophene-2-yl]-4,8-bis(5-tributylstannylthiophene-2-yl)-benzo[1,2-d; 4,5-d']bisthiazole (DTH-DBTH-HDTH-DSB)

[Chemical Formula 90]

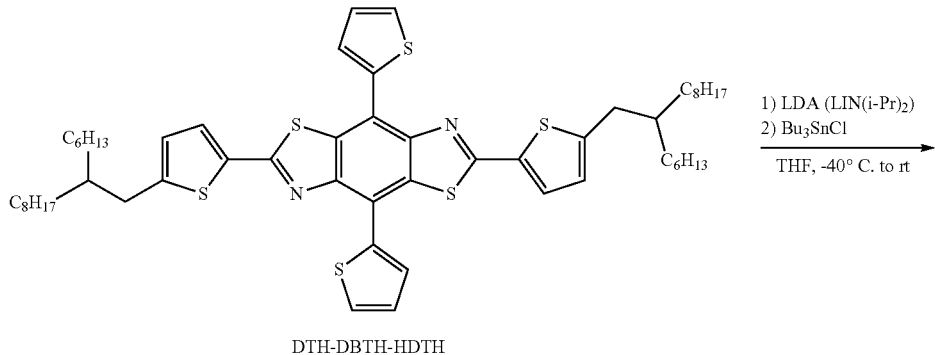

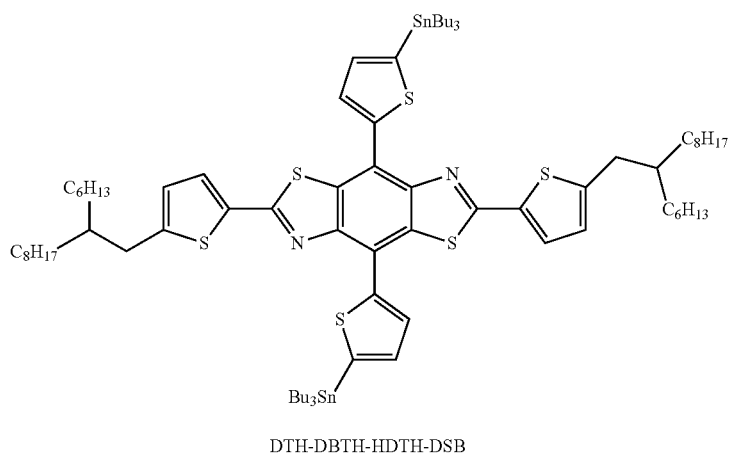

2,6-bis[5-(2-hexyldecyl)thiophene-2-yl]-4,8-dithiophene-2-yl-benzo[1,2-d; 4,5-d']bisthiazole (DTH-DBTH-HDTH, 602 mg, 0.62 mmol) and tetrahydrofuran (18 mL) were added in a 50 mL flask, and cooled to −40° C., lithium diisopropylamide (2 M solution, 0.65 mL, 1.30 mmol) was added dropwise, and the mixture was stirred for 30 minutes. Thereafter, tributyltin chloride (352 μL, 1.30 mmol) was added, and the mixture was heated to room temperature, and stirred for 2 hours. After the reaction was completed, water was added, the mixture was extracted twice with toluene, and the organic layer was washed with water, and then dried with anhydrous magnesium sulfate. Then, the organic layer was filtered and concentrated to obtain a crude product, and the crude product was purified by GPC-HPLC (JAIGEL-1H, 2H, chloroform) to prepare 634 mg of 2,6-bis[5-(2-hexyldecyl)thiophene-2-yl]-4,8-bis(5-tributylstannylthiophene-2-yl)-benzo[1,2-d; 4,5-d']bisthiazole (DTH-DBTH-HDTH-DSB) as a brown oil (yield 66%).

Generation of an intended compound was confirmed by $^1$H-NMR measurement.

$^1$H NMR (400 MHz, $C_6D_6$): δ 8.47 (d, J=3.6 Hz, 2H), 7.47 (d, J=3.6 Hz, 2H), 7.33 (d, J=3.6 Hz, 2H), 6.54 (d, J=3.6 Hz, 2H), 2.64 (m, 4H), 1.78-1.68 (m, 14H), 1.44 (m, 12H), 1.35-1.22 (m, 60H), 0.97 (t, J=6.8 Hz, 18H), 0.91 (d, J=7.2 Hz, 12H), 0.89 (d, J=6.4 Hz, 6H).

Example 21

2,6-bis[5-(2-decyltetradecyl)thiophene-2-yl]-4,8-bis (5-trimethylstannylthiophene-2-yl)-benzo[1,2-d; 4,5-d']bisthiazole (DTH-DBTH-TDTH-DSM)

[Chemical Formula 91]

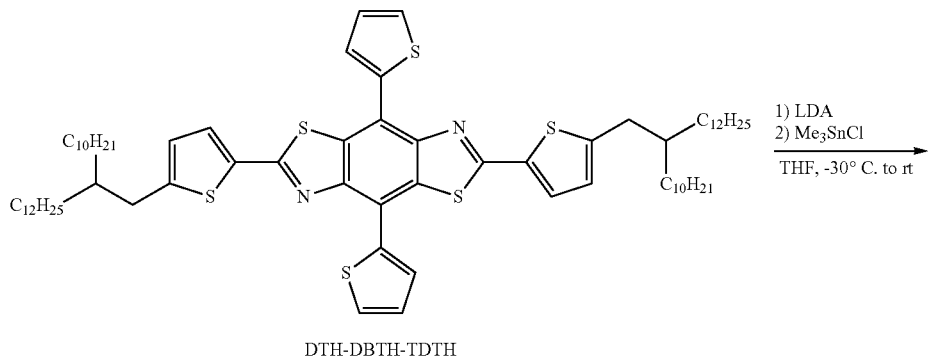

DTH-DBTH-TDTH

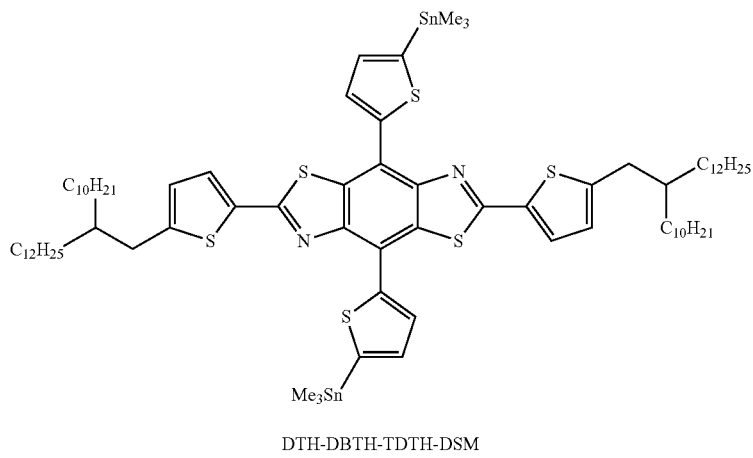

DTH-DBTH-TDTH-DSM 2,6-bis[5-(2-decyltetradecyl)thiophene-2-yl]-4,8-dithiophene-2-yl-benzo[1,2-d; 4,5-d']bisthiazole (DTH-DBTH-TDTH, 1.5 g, 1.26 mmol) and tetrahydrofuran (50 mL) were added in a 30 mL flask, and cooled to −30° C., lithium diisopropylamide (2 M solution, 1.38 mL, 2.77 mmol) was added dropwise, and the mixture was stirred for 30 minutes. Thereafter, trimethyltin chloride (1 M solution, 3.0 mL, 3.02 mmol) was added, and the mixture was heated to room temperature, and stirred for 2 hours. After the reaction was completed, water was added, the mixture was extracted twice with toluene, and the organic layer was washed with water, and then dried with anhydrous magnesium sulfate. Then, the organic layer was filtered and concentrated to obtain a crude product, and the crude product was purified by GPC-HPLC (JAIGEL-1H, 2H, chloroform) to prepare 1.28 g of 2,6-bis[5-(2-decyltetradecyl)thiophene-2-yl]-4,8-bis(5-trimethylstannylthiophene-2-yl)-benzo[1,2-d; 4,5-d']bisthiazole (DTH-DBTH-TDTH-DSM) as a yellow solid (yield 67%).

Generation of an intended compound was confirmed by $^1$H-NMR measurement.

$^1$H NMR (400 MHz, CDCl$_3$): δ 8.15 (d, J=3.6 Hz, 2H), 7.56 (d, J=3.6 Hz, 2H), 7.35 (d, J=3.6 Hz, 2H), 6.84 (d, J=3.6 Hz, 2H), 2.82 (m, 4H), 1.71 (m, 2H), 1.39-1.20 (m, 80H), 0.88 (t J=6.4 Hz, 6H), 0.86 (t, J=6.4 Hz, 12H), 0.47 (s, 18H).

Example 22

Synthesis of P-TDMOT-DBTH-O-IMTH

[Chemical Formula 92]

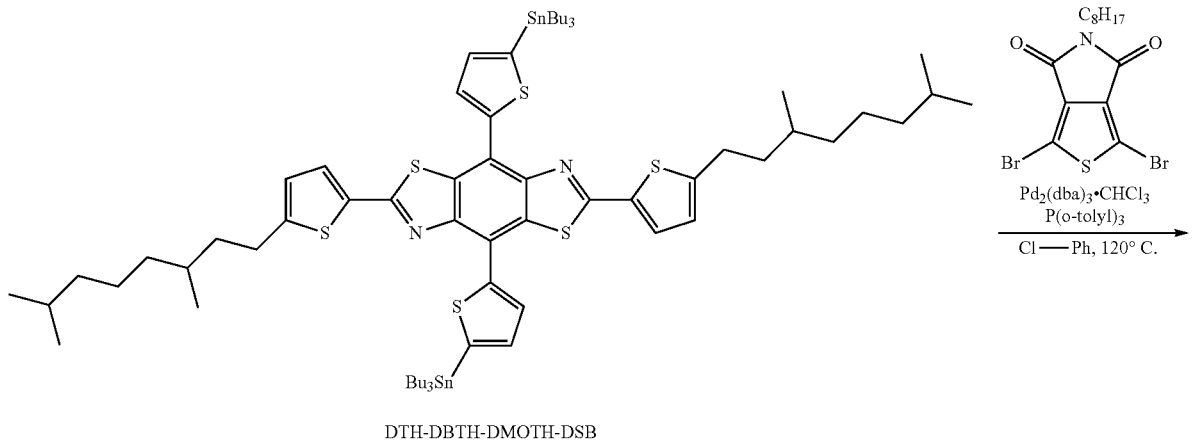

DTH-DBTH-DMOTH-DSB

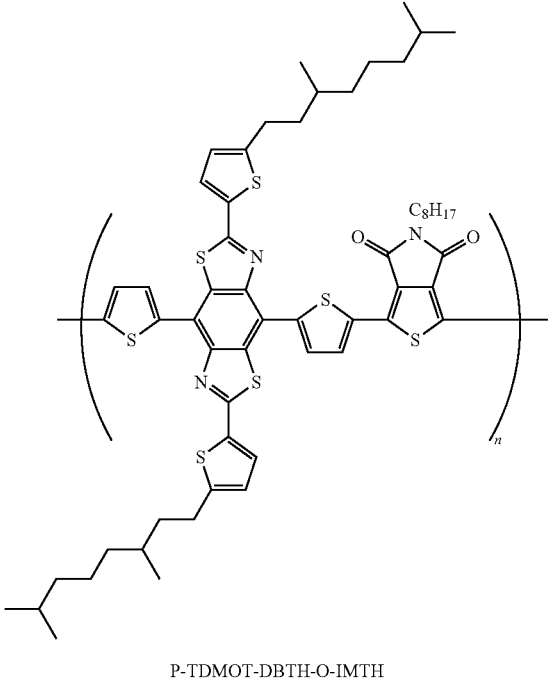

P-TDMOT-DBTH-O-IMTH 2,6-bis[5-(3,7-dimethyloctyl)thiophene-2-yl]-4,8-bis(5-tributylstannylthiophene-2-yl)-benzo[1,2-d; 4,5-d']bisthiazole (DTH-DBTH-DMOTH-DSB, 113 mg, 0.08 mmol), 1,3-dibromo-5-octylthieno[3,4-c]pyrrolo-4,6-dione (O-IMTH-DB, 35 mg, 0.08 mmol), a tris(dibenzylideneacetone)dipalladium (0)-chloroform adduct (3 mg, 3.3 μmol), tris(o-tolyl)phosphine (4 mg, 13 μmol) and chlorobenzene (10 mL) were added in a 20 mL flask, and reacted at 120° C. for 24 hours. After the reaction was completed, the reaction liquid was added to methanol (50 mL), the precipitated solid was collected by filtration, and the obtained solid was subjected to Soxhlet washing (methanol, acetone and hexane). Then, the solid was subjected to Soxhlet extraction (chloroform) to prepare 71 mg (69%) of P-TDMOT-DBTH-O-IMTH as a black solid. The ultraviolet-visible absorption spectrum is shown in FIG. 1.

Ionization potential: 5.24 eV (HOMO −5.24 eV)

Example 23

Synthesis of P-THDT-DBTH-EH-IMTH

[Chemical Formula 93]

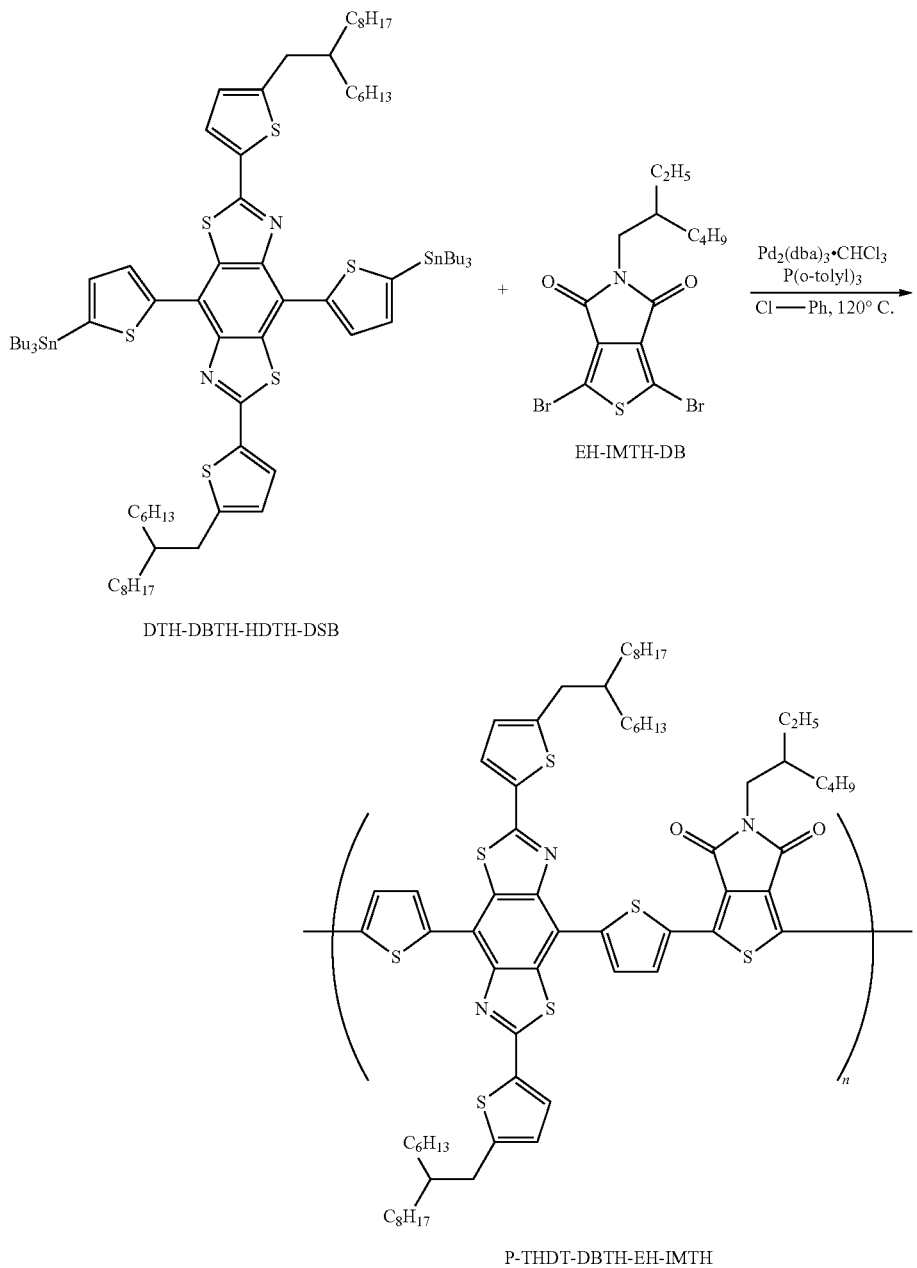

2,6-bis[5-(2-hexyldecyl)thiophene-2-yl]-4,8-bis(5-tributylstannylthiophene-2-yl)-benzo[1,2-d; 4,5-d']bisthiazole (DTH-DBTH-HDTH-DSB, 150 mg, 0.10 mmol), 1,3-dibromo-5-(2-ethylhexyl)thieno[3,4-c]pyrrolo-4,6-dione (EH-IMTH-DB, 41 mg, 0.10 mmol), a tris(dibenzylideneacetone) dipalladium (0)-chloroform adduct (4 mg, 3.9 μmol), tris(o-tolyl)phosphine (5 mg, 15.5 μmol) and chlorobenzene (12 mL) were added in a 20 mL flask, and reacted at 120° C. for 22 hours. After the reaction was completed, the reaction liquid was added to methanol (60 mL), the precipitated solid was collected by filtration, and the obtained solid was subjected to Soxhlet washing (methanol, acetone and hexane). Then, the solid was subjected to Soxhlet extraction (chloroform) to prepare 109 mg (91%) of P-THDT-DBTH-EH-IMTH as a black solid. The ultraviolet-visible absorption spectrum is shown in FIG. 2.

Ionization potential: 5.36 eV (HOMO −5.36 eV)

GPC measurement result: Mw (weight average molecular weight): 68000

Mn (number average molecular weight): 21100

Preparation and evaluation of photoelectric conversion element P-THDT-DBTH-EH-IMTH prepared as described above was used as a donor material, and PCBM (C61) (phenyl C61-methyl butylate ester) was used as an acceptor material. The donor material and acceptor material (weight ratio: 1:2) (total concentration: 24 mg/mL) and 1,8-diiodooctane (0.03 mL/mL) were dissolved in chlorobenzene, and the solution was made to pass through a 0.45 μm-filter to obtain a mixed solution.

A glass substrate with ITO deposited thereon was surface-treated by subjecting the glass substrate to an ozone UV treatment, and PEDOT-PSS ([poly(3,4-ethylenedioxythiophene)-poly(styrenesulfonic acid)) was applied using a spin coater. Next, the donor material/acceptor material mixed solution was deposited using a spin coater, and dried under a reduced pressure at room temperature. An ethanol solution of titanium isopropoxide (about 0.3 v %) was applied by spin coating to form a film thereon which was converted into a titanium oxide film by moisture in the atmosphere. Thereafter, aluminum was vapor-deposited as an electrode to obtain a device.

Properties were evaluated using a solar simulator (CEP 2000; AM 1.5 G filter; radiation intensity: 100 mW/cm$^2$; manufactured by JASCO Corporation) with the obtained device. The results showed that the Jsc (short-circuit current density) was 8.64 mA/cm$^2$, the Voc (open circuit voltage) was 0.86 V, the FF (fill factor) was 0.58, and the conversion efficiency was 4.34%.

Example 24

Synthesis of P-THDT-DBTH-O-IMTH

[Chemical Formula 94]

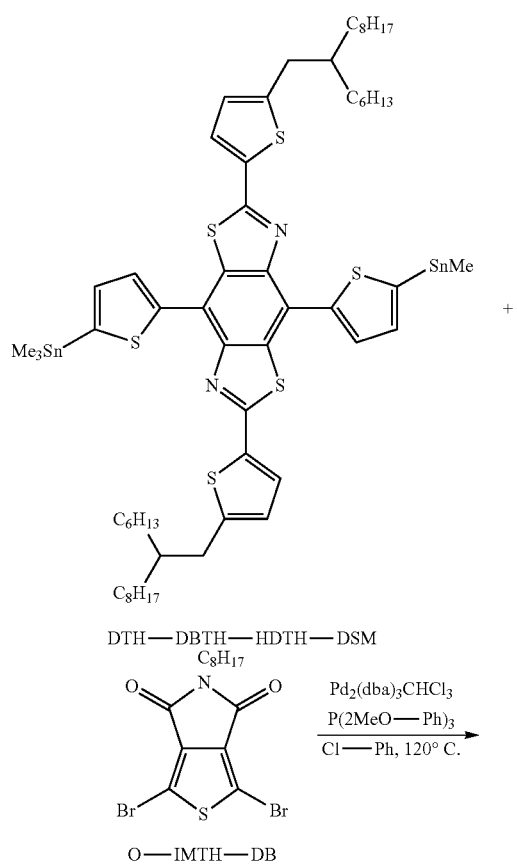

DTH—DBTH—HDTH—DSM

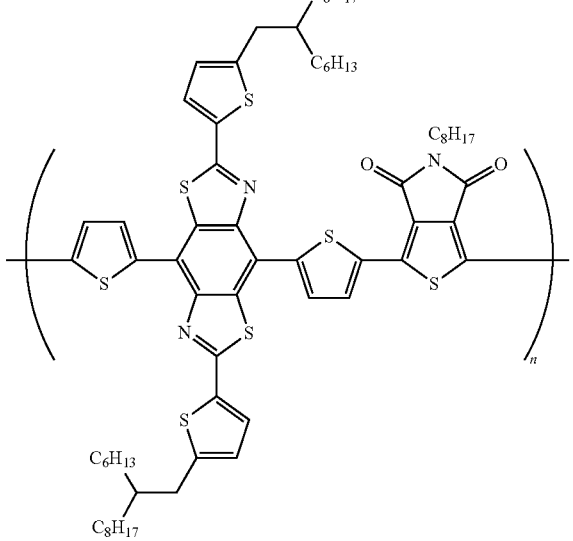

P—THDT—DBTH—O—IMTH 2,6-bis[5-(2-hexyldecyl)thiophene-2-yl]-4,8-bis(5-trimethylstannylthiophene-2-yl)-benzo[1,2-d 4,5-d']bisthiazole (DTH-DBTH-HDTH-DSM, 90 mg, 0.07 mmol), 1,3-dibromo-5-octylthieno[3,4-c]pyrrolo-4,6-dione (O-IMTH-DB, 30 mg, 0.07 mmol), a tris(dibenzylideneacetone)dipalladium (0)-chloroform adduct (3 mg, 2.8 μmol), tris(2-methoxyphenyl)phosphine (4 mg, 11.1 μmol) and chlorobenzene (7 mL) were added in a 20 mL flask, and reacted at 120° C. for 24 hours. After the reaction was completed, the reaction liquid was added to methanol (50 mL), the precipitated solid was collected by filtration, and the obtained solid was subjected to Soxhlet washing (methanol, acetone and hexane). Then, the solid was subjected to Soxhlet extraction (chloroform) to prepare 74 mg (87%) of P-THDT-DBTH-O-IMTH as a black solid. The ultraviolet-visible absorption spectrum is shown in FIG. 3.

Ionization potential: 5.25 eV (HOMO −5.25 eV)

GPC measurement result: Mw (weight average molecular weight): 34000

Mn (number average molecular weight): 12700

Preparation and Evaluation of Photoelectric Conversion Element

Except that P-THDT-DBTH-O-IMTH prepared as described above was used in place of P-THDT-DBTH-EH-IMTH, the same procedure as in Example 23 was carried out to prepare a device. Properties were evaluated using a solar simulator (CEP 2000; AM 1.5 G filter; radiation intensity: 100 mW/cm$^2$; manufactured by JASCO Corporation) with the obtained device. The results showed that the Jsc (short-circuit current density) was 7.51 mA/cm$^2$, the Voc (open circuit voltage) was 0.79 V, the FF (fill factor) was 0.70, and the conversion efficiency was 4.13%.

Example 25

Synthesis of P-TEHT-DBTH-HD-IMTH

[Chemical Formula 95]

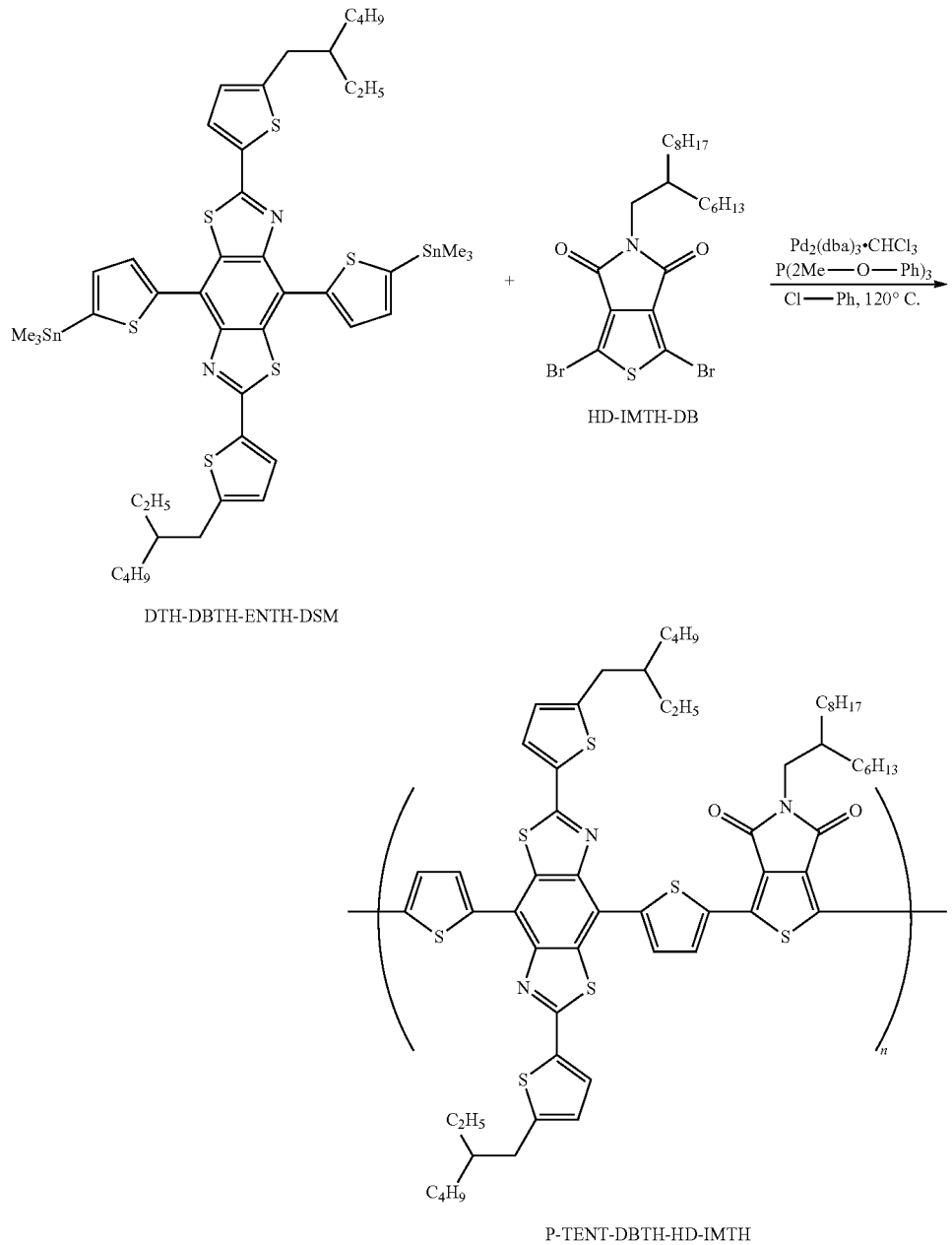

2,6-bis[5-(2-hexyldecyl)thiophene-2-yl]-4,8-bis(5-trimethylstannylthiophene-2-yl)-benzo[1,2-d; 4,5-d']bisthiazole (DTH-DBTH-EHTH-DSM, 100 mg, 0.09 mmol), 1,3-dibromo-5-(2-hexyldecyl)thieno[3,4-c]pyrrolo-4,6-dione (HD-IMTH-DB, 50 mg, 0.09 mmol), a tris(dibenzylideneacetone)dipalladium (0)-chloroform adduct (4 mg, 3.7 μmol), tris(2-methoxyphenyl)phosphine (6 mg, 14.9 μmol) and chlorobenzene (7 mL) were added in a 20 mL flask, and reacted at 120° C. for 24 hours. After the reaction was completed, the reaction liquid was added to methanol (40 mL), the precipitated solid was collected by filtration, and the obtained solid was subjected to Soxhlet washing (methanol, acetone and hexane). Then, the solid was subjected to Soxhlet extraction (chloroform) to prepare 39 mg (37%) of P-TEHT-DBTH-HD-IMTH as a black solid. The ultraviolet-visible absorption spectrum is shown in FIG. 4.

Ionization potential: 5.25 eV (HOMO −5.25 eV)
GPC measurement result: Mw (weight average molecular weight): 15900
Mn (number average molecular weight): 8100

Preparation and Evaluation of Photoelectric Conversion Element

Except that P-TEHT-DBTH-HD-IMTH prepared as described above was used in place of P-THDT-DBTH-EH-IMTH, the same procedure as in Example 23 was carried out to prepare a device. Properties were evaluated using a solar simulator (CEP 2000; AM 1.5 G filter; radiation intensity: 100 mW/cm², manufactured by JASCO Corporation) with the obtained device. The results showed that the Jsc (short-circuit current density) was 5.55 mA/cm², the Voc (open circuit voltage) was 0.78 V, the FF (fill factor) was 0.64, and the conversion efficiency was 2.81%.

Example 26

Synthesis of P-TBOT-DBTH-DMO-IMTH bromo-5-(3,7-dimethyloctyl)thieno[3,4-c]pyrrolo-4,6-dione (DMO-IMTH-DB, 38 mg, 0.09 mmol), a tris(dibenzylideneacetone)dipalladium (0)-chloroform adduct (4 mg, 3.6 μmol), tris(2-methoxyphenyl)phosphine (5 mg, 14.4 μmol) and chlorobenzene (8 mL) were added in a 20 mL flask, and reacted at 120° C. for 24 hours. After the reaction was completed, the reaction liquid was added to methanol (40 mL), the precipitated solid was collected by filtration, and the obtained solid was subjected to Soxhlet washing (methanol, acetone and hexane). Then, the solid was subjected to Soxhlet extraction (chloroform) to prepare 26 mg (27%) of

[Chemical Formula 96]

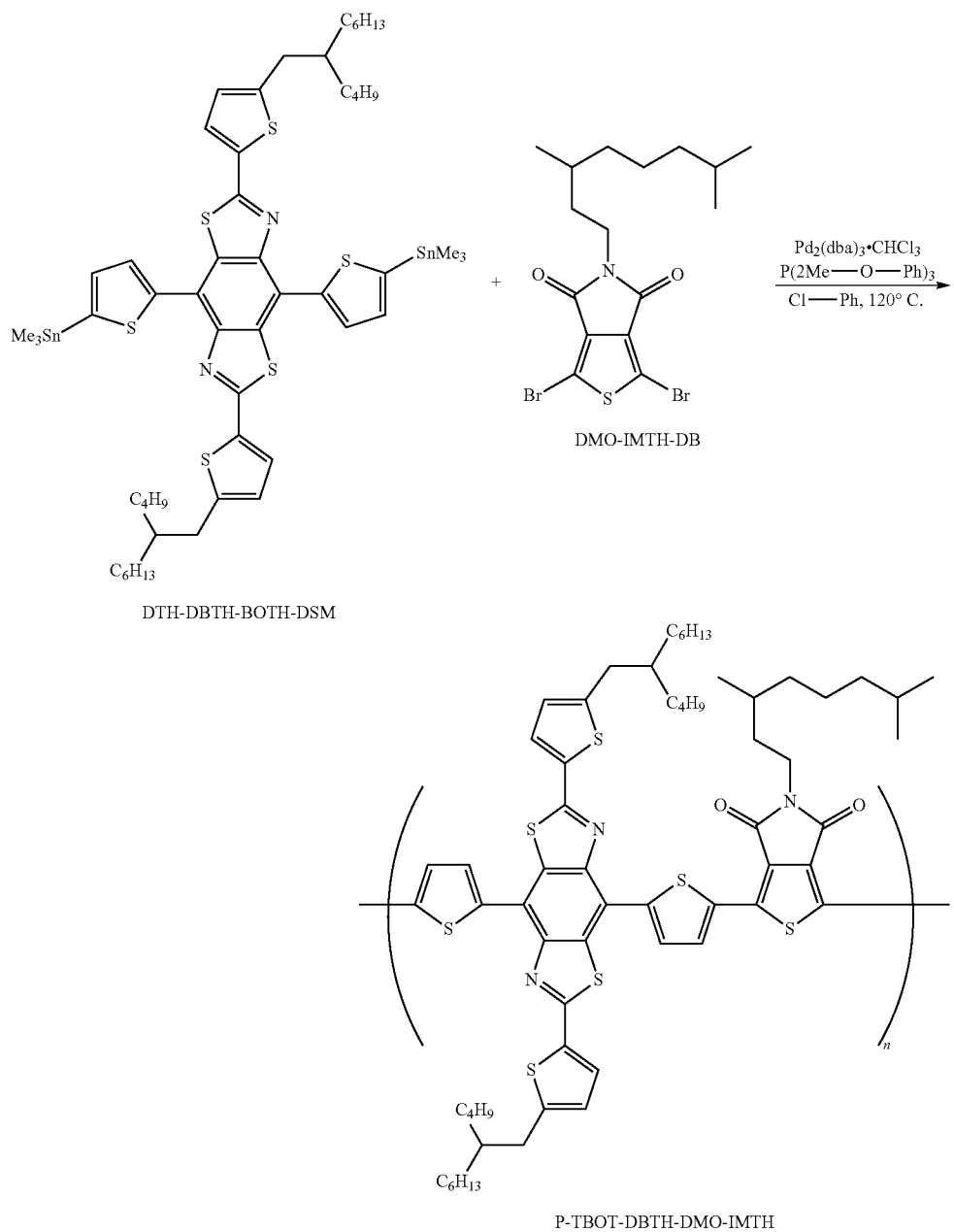

2,6-bis[5-(2-butyloctyl)thiophene-2-yl]-4,8-bis(5-trimethylstannylthiophene-2-yl)-benzo[1,2-d; 4,5-d']bisthiazole (DTH-DBTH-BOTH-DSM, 100 mg, 0.09 mmol), 1,3-di- P-TBOT-DBTH-DMO-IMTH as a black solid. The ultraviolet-visible absorption spectrum is shown in FIG. 5.

Ionization potential: 5.23 eV (HOMO −5.23 eV)

Example 27

Synthesis of P-TEHT-DBTH-ODD-IMTH

[Chemical Formula 97]

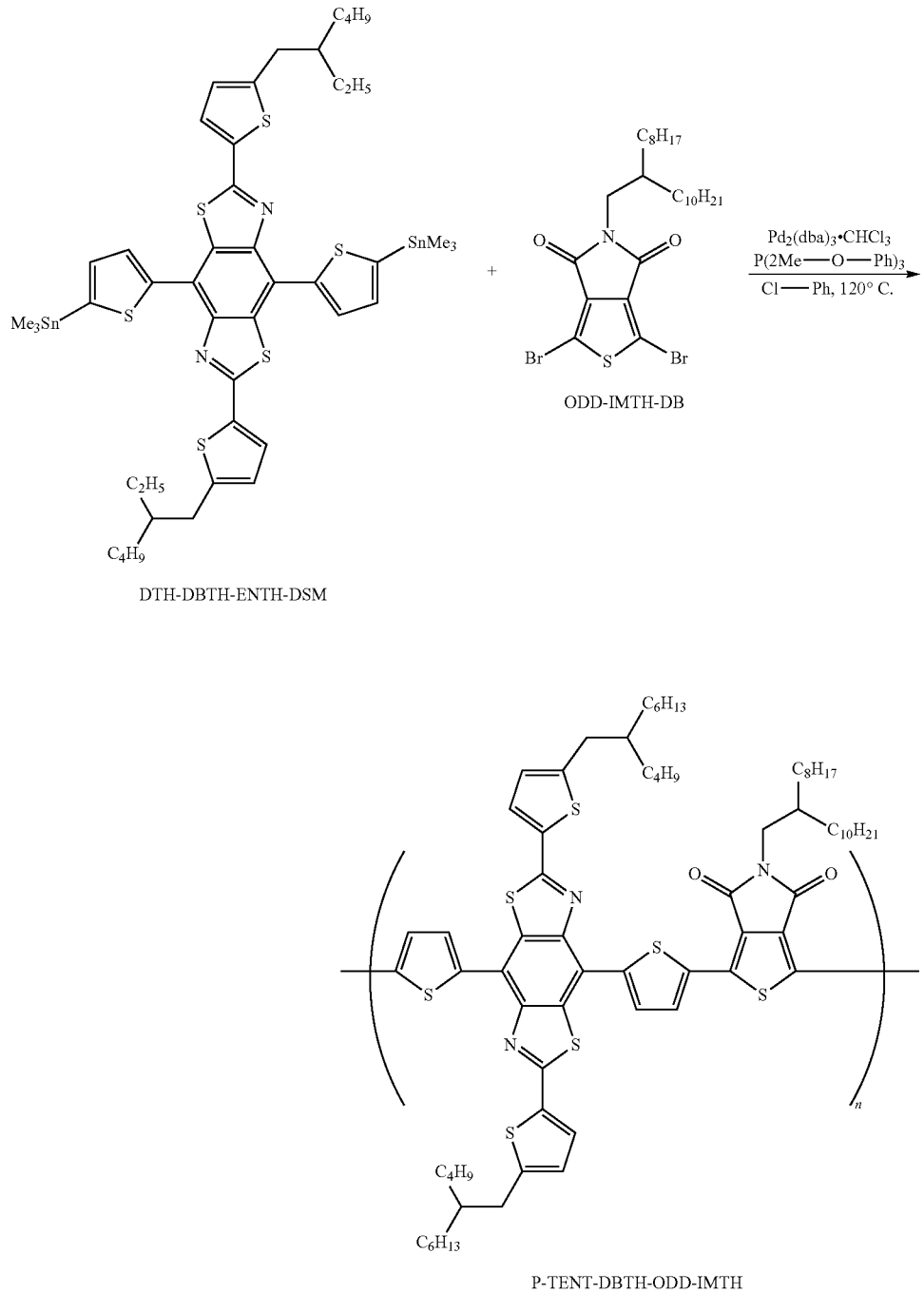

2,6-bis[5-(2-hexyldecyl)thiophene-2-yl]-4,8-bis(5-trimethylstannylthiophene-2-yl)-benzo[1,2-d; 4,5-d']bisthiazole (DTH-DBTH-EHTH-DSM, 100 mg, 0.09 mmol), 1,3-dibromo-5-(2-octyldodecyl)thieno[3,4-c]pyrrolo-4,6-dione (ODD-IMTH-DB, 55 mg, 0.09 mmol), a tris(dibenzylideneacetone)dipalladium (0)-chloroform adduct (4 mg, 3.7 μmol), tris(2-methoxyphenyl)phosphine (6 mg, 14.9 μmol) and chlorobenzene (7 mL) were added in a 20 mL flask, and reacted at 120° C. for 24 hours. After the reaction was completed, the reaction liquid was added to methanol (40 mL), the precipitated solid was collected by filtration, and the obtained solid was subjected to Soxhlet washing (methanol, acetone and hexane). Then, the solid was subjected to Soxhlet extraction (chloroform) to prepare 91 mg (76%) of P-TEHT-DBTH-ODD-LMTH as a black solid. The ultraviolet-visible absorption spectrum is shown in FIG. 6.

Ionization potential: 5.27 eV (HOMO −5.27 eV)

Example 28

Synthesis of P-TDMOT-DBTH-TDZ

[Chemical Formula 98]

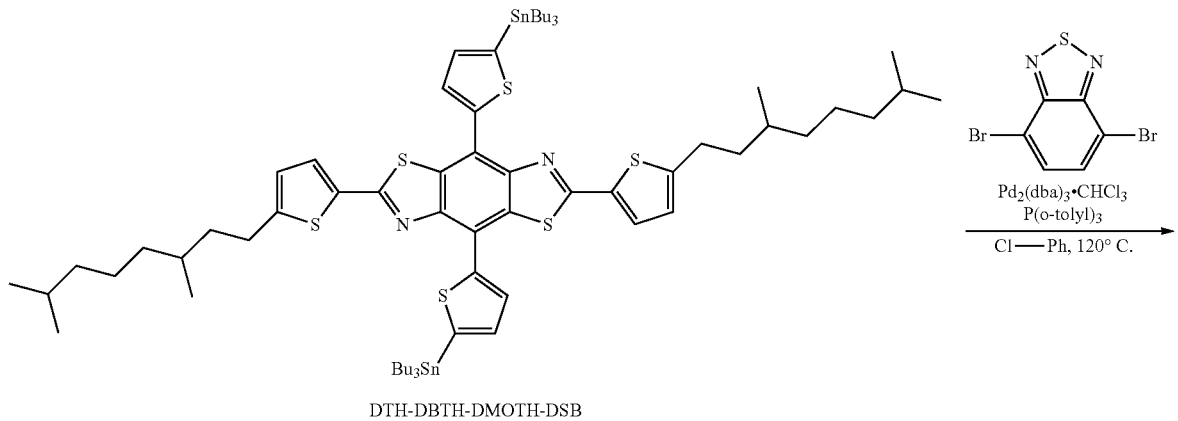

DTH-DBTH-DMOTH-DSB

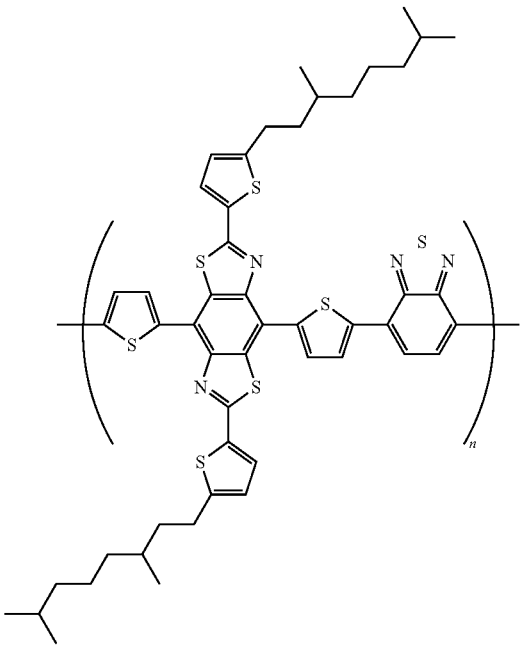

P-TDMOT-DBTH-TDZ 2,6-bis[5-(3,7-dimethyloctyl)thiophene-2-yl]-4,8-bis(5-tributylstannylthiophene-2-yl)-benzo[1,2-d; 4,5-d']bisthiazole (DTH-DBTH-DMOTH-DSB, 122 mg, 0.09 mmol), 4,7-dibromobenzo[1,2,5]thiadiazole (TDZ-DB, 26 mg, 0.09 mmol), a tris(dibenzylideneacetone)dipalladium (0)-chloroform adduct (4 mg, 3.5 μmol), tris(o-tolyl)phosphine (4 mg, 14.0 μmol) and chlorobenzene (10 mL) were added in a 20 mL flask, and reacted at 120° C. for 24 hours. After the reaction was completed, the reaction liquid was added to methanol (50 mL), the precipitated solid was collected by filtration, and the obtained solid was subjected to Soxhlet washing (methanol, acetone and hexane). Then, the solid was subjected to Soxhlet extraction (chloroform) to prepare 31 mg (38%) of P-TDMOT-DBTH-TDZ as a black solid. The ultraviolet-visible absorption spectrum is shown in FIG. 7.

Ionization potential: 5.11 eV (HOMO −5.11 eV)

Example 29

Synthesis of P-THDT-DBTH-FFTDZ

[Chemical Formula 99]

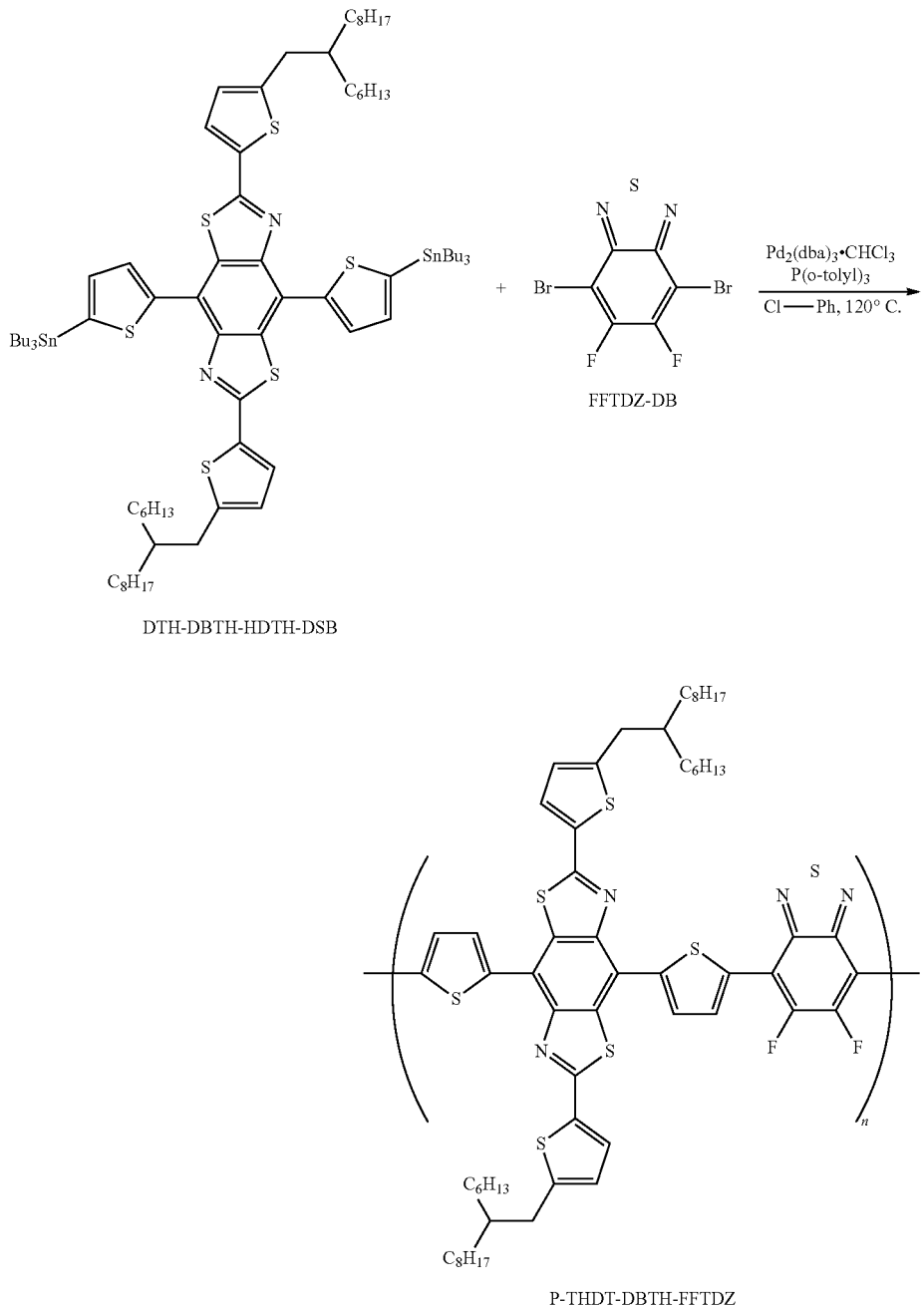

2,6-bis[5-(2-hexydecyl)thiophene-2-yl]-4,8-bis(5-tributylstannylthiophene-2-yl)-benzo[1,2-d; 4,5-d']bisthiazole (DTH-DBTH-HDTH-DSB, 122 mg, 0.08 mmol), 4,7-dibromo-5,6-difluorobenzo[1,2,5]thiadiazole (FFTDZ-DB, 28 mg, 0.08 mmol), a tris(dibenzylideneacetone)dipalladium (0)-chloroform adduct (4 mg, 3.4 μmol), tris(o-tolyl)phosphine (4 mg, 13.4 μmol) and chlorobenzene (10 mL) were added in a 20 mL flask, and reacted at 120° C. for 23 hours. After the reaction was completed, the reaction liquid was added to methanol (50 mL), the precipitated solid was collected by filtration, and the obtained solid was subjected to Soxhlet washing (methanol, acetone and hexane). Then, the solid was subjected to Soxhlet extraction (chloroform) to prepare 27 mg (29%) of P-THDT-DBTH-FFTDZ as a black solid. The ultraviolet-visible absorption spectrum is shown in FIG. 8.

Ionization potential: 5.55 eV (HOMO −5.55 eV)

GPC measurement result: Mw (weight average molecular weight): 4500

Mn (number average molecular weight): 3300

Example 30

Synthesis of P-THDT-DBTH-DMO-DPP

[Chemical Formula 100]

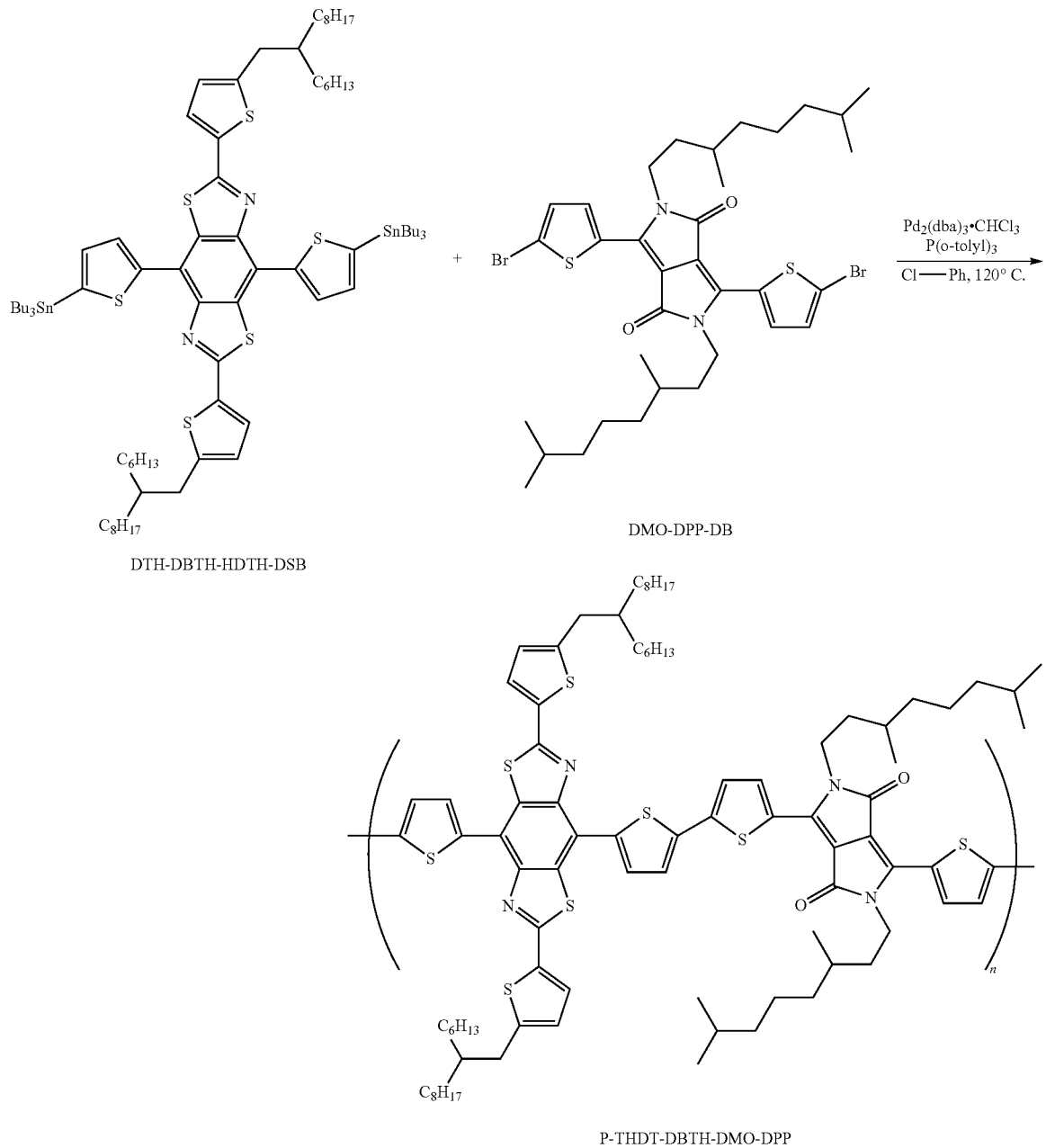

2,6-bis[5-(2-hexydecyl)thiophene-2-yl]-4,8-bis(5-tributylstannylthiophene-2-yl)-benzo[1,2-d; 4,5-d']bisthiazole (DTH-DBTH-HDTH-DSB, 100 mg, 0.06 mmol), 3,6-bis(5-bromothiophene-2-yl)-2,5-(3,7-dimethyloctyl)-2,5-dihydropyrrolo[3,4-c]pyrrole-1,4-dione (DMO-DPP-DB, 49 mg, 0.06 mmol), a tris(dibenzylideneacetone)dipalladium (0)-chloroform adduct (3 mg, 2.6 μmol), tris(o-tolyl)phosphine (3 mg, 10.4 μmol) and chlorobenzene (10 mL) were added in a 20 mL flask, and reacted at 120° C. for 23 hours. After the reaction was completed, the reaction liquid was added to methanol (60 mL), the precipitated solid was collected by filtration, and the obtained solid was subjected to Soxhlet washing (methanol, acetone and hexane). Then, the solid was subjected to Soxhlet extraction (chloroform) to prepare 26 mg (26%) of P-THDT-DMO-DPP as a black solid. The ultraviolet-visible absorption spectrum is shown in FIG. 9.

Ionization potential: 5.10 eV (HOMO −5.10 eV)

GPC measurement result: Mw (weight average molecular weight): 6100

Mn (number average molecular weight): 3600

Preparation and Evaluation of Photoelectric Conversion Element

P-THDT-DBTH-DMO-DPP prepared as described above was used as a donor material, and PCBM (C61) (phenyl C61-methyl butylate ester) was used as an acceptor material. The donor material and acceptor material (weight ratio: 1:2) (total concentration: 24 mg/mL) and 1,8-diiodooctane (0.03 mL/mL) were dissolved in ortho-dichlorobenzene, and the solution was made to pass through a 0.45 μm-filter to obtain a mixed solution.

A glass substrate with ITO deposited thereon was surface-treated by subjecting the glass substrate to an ozone UV treatment, and PEDOT-PSS ([poly(3,4-ethylenedioxythiophene)-poly(styrenesulfonic acid)) was applied using a spin coater. Next, the donor material/acceptor material mixed solution was deposited using a spin coater, and dried under a reduced pressure at room temperature. An ethanol solution of titanium isopropoxide (about 0.3 v %) was applied by spin coating to form a film thereon which was converted into a titanium oxide film by moisture in the atmosphere. Thereafter, aluminum was vapor-deposited as an electrode to obtain a device.

Properties were evaluated using a solar simulator (CEP 2000; AM 1.5 G filter; radiation intensity: 100 mW/cm$^2$; manufactured by JASCO Corporation) with the obtained device. The results showed that the Jsc (short-circuit current density) was 6.66 mA/cm$^2$, the Voc (open circuit voltage) was 0.45 V, the FF (fill factor) was 0.62, and the conversion efficiency was 2.02%.

Example 31

Synthesis of P-THDT-DBTH-EH-OFTT

[Chemical Formula 101]

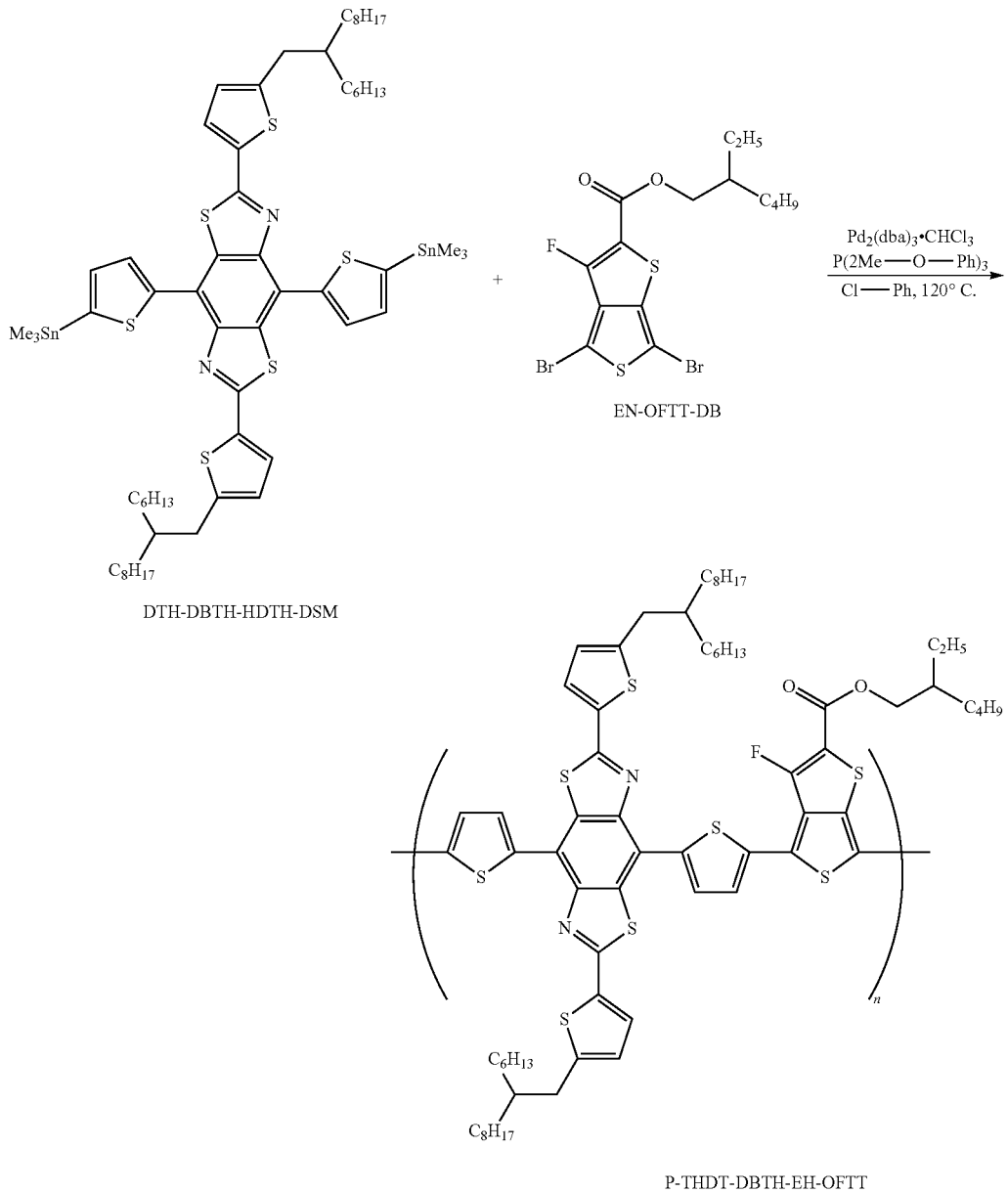

2,6-bis[5-(2-hexydecyl)thiophene-2-yl]-4,8-bis(5-trimethylstannylthiophene-2-yl)-benzo[1,2-d; 4,5-d']bisthiazole (DTH-DBTH-HDTH-DSM, 90 mg, 0.07 mmol), 4,6-dibromo-3-fluorothieno[3,4-b]thiophene-2-carboxylic acid(2-ethylhexyl)ester (EH-OFTT-DB, 33 mg, 0.07 mmol), a tris(dibenzylideneacetone)dipalladium (0)-chloroform adduct (3 mg, 2.1 μmol), tris(2-methoxyphenyl)phosphine (4 mg, 8.4 μmol) and chlorobenzene (7 mL) were added in a 20 mL flask, and reacted at 120° C. for 24 hours. After the reaction was completed, the reaction liquid was added to methanol (40 mL), the precipitated solid was collected by filtration, and the obtained solid was subjected to Soxhlet washing (methanol, acetone and hexane). Then, the solid was subjected to Soxhlet extraction (chloroform) to prepare 80 mg (87%) of P-THDT-DBTH-EH-OFTT as a black solid. The ultraviolet-visible absorption spectrum is shown in FIG. 10.

Ionization potential: 5.10 eV (HOMO −5.10 eV)

GPC measurement result: Mw (weight average molecular weight): 6700

Mn (number average molecular weight): 4800

Example 32

Synthesis of P-TTDT-DBTH-EHP-IMTH

[Chemical Formula 102]

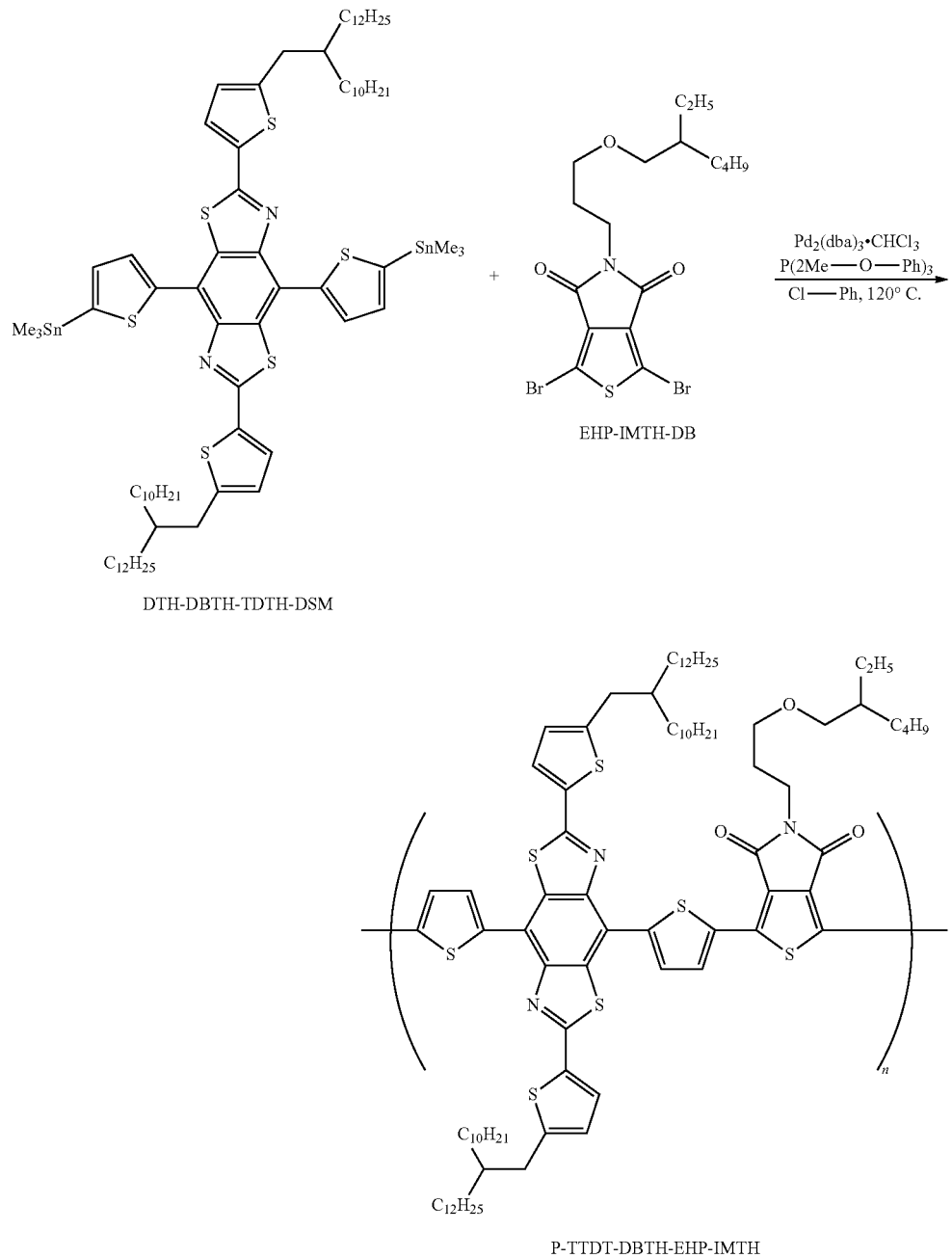

2,6-bis[5-(2-decyltetradecyl)thiophene-2-yl]-4,8-bis(5-trimethylstannylthiophene-2-yl)-benzo[1,2-d; 4,5-d']bisthiazole (DTH-DBTH-TDTH-DSM, 100 mg, 0.07 mmol), 1,3-dibromo-5-(2-ethylhexyloxy)thieno[3,4-c]pyrrolo-4,6-dione (EHP-IMTH-DB, 33 mg, 0.07 mmol), a tris (dibenzylideneacetone)dipalladium (0)-chloroform adduct (3 mg, 2.6 μmol), tris(2-methoxyphenyl)phosphine (4 mg, 10.5 μmol) and chlorobenzene (7 mL) were added in a 20 mL flask, and reacted at 120° C. for 24 hours. After the reaction was completed, the reaction liquid was added to methanol (40 mL), the precipitated solid was collected by filtration, and the obtained solid was subjected to Soxhlet washing (methanol, acetone and hexane). Then, the solid was subjected to Soxhlet extraction (chloroform) to prepare 79 mg (79%) of P-TTDT-DBTH-EHP-IMTH as a black solid. The ultraviolet-visible absorption spectrum is shown in FIG. 11.

Ionization potential: 5.30 eV (HOMO −5.30 eV)
GPC measurement result: Mw (weight average molecular weight): 20200
Mn (number average molecular weight): 10300

Example 33

Synthesis of 2,6-bis[5-(3,7-dimethyloctyl)thiophene-2-yl]-4,8-bisthiazole-2-yl-benzo[1,2-d; 4,5-d']bisthiazole (DTHA-DBTH-DMOTH)

2,6-bis[5-(3,7-dimethyloctyl)thiophene-2-yl]-4,8-diiodo-benzo[1,2-d; 4,5-d']bisthiazole (DI-DBTH-DMOTH, 250 mg, 0.28 mmol), 2-tributylstannylthiazole (263 mg, 0.70 mmol), tris(2-furyl)phosphine (12 mg, 11 μmol), a tris (dibenzylideneacetone)dipalladium (0)-chloroform adduct (10 mg, 45 μmol) and N,N-dimethylformamide (5 mL) were added in a 20 mL flask, and reacted at 80° C. for 24 hours. After the reaction was completed, the reaction product was cooled to room temperature, water was then added, the mixture was extracted twice with chloroform, and the organic layer was washed with water, and then dried with anhydrous magnesium sulfate. The organic layer was then filtered and concentrated to obtain a crude product, and the crude product was purified by column chromatography (silica gel, chloroform) to prepare 208 mg of 2,6-bis[5-(3,7-dimethyloctyl)thiophene-2-yl]-4,8-bisthiazole-2-yl-benzo [1,2-d; 4,5-d']bisthiazole (DTHA-DBTH-DMOTH) as a yellow solid (yield: 92%).

Generation of an intended compound was confirmed by $^1$H-NMR measurement.

$^1$H NMR (400 MHz, CDCl$_3$): δ 8.17 (d, J=3.6 Hz, 2H), 7.71 (d, J=3.6 Hz, 2H), 7.60 (d, J=3.6 Hz, 2H), 6.88 (d, J=3.6 Hz, 2H), 2.92 (m, 4H), 1.80 (m, 2H), 1.53 (m, 6H), 1.34 (m, 6H), 1.18 (m, 6H), 0.96 (d, J=5.8 Hz, 6H), 0.88 (d, J=6.4 Hz, 12H).

[Chemical Formula 103]

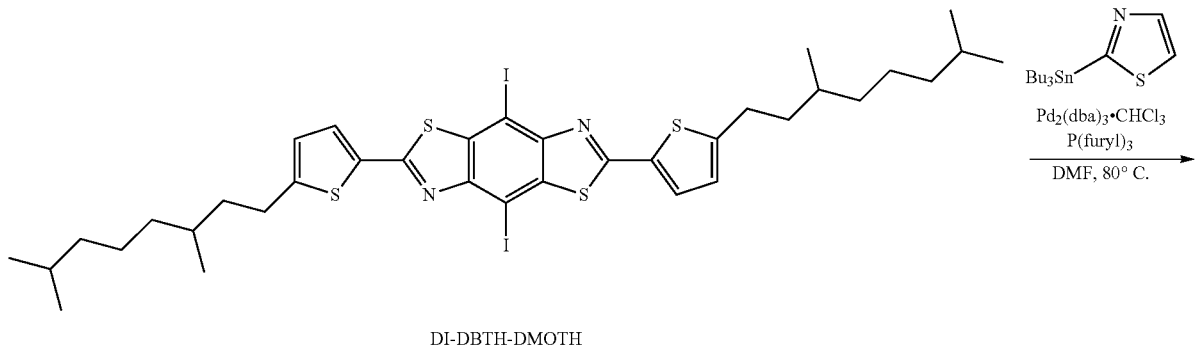

DI-DBTH-DMOTH

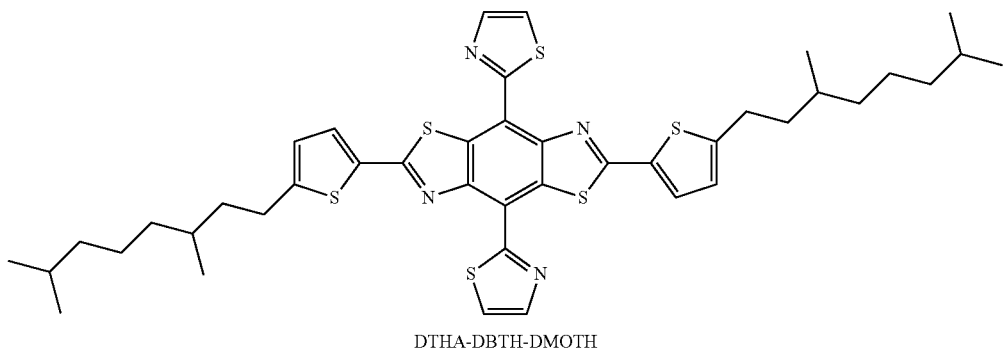

DTHA-DBTH-DMOTH

Example 34

Synthesis of 2,6-bis[5-(2-hexyldecyl)thiophene-2-yl]-4,8-bisthiazole-2-yl-benzo[1,2-d; 4,5-d']bisthiazole (DTHA-DBTH-HDTH)

[Chemical Formula 104]

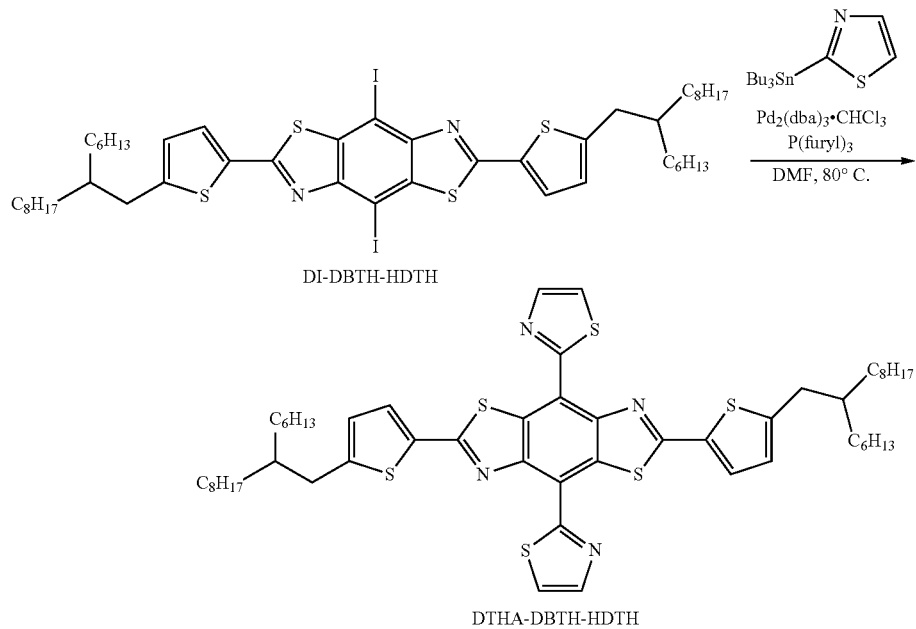

2,6-bis[5-(2-hexyldecyl)thiophene-2-yl]-4,8-diiodobenzo[1,2-d; 4,5-d']bisthiazole (DI-DBTH-HDTH, 800 mg, 0.76 mmol), 2-tributylstannylthiazole (708 mg, 1.89 mmol), tris(2-furyl)phosphine (29 mg, 0.12 mmol), a tris(dibenzylideneacetone)dipalladium (0)-chloroform adduct (32 mg, 30 μmol) and N,N-dimethylformamide (5 mL) were added in a 30 mL flask, and reacted at 80° C. for 17 hours. After the reaction was completed, the reaction product was cooled to room temperature, water was then added, the mixture was extracted twice with chloroform, and the organic layer was washed with water, and then dried with anhydrous magnesium sulfate. The organic layer was then filtered and concentrated to obtain a crude product, and the crude product was purified by column chromatography (silica gel, chloroform) to prepare 684 mg of 2,6-bis[5-(2-hexyldecyl)thiophene-2-yl]-4,8-bisthiazole-2-yl-benzo[1,2-d; 4,5-d']bisthiazole (DTHA-DBTH-HDTH) as a yellow solid (yield: 94%).

Generation of an intended compound was confirmed by $^1$H-NMR measurement.

$^1$H NMR (400 MHz, CDCl$_3$): δ 8.15 (d, J=3.46 Hz, 2H), 7.70 (d, J=3.6 Hz, 2H), 7.60 (d, J=3.6 Hz, 2H), 6.85 (d, J=3.6 Hz, 2H), 2.84 (m, 4H), 1.75 (m, 2H), 1.23-1.37 (m, 48H), 0.89 (t, J=6.4 Hz, 6H), 0.88 (t, J=6.4 Hz, 6H).

Example 35

Synthesis of 2,6-bis[5-(3,7-dimethyloctyl)thiophene-2-yl]-4,8-bis(5-tributylstannylthiazole-2-yl)-benzo[1,2-d; 4,5-d']bisthiazole (DTHA-DBTH-DMOTH-DSB)

[Chemical Formula 105]

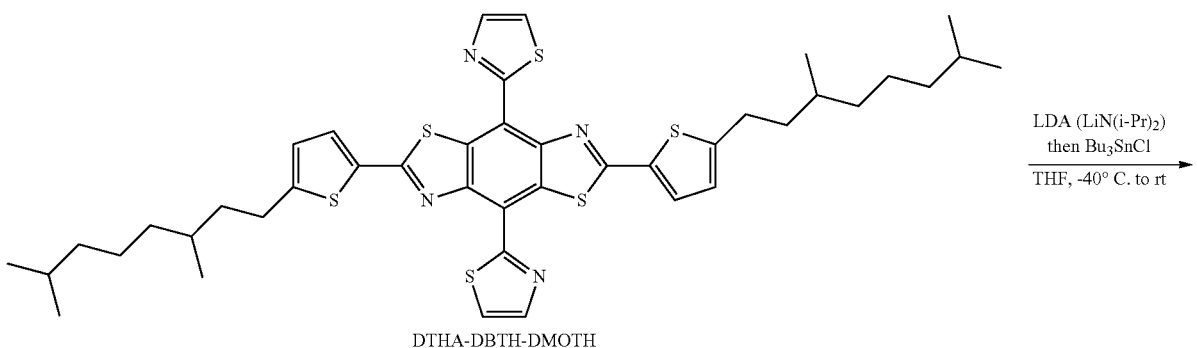

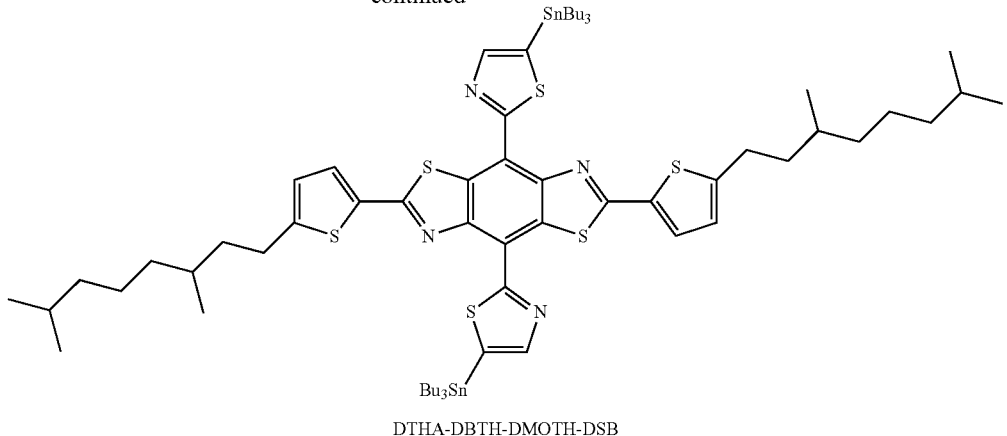

DTHA-DBTH-DMOTH-DSB 2,6-bis[5-(3,7-dimethyloctyl)thiophene-2-yl]-4,8-bisthiazole-2-yl-benzo[1,2-d; 4,5-d']bisthiazole (DTHA-DBTH-DMOTH, 205 mg, 0.26 mmol) and tetrahydrofuran (10 mL) were added in a 20 mL flask, and cooled to −40° C., lithium diisopropylamide (2 M solution, 0.27 mL, 0.54 mmol) was added dropwise, and the mixture was stirred for 30 minutes. Thereafter, tributyltin chloride (145 μL, 0.54 mmol) was added, and the mixture was heated to room temperature, and stirred for 2 hours. After the reaction was completed, water was added, the mixture was extracted twice with toluene, and the organic layer was washed with water, and then dried with anhydrous magnesium sulfate. Then, the organic layer was filtered and concentrated to obtain a crude product, and the crude product was purified by GPC-HPLC (JAIGEL-1H, 2H, chloroform) to prepare 158 mg of 2,6-bis[5-(3,7-dimethyloctyl)thiophene-2-yl]-4,8-bis(5-tributylstannylthiazole-2-yl)-benzo[1,2-d; 4,5-d']bisthiazole (DTHA-DBTH-DMOTH-DSB) as a light brown oil (yield: 45%).

Generation of an intended compound was confirmed by $^1$H-NMR measurement.

$^1$H NMR (400 MHz, $C_6D_6$): δ 8.43 (s, 2H), 7.62 (d, J=3.6 Hz, 2H), 6.58 (d, J=3.6 Hz, 2H), 2.72 (m, 4H), 1.77 (m, 14H), 1.53 (m, 18H), 1.34 (m, 18H), 1.13 (m, 6H), 1.04 (t, J=6.8 Hz, 18H), 0.96 (d, J=7.2 Hz, 12H), 0.88 (d, J=6.4 Hz, 6H).

Example 36

Synthesis of 2,6-bis[5-(2-hexyldecyl)thiophene-2-yl]-4,8-bis(5-tributylstannylthiazole-2-yl)-benzo[1,2-d; 4,5-d']bisthiazole (DTHA-DBTH-DMOTH-DSB)

[Chemical Formula 106]

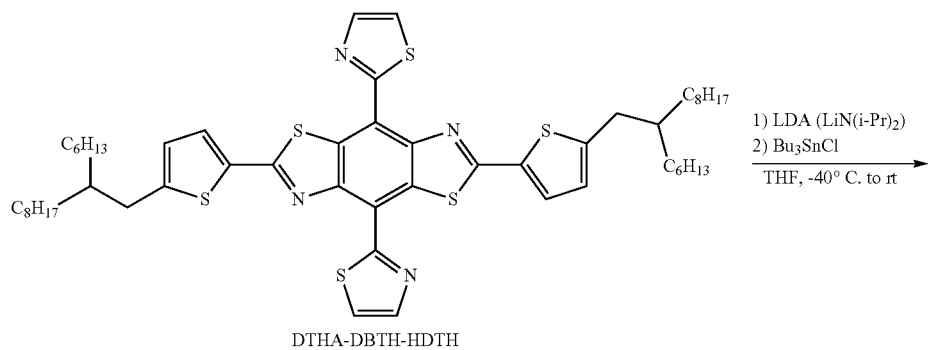

DTHA-DBTH-HDTH

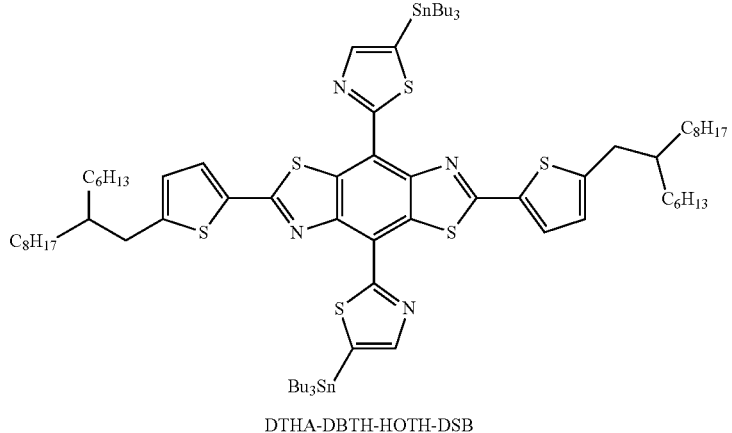

DTHA-DBTH-HOTH-DSB 2,6-bis[5-(2-hexyldecyl)thiophene-2-yl]-4,8-bisthiazole-2-yl-benzo[1,2-d; 4,5-d']bisthiazole (DTHA-DBTH-HDTH, 600 mg, 0.62 mmol) and tetrahydrofuran (24 mL) were added in a 20 mL flask, and cooled to −40° C., lithium diisopropylamide (2 M solution, 0.65 mL, 1.30 mmol) was added dropwise, and the mixture was stirred for 30 minutes. Thereafter, tributyltin chloride (352 μL, 1.30 mmol) was added, and the mixture was heated to room temperature, and stirred for 2 hours. After the reaction was completed, water was added, the mixture was extracted twice with toluene, and the organic layer was washed with water, and then dried with anhydrous magnesium sulfate. Then, the organic layer was filtered and concentrated to obtain a crude product, and the crude product was purified by GPC-HPLC (JAIGEL-1H, 2H, chloroform) to prepare 470 mg of 2,6-bis[5-(2-hexyldecyl)thiophene-2-yl]-4,8-bis(5-tributylstannylthiazole-2-yl)-benzo[1,2-d; 4,5-d']bisthiazole (DTHA-DBTH-HDTH-DSB) as a light brown oil (yield: 49%).

Generation of an intended compound was confirmed by $^1$H-NMR measurement.

$^1$H NMR (400 MHz, C$_6$D$_6$): δ 8.36 (s, 2H), 7.60 (d. J=3.6 Hz, 2H), 6.56 (d, J=3.6 Hz, 2H), 2.68 (m, 4H), 1.81-1.64 (m, 14H), 1.46-1.28 (m, 60H), 1.21-1.15 (m, 12H), 1.13 (m, 6H), 0.97 (t, J=6.8 Hz, 18H), 0.90 (t, J=6.4 Hz, 6H), 0.88 (t, J=6.4 Hz, 6H).

Example 37

Synthesis of P-THDMOT-DBTH-O-IMTH

[Chemical Formula 107]

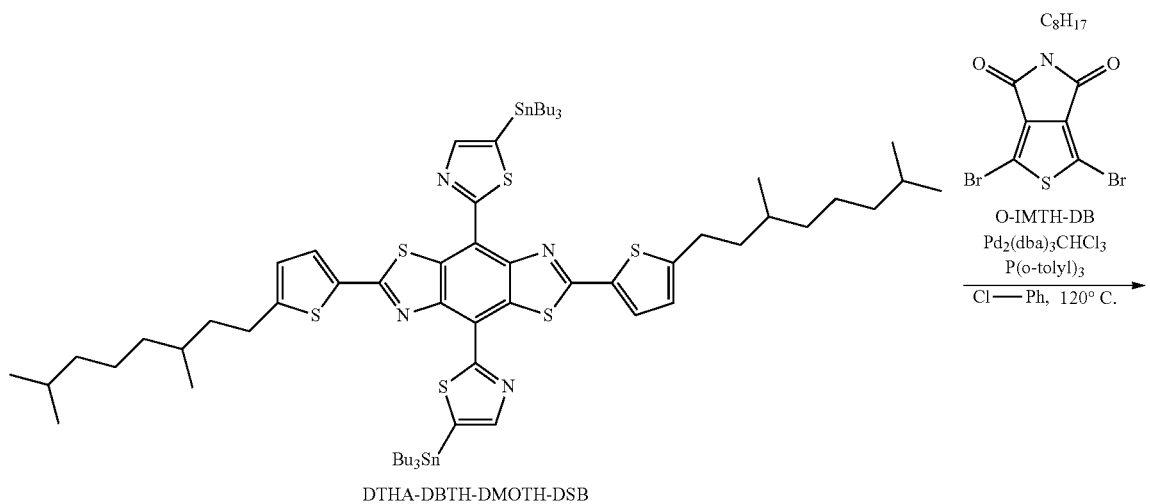

DTHA-DBTH-DMOTH-DSB

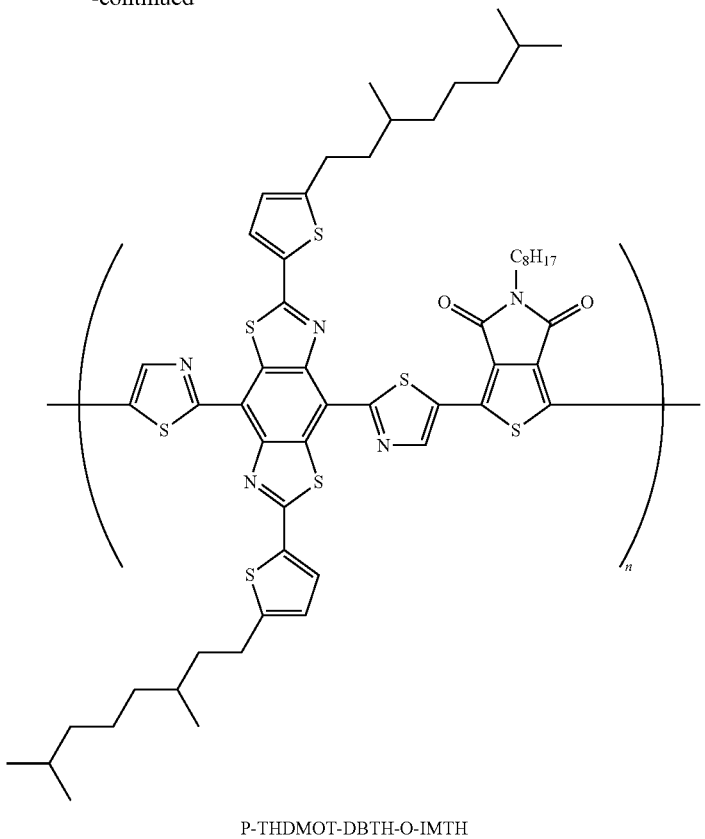

P-THDMOT-DBTH-O-IMTH 2,6-bis[5-(3,7-dimethyloctyl)thiophene-2-yl]-4,8-bis(5-tributylstannylthiazole-2-yl)-benzo[1,2-d; 4,5-d']bisthiazole (DTHA-DBTH-DMOTH-DSB, 88 mg, 0.06 mol), 1,3-dibromo-5-octylthieno[3,4-c]pyrrolo-4,6-dione (O-IMTH-DB, 26 mg, 0.06 mol), a tris(dibenzylideneacetone)dipalladium (0)-chloroform adduct (3 mg, 2.5 μmol), tris(o-tolyl)phosphine (3 mg, 10 μmol) and chlorobenzene (8 mL) were added in a 20 mL flask, and reacted at 120° C. for 24 hours. After the reaction was completed, the reaction liquid was added to methanol (50 mL), the precipitated solid was collected by filtration, and the obtained solid was subjected to Soxhlet washing (methanol, acetone and hexane). Then, the solid was subjected to Soxhlet extraction (chloroform) to prepare 34 mg (50%) of P-THDMOT-DBTH-O-IMTH as a black solid. The ultraviolet-visible absorption spectrum is shown in FIG. 12.

Ionization potential: 5.62 eV (HOMO −5.62 eV)

Example 38

Synthesis of P-THHDT-DBTH-EH-IMTH

[Chemical Formula 108]

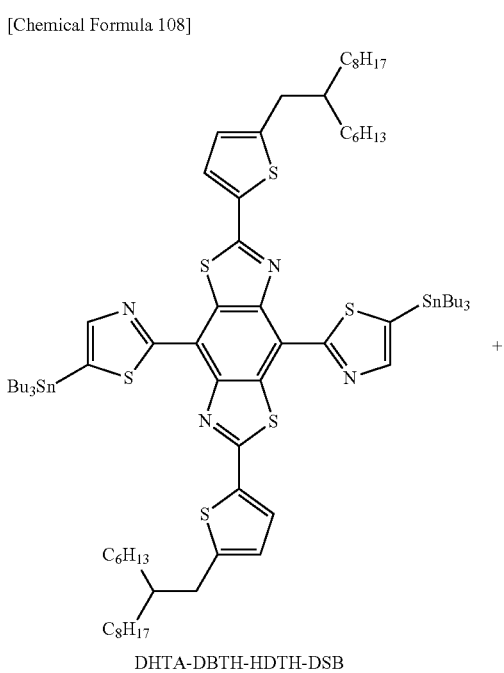

DHTA-DBTH-HDTH-DSB

129
-continued

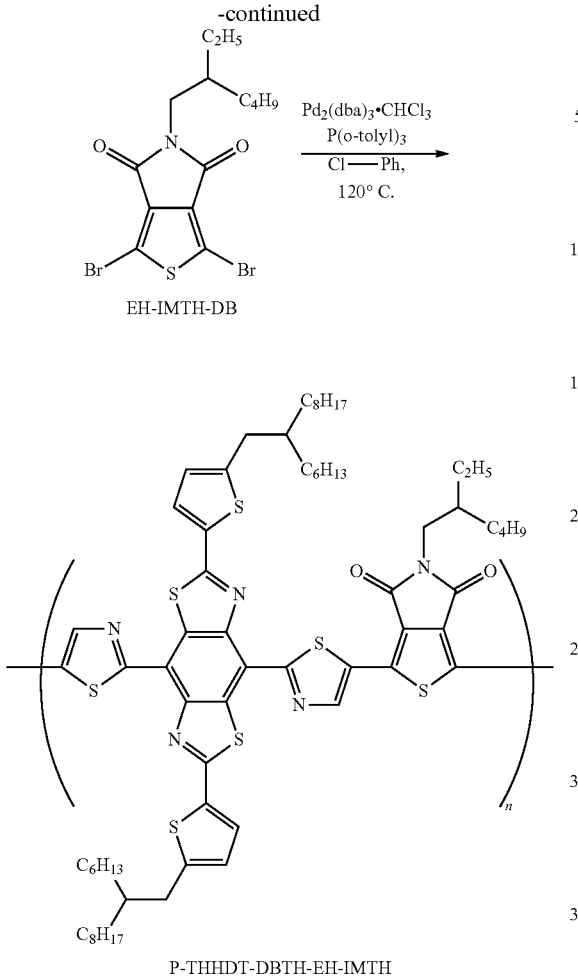

P-THHDT-DBTH-EH-IMTH 2,6-bis[5-(2-hexyldecyl)thiophene-2-yl]-4,8-bis(5-tributylstannylthiazole-2-yl)-benzo[1,2-d; 4,5-d']bisthiazole (DTHA-DBTH-HDTH-DSB, 130 mg, 0.08 mmol), 1,3-dibromo-5-(2-ethylhexyl)thieno[3,4-c]pyrrolo-4,6-dione (EH-IMTH-DB, 35 mg, 0.08 mmol), a tris(dibenzylideneacetone)dipalladium (0)-chloroform adduct (4 mg, 3.4 μmol), tris(o-tolyl)phosphine (4 mg, 13.4 μmol) and chlorobenzene (8 mL) were added in a 20 mL flask, and reacted at 120° C. for 22 hours. After the reaction was completed, the reaction liquid was added to methanol (60 mL), the precipitated solid was collected by filtration, and the obtained solid was subjected to Soxhlet washing (methanol, acetone and hexane). Then, the solid was subjected to Soxhlet extraction (chloroform) to prepare 78 mg (76%) of P-THHDT-DBTH-EH-IMTH as a black solid. The ultraviolet-visible absorption spectrum is shown in FIG. 13.

Ionization potential: 5.61 eV (HOMO −5.61 eV)
GPC measurement result: Mw (weight average molecular weight): 20300
Mn (number average molecular weight): 8800

130
Example 39

P-THHDT-DBTH-EH-IMTHT

[Chemical Formula 109]

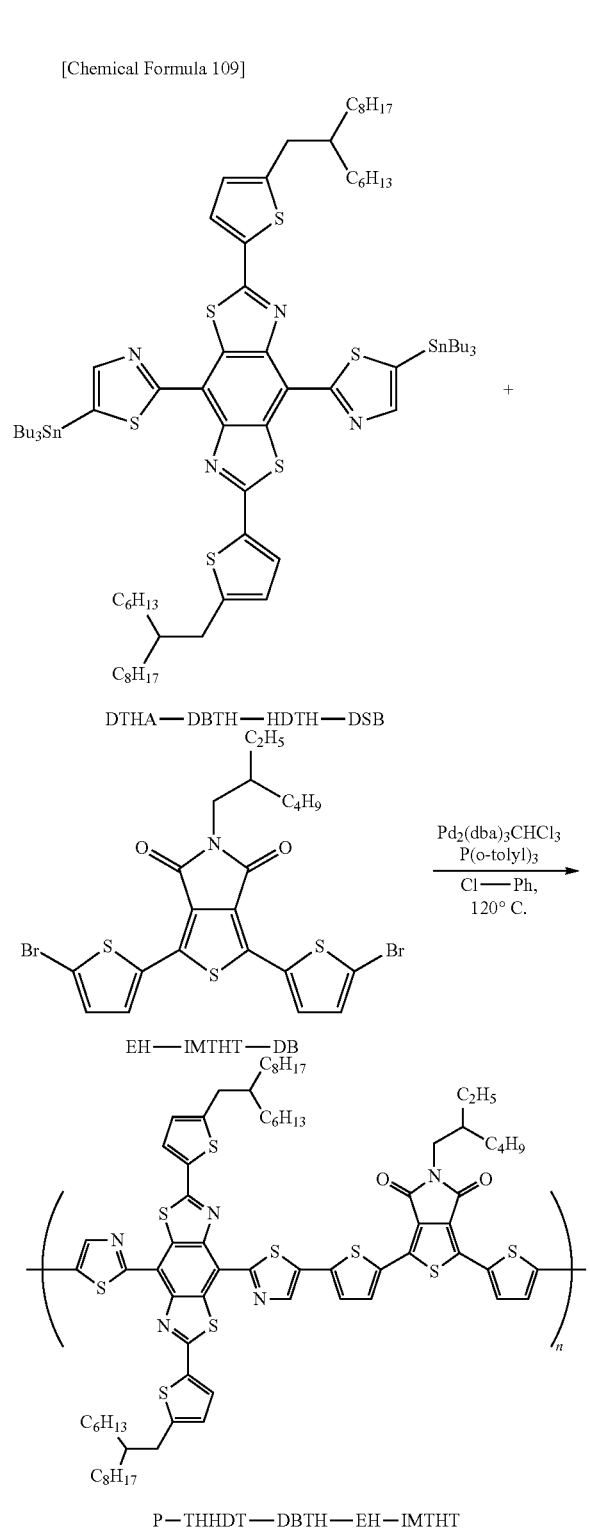

2,6-bis[5-(2-hexyldecyl)thiophene-2-yl]-4,8-bis(5-tributylstannylthiazole-2-yl)-benzo[1,2-d; 4,5-d']bisthiazole (DTHA-DBTH-HDTH-DSB, 110 mg, 0.07 mmol), 1,3-bis(5-bromothiophene-2-yl)-5-(2-ethylhexyl)thieno[3,4-c]pyrrolo-4,6-dione (EH-IMTHT-DB, 42 mg, 0.07 mmol), a tris(dibenzylideneacetone)dipalladium (0)-chloroform adduct (3 mg, 2.8 μmol), tris(o-tolyl)phosphine (4 mg, 11.3 μmol) and chlorobenzene (8 mL) were added in a 20 mL flask, and reacted at 120° C. for 22 hours. After the reaction was completed, the reaction liquid was added to methanol (40 mL), the precipitated solid was collected by filtration, and the obtained solid was subjected to Soxhlet washing (methanol, acetone and hexane). Then, the solid was subjected to Soxhlet extraction (chloroform) to prepare 35 mg (35%) of P-THHDT-DBTH-EH-IMTHT as a black solid. The ultraviolet-visible absorption spectrum is shown in FIG. 14.

Ionization potential: 5.42 eV (HOMO −5.42 eV)

Example 40

Synthesis of P-THHDT-DBTH-HTT

[Chemical Formula 110]

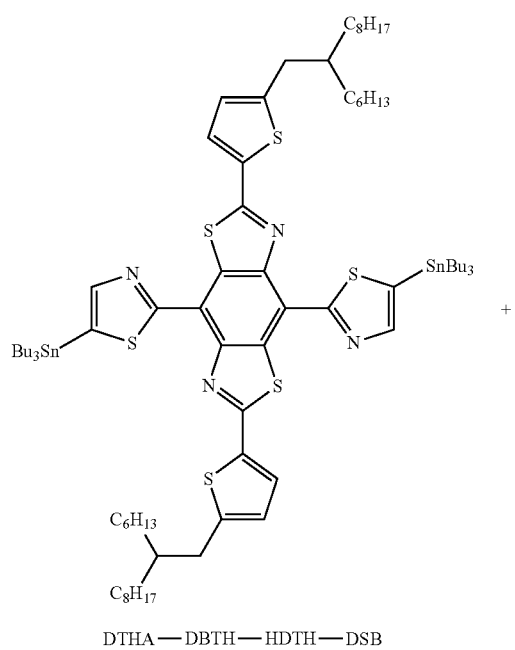

DTHA—DBTH—HDTH—DSB

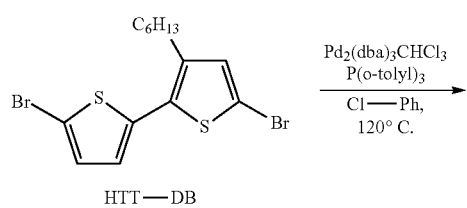

HTT—DB

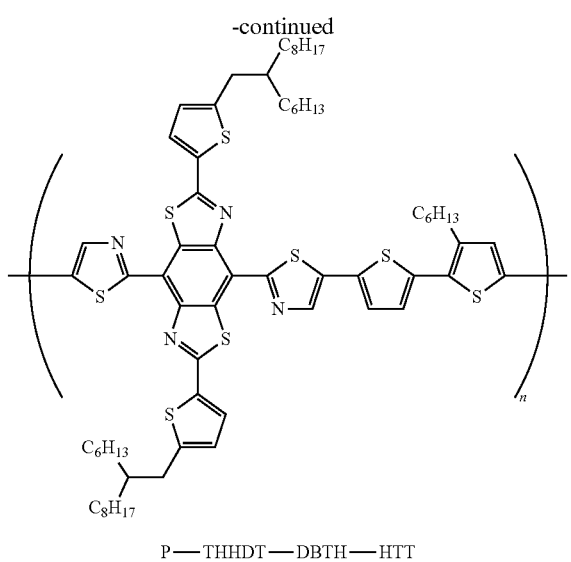

P—THHDT—DBTH—HTT 2,6-bis[5-(2-hexyldecyl)thiophene-2-yl]-4,8-bis(5-tributylstannylthiazole-2-yl)-benzo[1,2-d 4,5-d']bisthiazole (DTHA-DBTH-HDTH-DSB, 120 mg, 0.08 mmol), 5,5'-dibromo-3-hexyl[2,2']bithiophenyl (HTT-DB, 32 mg, 0.08 mmol), a tris(dibenzylideneacetone)dipalladium (0)-chloroform adduct (3 mg, 3.1 μmol), tris(o-tolyl)phosphine (4 mg, 12.3 μmol) and chlorobenzene (10 mL) were added in a 20 mL flask, and reacted at 120° C. for 24 hours. After the reaction was completed, the reaction liquid was added to methanol (60 mL), the precipitated solid was collected by filtration, and the obtained solid was subjected to Soxhlet washing (methanol, acetone and hexane). Then, the solid was subjected to Soxhlet extraction (chloroform) to prepare 72 mg (77%) of P-THHDT-DBTH-HTT as a black solid. The ultraviolet-visible absorption spectrum is shown in FIG. 15.

Ionization potential: 5.61 eV (HOMO −5.61 eV)

GPC measurement result: Mw (weight average molecular weight): 8400

Mn (number average molecular weight): 1600

Preparation and Evaluation of Photoelectric Conversion Element

Except that P-THHDT-DBTH-HTT prepared as described above was used in place of P-THDT-DBTH-EH-IMTH, the same procedure as in Example 30 was carried out to prepare a device. Properties were evaluated using a solar simulator (CEP 2000; AM 1.5 G filter; radiation intensity: 100 mW/cm$^2$; manufactured by JASCO Corporation) with the obtained device. The results showed that the Jsc (short-circuit current density) was 4.67 mA/cm$^2$, the Voc (open circuit voltage) was 0.59 V, the FF (fill factor) was 0.59, and the conversion efficiency was 1.62%.

Example 41

Synthesis of P-THHDT-DBTH-EH-BDT

[Chemical Formula 111]

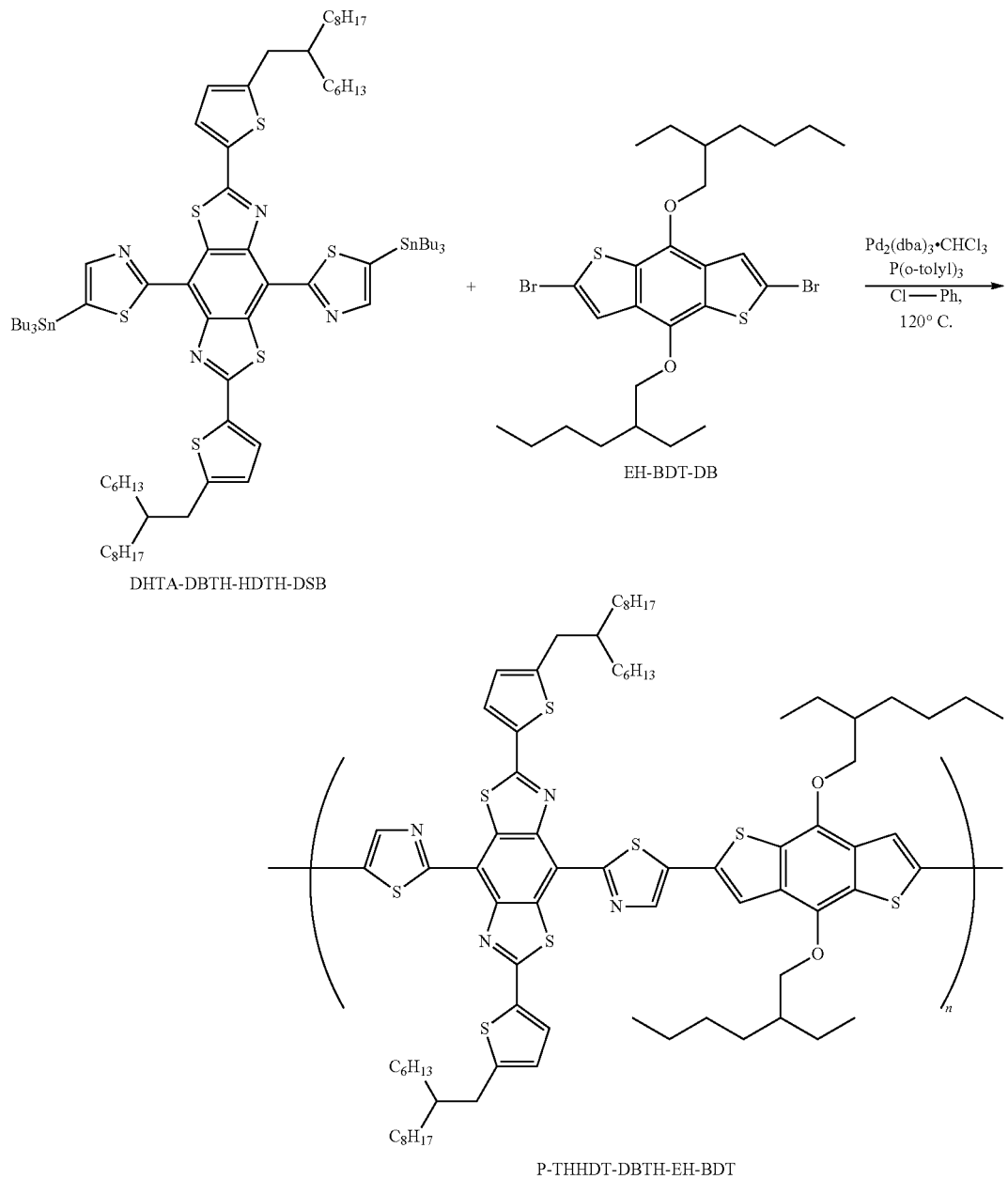

2,6-bis[5-(2-hexyldecyl)thiophene-2-yl]-4,8-bis(5-tributylstannylthiazole-2-yl)-benzo[1,2-d; 4,5-d']bisthiazole (DTHA-DBTH-HDTH-DSB, 120 mg, 0.08 mmol), 2,6-dibromo-4,8-bis(2-ethylhexyloxy)-1,5-dithia-s-indecene (EH-BDT-DB, 47 mg, 0.08 mmol), a tris(dibenzylideneacetone)dipalladium (0)-chloroform adduct (3 mg, 3.1 μmol), tris(o-tolyl)phosphine (4 mg, 12.3 μmol) and chlorobenzene (10 mL) were added in a 20 mL flask, and reacted at 120° C. for 25 hours. After the reaction was completed, the reaction liquid was added to methanol (50 mL), the precipitated solid was collected by filtration, and the obtained solid was subjected to Soxhlet washing (methanol, acetone and hexane). Then, the solid was subjected to Soxhlet extraction (chloroform) to prepare 70 mg (64%) of P-THHDT-DBTH-HTT as a dark red solid. The ultraviolet-visible absorption spectrum is shown in FIG. 16.

Ionization potential: 5.24 eV (HOMO −5.24 eV)
GPC measurement result: Mw (weight average molecular weight): 15200
Mn (number average molecular weight): 6500

Preparation and Evaluation of Photoelectric Conversion Element

P-THHDT-DBTH-EH-BDT prepared as described above was used as a donor material, and PCBM (C61) (phenyl C61-methyl butylate ester) was used as an acceptor material. The donor material and acceptor material (weight ratio: 1:2)

(total concentration: 30 mg/mL) and 1,8-diiodooctane (0.03 mL/mL) were dissolved in ortho-dichlorobenzene, and the solution was made to pass through a 0.45 μm-filter to obtain a mixed solution.

A glass substrate with ITO deposited thereon was surface-treated by subjecting the glass substrate to an ozone UV treatment, and PEDOT-PSS ([poly(3,4-ethylenedioxythiophene)-poly(styrenesulfonic acid)) was applied using a spin coater. Next, the donor material/acceptor material mixed solution was deposited using a spin coater, and dried under a reduced pressure at room temperature. An ethanol solution of titanium isopropoxide (about 0.3 v %) was applied by spin coating to form a film thereon which was converted into a titanium oxide film by moisture in the atmosphere. Thereafter, aluminum was vapor-deposited as an electrode to obtain a device.

Properties were evaluated using a solar simulator (CEP 2000; AM 1.5 G filter; radiation intensity: 100 mW/cm$^2$; manufactured by JASCO Corporation) with the obtained device. The results showed that the Jsc (short-circuit current density) was 3.65 mA/cm$^2$, the Voc (open circuit voltage) was 0.74 V, the FF (fill factor) was 0.47, and the conversion efficiency was 1.26%.

Example 42

Synthesis of 2,6-bis(5-triisopropylsilanylthiophene-2-yl)-benzo[1,2-d; 4,5-d']bisthiazole (DBTH-TIPSTH)

{Chemical Formula 112]

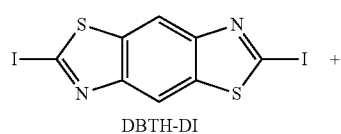

DBTH-DI

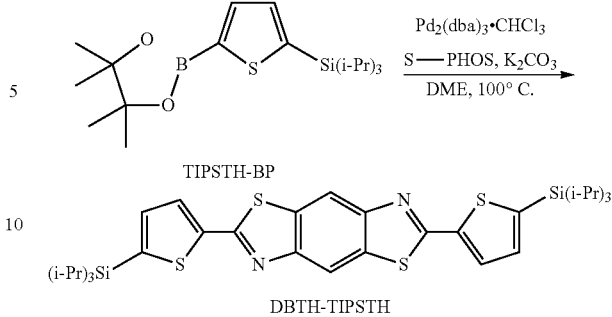

TIPSTH-BP

DBTH-TIPSTH 2,6-diiodobenzo[1,2-d; 4,5-d']bisthiazole (DBTH-DI, 1.5 g, 3.38 mmol), 4,4,5,5-tetramethyl-2-(5-triisopropylsilanyl-thiophene-2-yl)-[1,3,2]dioxaborolane (TIPSTH-BP, 3.1 g, 8.44 mmol), S-PHOS (2-dicyclohexylphosphino-2',6'-dimethoxybiphenyl, 111 mg, 0.27 mmol), a tris(dibenzylideneacetone)dipalladium (0)-chloroform adduct (140 mg, 0.14 mmol), 1,2-dimethoxyethane (120 mL) and water (30 mL) were added in 200 mL flask, and reacted at 110° C. for 18 hours. After the reaction was completed, the reaction product was cooled to room temperature, water and chloroform were then added, and the mixture was filtered over Celite, and extracted twice with chloroform. The organic layer was washed with water, then dried with anhydrous magnesium sulfate, and then filtered and concentrated to obtain a crude product, and the crude product was purified by column chromatography (silica gel, chloroform) to prepare 0.83 g of 2,6-bis(5-triisopropylsilanylthiophene-2-yl)-benzo[1,2-d; 4,5-d']bisthiazole (DBTH-TIPSTH) as a yellow solid (yield: 38%)

Generation of an intended compound was confirmed by $^1$H-NMR measurement.

$^1$H NMR (400 MHz, CDCl$_3$): δ 8.44 (s, 2H), 7.76 (d, J=3.6 Hz, 2H), 7.30 (d, J=3.6 Hz, 2H), 1.38 (m, 6H), 1.11 (d, J=7.5 Hz, 36H).

Example 43

Synthesis of 4,8-diiodo-2,6-bis(5-triisopropylsilanylthiophene-2-yl)-benzo[1,2-d; 4,5-d']bisthiazole (DI-DBTH-TIPSTH)

[Chemical Formula 113]

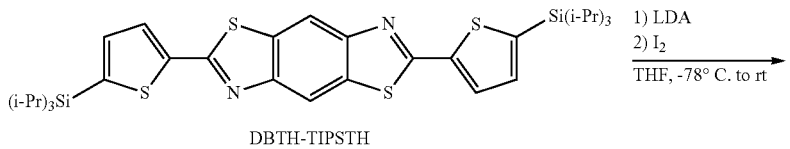

DBTH-TIPSTH

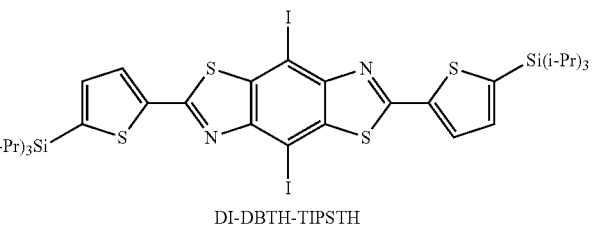

DI-DBTH-TIPSTH 2,6-bis(5-triisopropylsilanylthiophene-2-yl)-benzo[1,2-d; 4,5-d']bisthiazole (DBTH-TIPSTH, 600 mg, 0.90 mmol) and tetrahydrofuran (20 mL) were added in a 50 mL flask, and cooled to −30° C., and lithium diisopropylamide (1.5 M solution, 1.3 mL, 1.89 mmol) was then added dropwise. The mixture was then cooled to −80° C., iodine (1.14 mg, 4.48 mmol) was added, and the mixture was then reacted at room temperature for 2 hours. After the reaction was completed, 10% sodium hydrogen sulfite was added, the mixture was extracted with chloroform to obtain an organic layer, and the organic layer was washed with saturated sodium bicarbonate water, and then a saturated saline solution, and dried with anhydrous magnesium sulfate. The organic layer was filtered and concentrated to obtain a crude product, and the crude product was purified by column chromatography (silica gel, chloroform/hexane=1/1) to prepare 579 mg of 4,8-diiodo-2,6-bis(5-triisopropylsilanylthiophene-2-yl)-benzo[1,2-d; 4,5-d']bisthiazole (DI-DBTH-TIPSTH) as a yellow solid (yield: 70%).

Generation of an intended compound was confirmed by $^1$H-NMR measurement and high-resolution mass spectrum measurement.

$^1$H NMR (400 MHz, CDCl$_3$): δ 7.77 (d, J=2.8 Hz, 2H), 7.28 (d. J=2.8 Hz, 2H), 1.40 (sept, J=7.2 Hz, 6H), 1.14 (d, J=7.2 Hz, 36H).

High-resolution mass spectrometry (APCI: atmospheric pressure chemical ionization method)
Calculated value: $C_{34}H_{46}I_2N_2S_4Si_2$+H: 921.0245
Measured value: 921.02444

Example 44

Synthesis of 4,8-bis-(thiophene-2-yl)-2,6-bis(5-triisopropylsilanylthiophene-2-yl)-benzo[1,2-d; 4,5-d']bisthiazole (DBTH-TIPSTH-THA)

4,8-diiodo-2,6-bis(5-triisopropylsilanylthiophene-2-yl)-benzo[1,2-d; 4,5-d']bisthiazole (DI-DBTH-TIPSTH, 46 mg, 0.05 mmol), 2-tributylstannylthiazole (57 mg, 0.15 mmol), tris(2-furyl)phosphine (2 mg, 8 μmol), a tris(dibenzylideneacetone)dipalladium (0)-chloroform adduct (2 mg, 2 μmol) and tetrahydrofuran (2 mL) were added in a 10 mL flask, and reacted for 21 hours while heating under reflux. After the reaction was completed, the reaction product was cooled to room temperature, a 10% aqueous potassium fluoride solution was then added, the mixture was extracted twice with chloroform to obtain an organic layer, and the organic layer was dried with anhydrous magnesium sulfate. Then, the organic layer was filtered and concentrated to obtain a crude product, and the crude product was purified by column chromatography (silica gel, chloroform/hexane=1/1) to prepare 22 mg of 4,8-bisthiazole-2-yl-2,6-bis(5-triisopropylsilanylthiophene-2-yl)-benzo[1,2-d; 4,5-d']bisthiazole (DBTH-TIPSTH-THA) as a yellow solid (yield: 45%).

Generation of an intended compound was confirmed by $^1$H-NMR measurement, $^{13}$C-NMR measurement, IR spectrum measurement, melting point measurement, and high-resolution mass spectrum measurement.

$^1$H NMR (500 MHz, CDCl$_3$): δ 8.20 (d, J=3.3 Hz, 2H), 8.01 (d, J=3.6 Hz, 2H), 7.67 (d, J=3.3 Hz, 2H), 7.36 (d, J=3.6 Hz, 2H), 1.45 (sep, J=7.5 Hz, 6H), 1.19 (d, J=7.5 Hz, 36H).

$^{13}$C NMR (125 MHz, CDCl$_3$): δ 165.74, 161.98, 148.32, 142.31, 142.10, 141.29, 136.67, 131.61, 130.24, 122.81, 121.00, 17.85, 4.11.

IR (KBr): 2941, 1864, 1539, 1474, 1460, 1323, 999, 976, 659 cm$^{-1}$.

Melting point: resolved at 285° C.

High-resolution mass spectrometry (APCI: atmospheric pressure chemical ionization method)
Calculated value: $C_{40}H_{51}N_4S_6Si_2$+H: 835.1971
Measured value: 835.1999

[Chemical Formula 114]

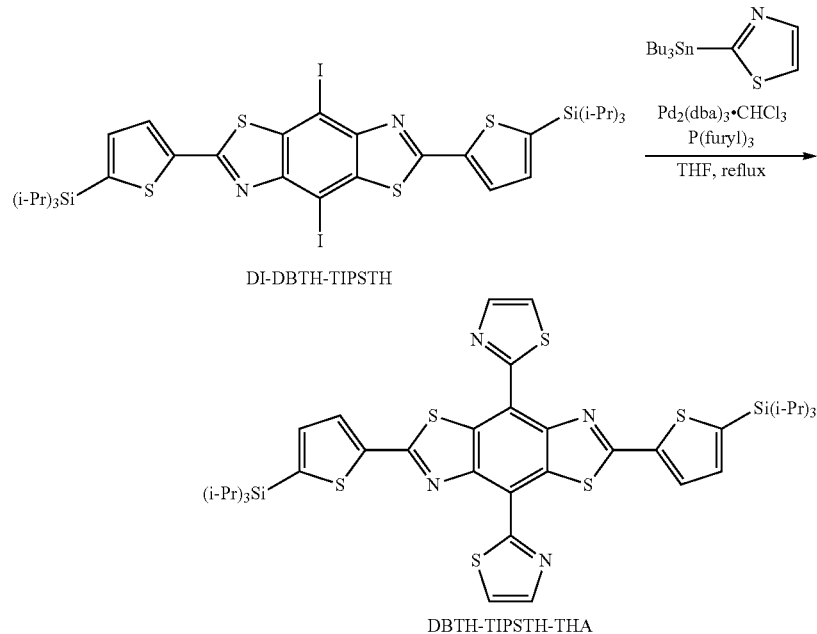

Example 45

Synthesis of 4,8-bis(5-tributylstannylthiophene-2-yl)-2,6-bis(5-triisopropylsilanylthiophene-2-yl)-benzo[1,2-d; 4,5-d']bisthiazole (DBTH-TIPSTH-THA-DSB)

[Chemical Formula 115]

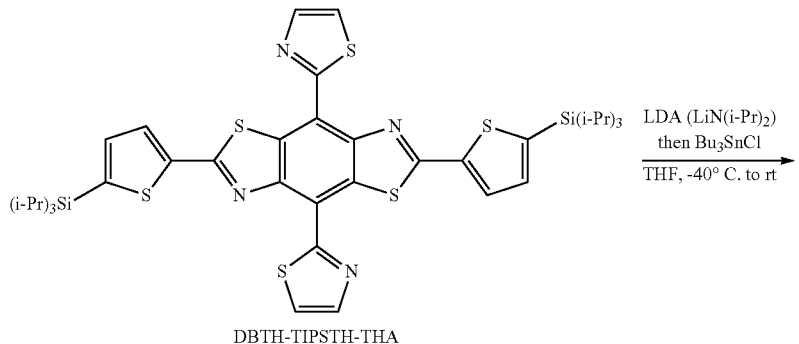

DBTH-TIPSTH-THA

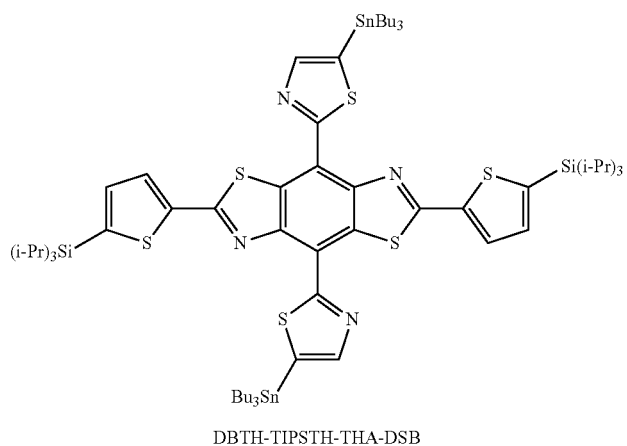

DBTH-TIPSTH-THA-DSB 4,8-bisthiazole-2-yl-2,6-bis(5-triisopropylsilanylthiophene-2-yl)-benzo[1,2-d; 4,5-d']bisthiazole (DBTH-TIPSTH-THA, 110 mg, 0.13 mmol) and tetrahydrofuran (4 mL) were added in a 20 mL flask, and cooled to −40° C., lithium diisopropylamide (2 M solution, 0.14 mL, 0.28 mmol) was added dropwise, and the mixture was stirred for 30 minutes. Thereafter, tributyltin chloride (75 μL, 0.28 mmol) was added, and the mixture was heated to room temperature, and stirred for 2 hours. After the reaction was completed, water was added, the mixture was extracted twice with toluene, and the organic layer was washed with water, and then dried with anhydrous magnesium sulfate. Then, the organic layer was filtered and concentrated to obtain a crude product, and the crude product was purified by GPC-HPLC (JAIGEL-1H, 2H, chloroform) to prepare 91 mg of 4,8-bis(5-tributylstannylthiophene-2-yl)-2,6-bis(5-triisopropylsilanylthiophene-2-yl)-benzo[1,2-d; 4,5-d']bisthiazole (DBTH-TIPSTH-THA-DSB) as a light brown oil (yield: 49%).

Generation of an intended compound was confirmed by $^1$H-NMR measurement.

$^1$H NMR (400 MHz, $C_6D_6$): δ 8.42 (s, 2H), 7.93 (d, J=3.6 Hz, 2H), 7.12 (d, J=3.6 Hz, 2H), 1.74 (m, 12H), 1.48 (m, 12H), 1.43 (sep, J=7.5 Hz, 6H), 1.27 (m, 12H), 1.21 (d, J=7.2 Hz, 36H), 0.98 (t, J=6.8 Hz, 18H).

Example 46

Synthesis of P-THTIPSTH-DBTH-O-IMTH

[Chemical Formula 116]

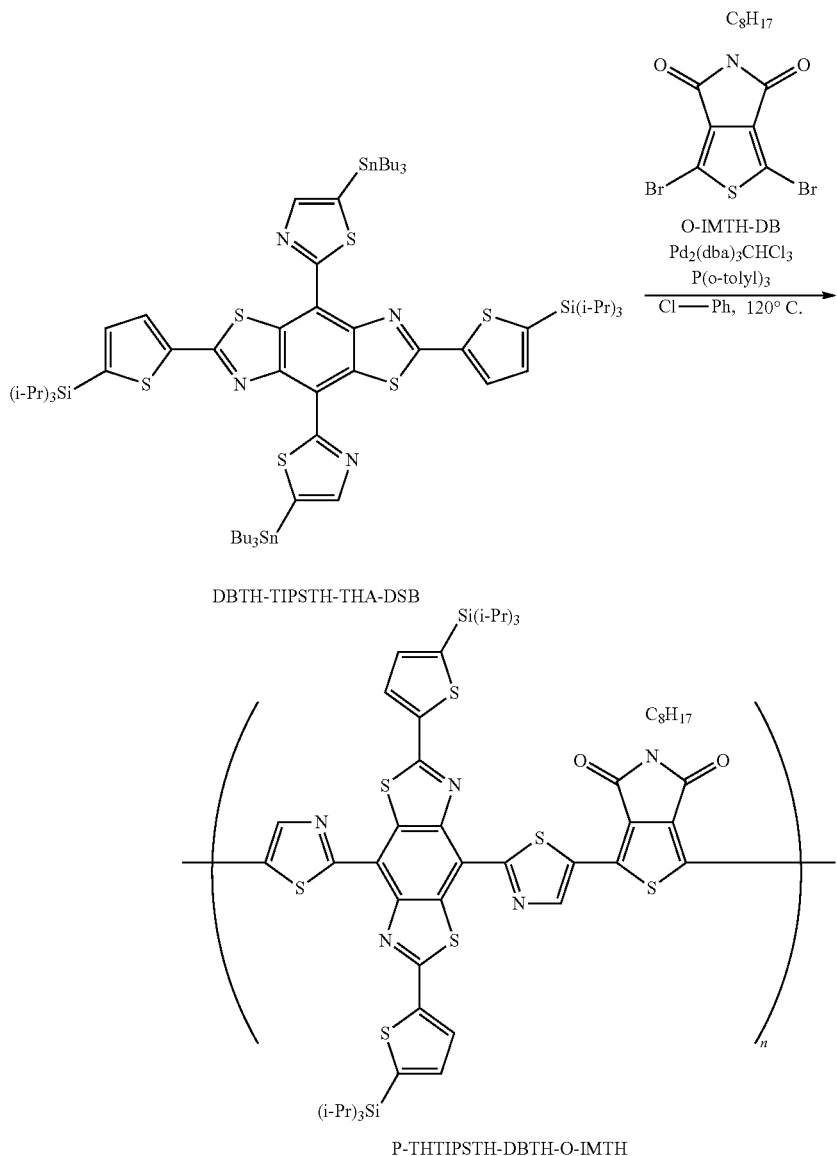

4,8-bis(5-tributylstannylthiophene-2-yl)-2,6-bis(5-triisopropylsilanylthiophene-2-yl)-benzo[1,2-d; 4,5-d']bisthiazole (DBTH-TIPSTH-THA-DSB, 88 mg, 0.06 mmol), 1,3-dibromo-5-octylthieno[3,4-c]pyrrolo-4,6-dione (O-IMTH-DB, 26 mg, 0.06 mmol), a tris(dibenzylideneacetone)dipalladium (0)-chloroform adduct (3 mg, 2.5 μmol), tris(o-tolyl)phosphine (4 mg, 10 μmol) and chlorobenzene (8 mL) were added in a 20 mL flask, and reacted at 120° C. for 24 hours. After the reaction was completed, the reaction liquid was added to methanol (50 mL), the precipitated solid was collected by filtration, and the obtained solid was subjected to Soxhlet washing (methanol, acetone and hexane). Then, the solid was subjected to Soxhlet extraction (chloroform) to prepare 34 mg (50%) of P-THTIPSTH-DBTH-O-IMTH as a black solid. The ultraviolet-visible absorption spectrum is shown in FIG. 17.

GPC Measurement Results

Mw (weight average molecular weight): 31800

Mn (number average molecular weight): 3300

Ionization potential: 5.65 eV (HOMO −5.65 eV)

Preparation and Evaluation of Photoelectric Conversion Element

P-THTIPSTH-DBTH-O-IMTH prepared as described above was used as a donor material, and PCBM (C61) (phenyl C61-methyl butylate ester) was used as an acceptor material. The donor material and acceptor material (weight ratio: 1:1.5) (total concentration: 20 mg/mL) and 1,8-diiodooctane (0.03 mL/mL) were dissolved in chlorobenzene, and the solution was made to pass through a 0.45 μm-filter to obtain a mixed solution.

A glass substrate with ITO deposited thereon was surface-treated by subjecting the glass substrate to an ozone UV treatment, and PEDOT-PSS ([poly(3,4-ethylenedioxythiophene)-poly(styrenesulfonic acid)) was applied using a spin coater. Next, the donor material/acceptor material mixed solution was deposited using a spin coater, and annealed at 150° C. An ethanol solution of titanium isopropoxide (about 0.3 v %) was applied by spin coating to form a film thereon which was converted into a titanium oxide film by moisture in the atmosphere. Thereafter, aluminum was vapor-deposited as an electrode to obtain a device.

Properties were evaluated using a solar simulator (CEP 2000; AM 1.5 G filter; radiation intensity: 100 mW/cm$^2$; manufactured by JASCO Corporation) with the obtained device. The results showed that the Jsc (short-circuit current density) was 2.23 mA/cm$^2$, the Voc (open circuit voltage) was 0.80 V, the FF (fill factor) was 0.36, and the conversion efficiency was 0.64%.

Example 47

Synthesis of P-THTIPSTH-DBTH-O-DPP 4,8-bis(5-tributylstannylthiophene-2-yl)-2,6-bis(5-triisopropylsilanylthiophene-2-yl)-benzo[1,2-d; 4,5-d']bisthiazole (DBTH-TIPSTH-THA-DSB, 106 mg, 0.07 mmol), 3,6-bis(5-bromothiophene-2-yl)-2,5-dioctyl-2,5-dihydropyrrolo[3,4-c]pyrrole-1,4-dione (O-DPP-DB, 49 mg, 0.07 mmol), a tris(dibenzylideneacetone)dipalladium (0)-chloroform adduct (3 mg, 2.9 μmol), tris(o-tolyl)phosphine (4 mg, 11.5 μmol) and chlorobenzene (10 mL) were added in a 20 mL flask, and reacted at 120° C. for 24 hours. After the reaction was completed, the reaction liquid was added to methanol (50 mL), the precipitated solid was collected by filtration, and the obtained solid was subjected to Soxhlet washing (methanol, acetone and hexane). Then, the solid was subjected to Soxhlet extraction (chloroform) to prepare 10 mg (10%) of P-THTIPSTH-DBTH-O-DPP as a black solid. The ultraviolet-visible absorption spectrum is shown in FIG. 18.

Ionization potential: 5.13 eV (HOMO −5.13 eV)

[Chemical Formula 117]

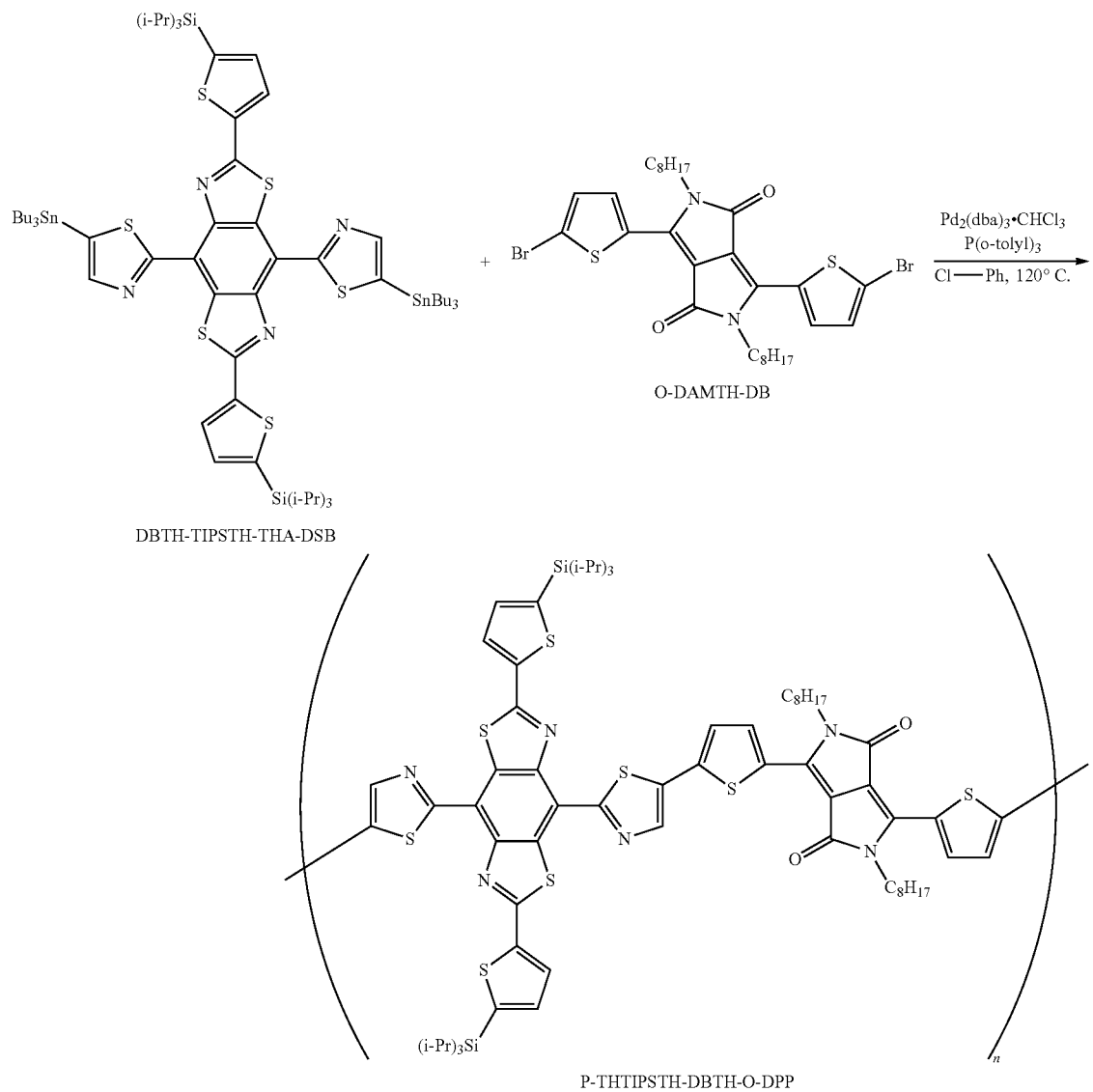

Example 48

Synthesis of 2,6-bis[5-(3,7-dimethyloctyl)thiophene-2-yl]-4,8-diethynylbenzo[1,2-d; 4,5-d']bisthiazole (DY-DBTH-DMOTH)

[Chemical Formula 118]

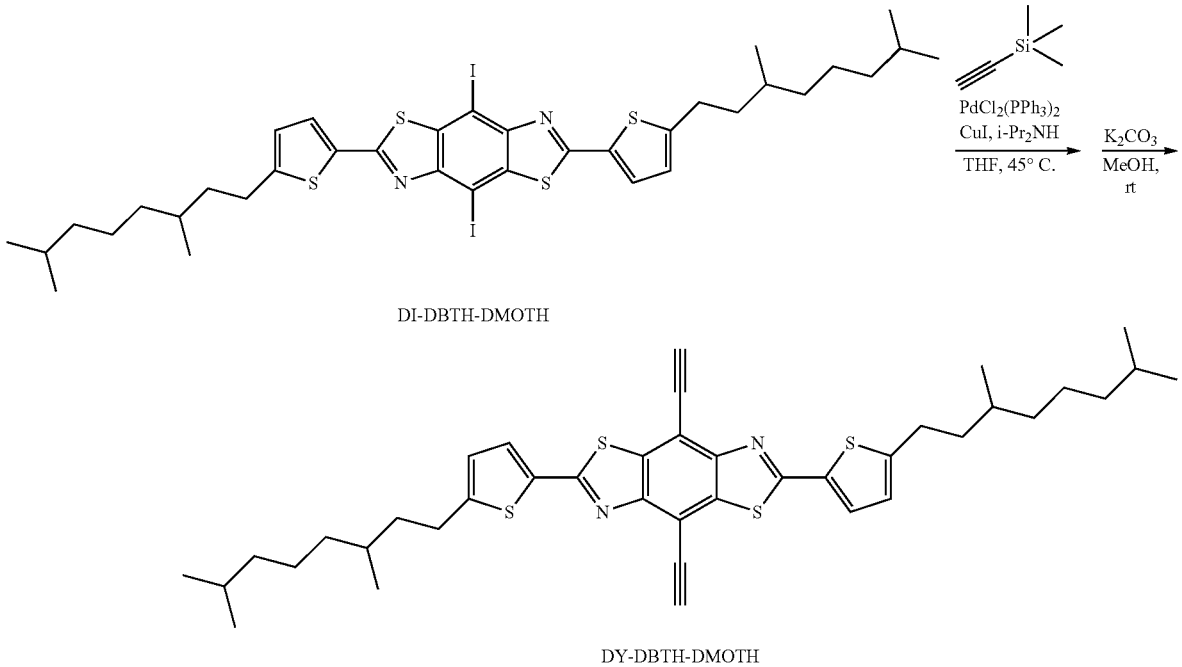

2,6-bis[5-(3,7-dimethyloctyl)thiophene-2-yl]-4,8-diiodobenzo[1,2-d; 4,5-d']bisthiazole (DI-DBTH-DMOTH, 100 mg, 0.11 mmol), trimethylsilylacetylene (47 μL, 0.33 mmol), copper iodide (I) (2 mg, 8.8 μmol), bis(triphenylphosphine)palladium (II)dichloride (7 mg, 8.8 μmol), tetrahydrofuran (2 mL) and diisopropylamine (2 mL) were added in a 10 mL flask, and reacted at 45° C. for 44 hours. Thereafter, volatile components were distilled out by concentration under a reduced pressure, potassium carbonate (15 mg, 0.11 mmol) and methanol (2 mL) were added, and the mixture was further reacted for 6 hours. After the reaction was completed, water was added, the mixture was extracted twice with chloroform to obtain an organic layer, and the organic layer was washed with water, and dried with anhydrous magnesium sulfate. Then, the organic layer was filtered and concentrated to obtain a crude product, and the crude product was purified by column chromatography (silica gel, chloroform/hexane=1/1) to prepare 32 mg (42%) of 2,6-bis[5-(3,7-dimethyloctyl)thiophene-2-yl]-4,8-diethynylbenzo[1,2-d; 4,5-d']bisthiazole (DY-DBTH-DMOTH) as a yellow solid.

Generation of an intended compound was confirmed by $^1$H-NMR measurement.

$^1$H NMR (400 MHz, CDCl$_3$): δ 7.55 (d, J=3.6 Hz, 2H), 6.84 (d, J=3.6 Hz, 2H), 3.89 (s, 2H), 2.89 (m, 4H), 1.78 (m, 2H), 1.53 (m, 6H), 1.34 (m, 6H), 1.18 (m, 6H), 0.96 (d, J=5.8 Hz, 6H), 0.88 (d, J=6.4 Hz, 12H).

Example 49

Synthesis of P-DMOTH-YDBTH-DMO-IMTH

[Chemical Formula 119]

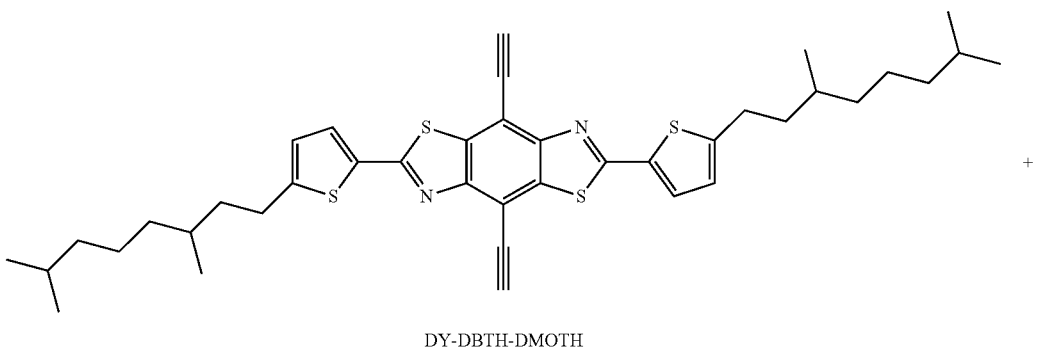

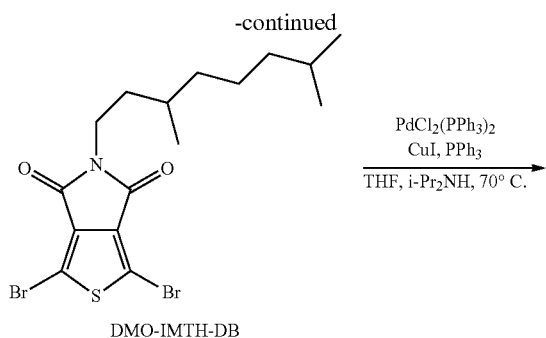

DMO-IMTH-DB

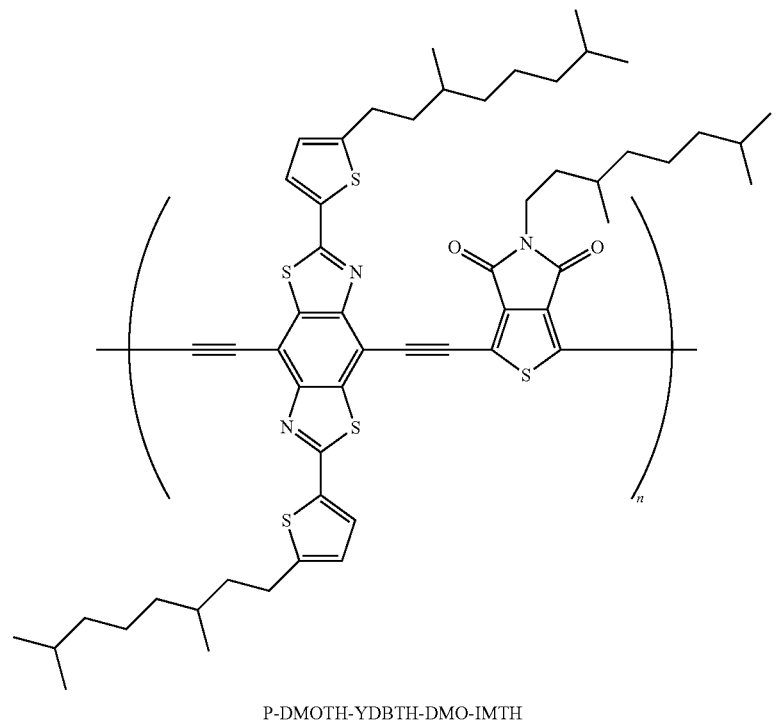

P-DMOTH-YDBTH-DMO-IMTH 2,6-bis[5-(3,7-dimethyloctyl)thiophene-2-yl]-4,8-diethynylbenzo[1,2-d;4,5-d']bisthiazole (DY-DBTH-DMOTH, 50 mg, 0.07 mmol), copper iodide (I) (3 mg, 15 μmol), bis(triphenylphosphine)palladium (II) dichloride (4 mg, 5.8 μmol), tetrahydrofuran (2 mL) and diisopropylamine (2 mL) were added in a 20 mL flask, and at 70° C. for 64 hours. After the reaction was completed, the reaction liquid was added to methanol (60 mL), the precipitated solid was collected by filtration, and the obtained solid was subjected to Soxhlet washing (methanol, acetone and hexane). Then, the solid was subjected to Soxhlet extraction (chloroform) to prepare 31 mg (43%) of P-DMOTH-YDBTH-DMO-IMTH as a dark red solid. The ultraviolet-visible absorption spectrum is shown in FIG. 19.

GPC Measurement Results

Mw (weight average molecular weight): 8700

Mn (number average molecular weight): 5700

Ionization potential: 6.18 eV (HOMO −6.18 eV)

INDUSTRIAL APPLICABILITY

The macromolecular compound according to the present invention has high photoelectric conversion efficiency, and is therefore useful in organic electronic devices and so on such as organic electroluminescence elements and organic thin-film transistor elements.

The invention claimed is:

1. A macromolecular compound comprising a benzobisthiazole structural unit represented by the formula (1) and an electron-donating structural unit or an electron-accepting structural unit, wherein the benzobisthiazole structural unit and the electron-donating structural unit or the electron-accepting structural unit are alternately arranged:

[Chemical Formula 1]

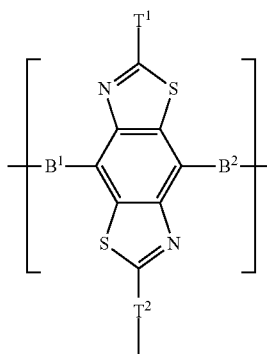

(1)

[in the formula (1),
T$^1$ and T$^2$ each independently represent an alkoxy group, a thioalkoxy group, a thiophene ring optionally substituted by a hydrocarbon group or an organosilyl group, a thiazole ring optionally substituted by a hydrocarbon group or an organosilyl group, or a phenyl group optionally substituted by a hydrocarbon group, an alkoxy group, a thioalkoxy group, an organosilyl group, a halogen atom or a trifluoromethyl group; and
B$^1$ and B$^2$ each represent a thiophene ring optionally substituted by a hydrocarbon group, or a thiazole ring optionally substituted by a hydrocarbon group].

2. The macromolecular compound according to claim 1, wherein T$^1$ and T$^2$ are each a group represented by any one of the following formulae (t1) to (t5):

[Chemical Formula 2]

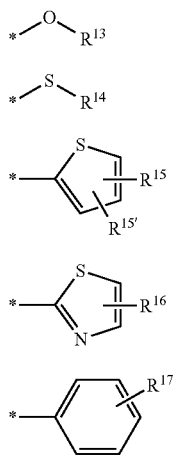

(t1)
(t2)
(t3)
(t4)
(t5)

[in the formulae (t1) to (t5),
R$^{13}$ and R$^{14}$ each independently represent a hydrocarbon group with a carbon number of 6 to 30;
R$^{15}$ and R$^{16}$ each independently represent a hydrocarbon group with a carbon number of 6 to 30, or a group represented by *—Si(R$^{18}$)$_3$;
R$^{15'}$ represents a hydrogen atom, a hydrocarbon group with a carbon number of 6 to 30, or a group represented by *—Si(R$^{18}$)$_3$;
R$^{17}$s each independently represent a hydrocarbon group with a carbon number of 6 to 30, *—O—R$^{19}$, *—S—R$^{20}$, *—Si(R$^{18}$)$_3$ or *—CF$_3$;

R$^{18}$s each independently represent an aliphatic hydrocarbon group with a carbon number of 1 to 20, or an aromatic hydrocarbon group with a carbon number of 6 to 10, and a plurality of R$^{18}$s may be each same or different;
R$^{19}$ and R$^{20}$ each represent a hydrocarbon group with a carbon number of 6 to 30; and
* represents a bond].

3. The macromolecular compound according to claim 1, wherein B$^1$ and B$^2$ are each a group represented by any one of the following formulae (b1) or (b2):

[Chemical Formula 3]

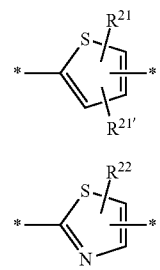

(b1)
(b2)

[in the formulae (b1) or (b2),
R$^{21}$, R$^{22}$ and R$^{21'}$ each represent a hydrogen atom, or a hydrocarbon group with a carbon number of 6 to 30; and * represents a bond, and in particular, * on the left side represents a bond of a benzobisthiazole compound to a benzene ring].

4. The macromolecular compound according to claim 1, which is a donor-acceptor-type semiconductor polymer.

5. An organic semiconductor material comprising the macromolecular compound according to claim 1.

6. A production method for the macromolecular compound according to claim 1, comprising:
using a compound selected from the group consisting of 2,6-diiodobenzo[1,2-d:4,5-d']bisthiazole and 2,6-dibromobenzo[1,2-d:4,5-d']bisthiazole as a starting material; and
going through a compound represented by the formula (2):

[Chemical Formula 8]

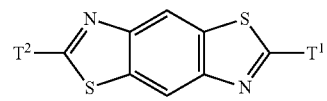

(2)

[in the formula (2),
T$^1$ and T$^2$ each independently represent an alkoxy group, a thioalkoxy group, a thiophene ring optionally substituted by a hydrocarbon group or an organosilyl group, a thiazole ring optionally substituted by a hydrocarbon group or an organosilyl group, or a phenyl group optionally substituted by a hydrocarbon group, an alkoxy group, a thioalkoxy group, an organosilyl group, a halogen atom or a trifluoromethyl group];

a compound represented by the formula (3):

[Chemical Formula 9]

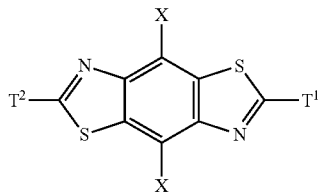

(3)

[in the formula (3),
T$^1$, T$^2$ each represent a group similar to one described above; and
X$^1$ and X$^2$ each represent a halogen atom]; and
a compound represented by the formula (4):

[Chemical Formula 10]

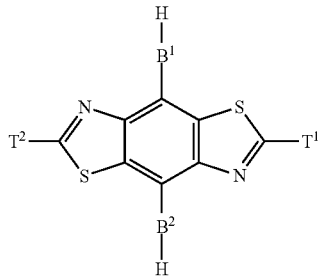

(4)

[in the formula (4),
T$^1$ and T$^2$ each represent a group similar to one described above; and
B$^1$ and B$^2$ each represent a thiophene ring optionally substituted by a hydrocarbon group, a thiazole ring optionally substituted by a hydrocarbon group, or an ethynylene group].

7. The production method according to claim 6, comprising the following first step, second step and third step:
the first step: a step of reacting a compound represented by the formula (6) and/or formula (7):

[Chemical Formula 11]

T$^1$-R$^5$ (6)

T$^2$-R$^6$ (7)

[in the formulae (6) and (7),
T$^1$ and T$^2$ each represent a group similar to one described above;
R$^5$ and R$^6$ each independently represent a hydrogen atom or *-M$^3$(R$^7$)$_k$R$^8$;
R$^7$ and R$^8$ each independently represent an aliphatic hydrocarbon group with a carbon number of 1 to 6, a hydroxyl group, an alkoxy group with a carbon number of 1 to 6, or an aryloxy group with a carbon number of 6 to 10;
M$^3$ represents a boron atom or a tin atom, and * represents a bond;
R$^7$ and R$^8$ may form a ring with M$^3$; and
k represents an integer of 1 or 2, and when k is 2, a plurality of R$^7$s may be each same or different]

with a compound selected from the group consisting of 2,6-diiodobenzo[1,2-d:4,5-d']bisthiazole and 2,6-dibromobenzo[1,2-d:4,5-d']bisthiazole in the presence of a metal catalyst to prepare a compound represented by the formula (2);
the second step: a step of reacting a base and a halogenation reagent with the compound represented by the formula (2) to prepare a compound represented by the formula (3); and
the third step: a step of reacting a compound represented by the following formula (8) and/or formula (9) with the compound represented by the formula (3) in the presence of a metal catalyst to prepare a compound represented by the formula (4):

[Chemical Formula 12]

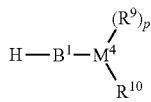

(8)

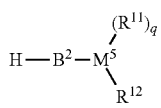

(9)

[in the formulae (8) and (9),
B$^1$ and B$^2$ each represent a group similar to one described above;
R$^9$ to R$^{12}$ each independently represent an aliphatic hydrocarbon group with a carbon number of 1 to 6, hydroxyl group, an alkoxy group with a carbon number of 1 to 6, an aryl group with a carbon number of 6 to 10, or an aryloxy group with a carbon number of 6 to 10;
M$^4$ and M$^5$ each represent a boron atom, a tin atom or a silicon atom;
R$^9$ and R$^{10}$ may form a ring with M$^4$, and R$^{11}$ and R$^{12}$ may form a ring with M$^5$; and
p and q each represent an integer of 1 or 2, and when p is 2, a plurality of R$^9$s may be each same or different, and when q is 2, a plurality of R$^{11}$s may be each same or different].

8. The production method according to claim 6, further comprising going through a compound represented by the formula (5):

[Chemical Formula 13]

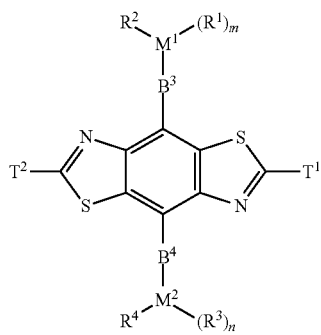

(5)

[in the formula (5),

T$^1$, T$^2$, B$^3$ and B$^4$ each represent a group similar to one described above;

R$^1$ to R$^4$ each independently an aliphatic hydrocarbon group with a carbon number of 1 to 6, hydroxyl group, an alkoxy group with a carbon number of 1 to 6, or an aryloxy group with a carbon number of 6 to 10;

M$^1$ and M$^2$ each independently represent a boron atom or a tin atom;

R$^1$ and R$^2$ may form a ring with M$^1$, and R$^3$ and R$^4$ may form a ring with M$^2$; and m and n each represent an integer of 1 or 2, and when m and n each represent 2, a plurality of R$^1$s and a plurality of R$^3$s may be each same or different.

9. The production method according to claim 8, further comprising the following fourth step:

the fourth step: a step of reacting a base and a tin halide compound with a compound represented by the formula (4) to prepare a compound represented by the formula (5).

\* \* \* \* \*